US007438907B2

(12) United States Patent
Schuurman et al.

(10) Patent No.: US 7,438,907 B2
(45) Date of Patent: Oct. 21, 2008

(54) HUMAN MONOCLONAL ANTIBODIES AGAINST CD25

(75) Inventors: Janine Schuurman, Amsterdam (NL); Catharina Emanuele Gerarda Havenith, Bodegraven (NL); Paul Parren, Odyk (NL); Jan G. J. Van De Winkel, Zeist (NL); Denise Leah Williams, San Jose, CA (US); Jørgen Petersen, Rungsted Kyst (DK); Ole Baadsgaard, Malmo (SE)

(73) Assignee: Genmab A/S, Copenhagen K (DK)

( * ) Notice: Subject to any disclaimer, the term of this patent is extended or adjusted under 35 U.S.C. 154(b) by 384 days.

(21) Appl. No.: 10/714,353

(22) Filed: Nov. 14, 2003

(65) Prior Publication Data

US 2004/0170626 A1 Sep. 2, 2004

Related U.S. Application Data

(60) Provisional application No. 60/426,690, filed on Nov. 15, 2002.

(51) Int. Cl.
*A61K 39/00* (2006.01)
*A61K 39/395* (2006.01)
*C07K 16/00* (2006.01)

(52) U.S. Cl. ............. 424/133.1; 424/144.1; 530/388.22
(58) Field of Classification Search ............... 424/1.331, 424/144.1; 530/388.22
See application file for complete search history.

(56) References Cited

U.S. PATENT DOCUMENTS

| | | | |
|---|---|---|---|
| 4,578,335 A | 3/1986 | Urdal et al. | |
| 4,816,565 A | 3/1989 | Honjo et al. | |
| 4,845,198 A | 7/1989 | Urdal et al. | |
| 5,011,684 A | 4/1991 | Strom | |
| 5,152,980 A | 10/1992 | Strom et al. | |
| 5,317,087 A | 5/1994 | Cerretti et al. | |
| 5,326,559 A | 7/1994 | Miller | |
| 5,336,489 A | 8/1994 | Strom | |
| 5,356,795 A | 10/1994 | Leonard et al. | |
| 5,510,105 A | 4/1996 | Strom | |
| 5,530,101 A * | 6/1996 | Queen et al. ............ | 530/387.3 |
| 5,587,162 A | 12/1996 | Strom | |
| 5,607,675 A | 3/1997 | Strom | |
| 5,674,494 A | 10/1997 | Strom | |
| 5,916,559 A | 6/1999 | Strom | |
| 6,074,636 A | 6/2000 | Nichols | |
| 6,113,900 A | 9/2000 | Strom | |
| 6,383,487 B1 | 5/2002 | Amlot et al. | |
| 2001/0041179 A1 | 11/2001 | Feutren et al. | |
| 2002/0012962 A1 | 1/2002 | Stahl et al. | |

FOREIGN PATENT DOCUMENTS

| | | |
|---|---|---|
| DE | 272471 | 10/1989 |
| EP | 421876 A1 | 10/1990 |
| EP | 296082 B1 | 4/1994 |
| EP | 548194 B1 | 5/1995 |
| EP | 380542 B1 | 4/1996 |
| EP | 510949 B2 | 4/2003 |
| WO | WO 88/09671 A1 | 12/1988 |
| WO | WO 89/01340 A1 | 2/1989 |
| WO | WO 89/11287 A1 | 11/1989 |
| WO | WO 91/00921 A1 | 1/1991 |
| WO | WO 92/03918 A1 | 3/1992 |
| WO | WO 92/04051 A1 | 3/1992 |
| WO | WO 92/13886 A1 | 8/1992 |
| WO | WO 92/15318 A1 | 9/1992 |
| WO | WO 92/20364 A1 | 11/1992 |
| WO | WO 92/20701 A2 | 11/1992 |
| WO | WO 94/25585 A1 | 11/1994 |
| WO | WO 98/24884 A1 | 6/1998 |
| WO | WO 99/36437 A1 | 7/1999 |
| WO | WO 99/43798 A1 | 9/1999 |
| WO | WO 00/18932 A2 | 4/2000 |
| WO | WO 00/25816 A1 | 5/2000 |
| WO | WO 00/30679 A1 | 6/2000 |
| WO | WO 00/71159 A1 | 11/2000 |
| WO | WO 02/07783 A2 | 1/2002 |
| WO | WO 02/07783 A3 | 1/2002 |

OTHER PUBLICATIONS

Burgess et al, Journal of Cell Biology vol. 111 Nov. 1990 2129-2138.*
Lazar et al Molecular and Cellular Biology Mar. 1988 vol. 8 No. 3 1247-1252.*

(Continued)

*Primary Examiner*—David J. Blanchard
*Assistant Examiner*—Lynn Bristol
(74) *Attorney, Agent, or Firm*—Lahive & Cockfield, LLP; Jane E. Remillard, Esq.

(57) ABSTRACT

Isolated human monoclonal antibodies which bind to and inhibit human CD25, and related antibody-based compositions and molecules, are disclosed. The human antibodies can be produced by a hybridoma, a transfectoma or in a nonhuman transgenic animal, e.g., a transgenic mouse, capable of producing multiple isotypes of human monoclonal antibodies by undergoing V-D-J recombination and isotype switching. Also disclosed are pharmaceutical compositions comprising the human antibodies, nonhuman transgenic animals, hybridomas and transfectomas which produce the human antibodies, and therapeutic and diagnostic methods for using the human antibodies.

31 Claims, 16 Drawing Sheets

OTHER PUBLICATIONS

Schwartz et al, Proc Natl Acad Sci USA vol. 84:6408-6411 (1987).*
Lin et al Biochemistry USA vol. 14:1559-1563 (1975).*
Rudikoff et al. (Proc. Natl. Acad. Sci USA 1982 79:1979) 1983.*
Green (J. Immunol. Methods 231:11-23 (1999).*
Osterberg et al. (Biochemical Society Transactions 23:1038-1043 (1995).*
Henry et al. (Expert Opin. Pharmacother. 3(11):1657-1663 (2002).*
Pascual et al. Nephrol Dial Transplant 16:1756-1760 (2001).*
Davis et al. (1999) Can. Metastasis Rev. 18:421-425.*
Gallo et al. Eur. J. Immunol. (2000) 30:534-540.*
MacCallum et al. (1996) J. Mol. Biol. 262:732-745.*
Pascalis et al. (2002) The Journal of Immunology 169:3076-3084.*
Casset et al. (2003) BBRC 307, 198-205.*
Holm et al (2007) Mol. Immunol. 44: 1075-1084.*
Chen et al. J. Mol. Bio. (1999) 293, 865-881.*
Wu et al. J. Mol. Biol. (1999) 294, 151-162.*
Jang et al. (1998) Molec. Immunol. 35:1207-1217.*
Brorson et al. (1999) J. Immunol. 163:6694-6701.*
Coleman (1994) Research in Immunol. 145:33-36.*
Vajdos et al. (2002) J. Mol. Biol. 320, 415-428.*
Preston et al. (Infect. Immun. 66(9):4137-4142 (1998)).*
Yarnold and Fell (Can. Res. 54:506-512 (1994)).*
Morrison et al. (PNAS 88:6851-6855 (1994)).*
Boel et al. (J. Immunol. Methods 239:153-166 (2000)).*
Leonard et al. "Molecular cloning and expression of cDNAs for the human interleukin-2 receptor." *Nature*. Oct. 18-24, 1984;311(5987):626-31.
Nikaido et al. "Molecular cloning of cDNA encoding human interleukin-2 receptor." *Nature*. Oct. 18-24, 1984;311(5987):631-5.
Uchiyama et al. "A monoclonal antibody (anti-Tac) reactive with activated and functionally mature human T cells. I. Production of anti-Tac monoclonal antibody and distribution of Tac (+) cells." *J Immunol*. Apr. 1981;126(4):1393-7.
Jakobovits, Aya, "The long-awaited magic bullets: therapeutic human monoclonal antibodies from transgenic mice," *Exp. Opin. Invest. Drugs.*, vol. 7(4):607-614.
Green, Larry L., "Antibody engineering via genetic engineering of the mouse: XenoMouse strains are a vehicle for the facile generation of therapeutic human monoclonal antibodies," *Journal of Immunological Methods*, vol. 231:11-23 (1999).
Henry, Mitchell L. et al., "The use of basiliximab in solid organ transplantation," *Expert Opin. Pharmacother.*, vol. 3(10):1657-1663 (2002).
Östberg, L. et al., "Human and humanized monoclonal antibodies: preclinical studies and clinical experience," *Biochemical Society Transactions*, vol. 23(4):1038-1043 (1995).
Pascual, Julio et al., "Anti-interleukin-2 receptor antibodies: basiliximab and daclizumab," *Nephrol Dial Transplant*, vol. 16:1756-1760 (2001).
Supplementary European Search Report for Application No. EP03786661, dated Mar. 23, 2007.
Baan, Carla C. et al., "Anti-CD25 Therapy Reveals the Redundancy of the Intragraft Cytokine Network After Clinical Heart Transplantation," *Transplantation*, vol. 67(6):870-876 (1999).
Baan, Carla C. et al., "Functional Responses of T Cells Blocked by Anti-CD25 Antibody Therapy During Cardiac Rejection," *Transplantation*, vol. 69(3):331-336 (2000).
Baan, Carla C. et al., "IL-15R α-Chain Expression During Anti-CD25 Treatment of Cardiac Allograft Recipients," *Transplantation Proceedings*, vol. 34:3243-3245 (2002).
Benito, José M. et al., "Quantitative Alterations of the Functionally Distinct Subsets of CD4 and CD8 T Lymphocytes in Asymptomatic HIV Infection: Changes in the Expression of CD45RO, CD45RA, CD11b, CD38, HLA-DR, and CD25 Antigens," *Journal of Acquired Immune Deficiency Syndromes and Human Retrovirology*, vol. 14(2):128-135 (1997).
Engert, Andreas et al., "A Phase-I Study of an Anti-CD25 Ricin A-Chain Immunotoxin (RFT5-SMPT-dgA) in Patients With Refractory Hodgkin's Lymphoma," *Blood*, vol. 89(2):403-410 (1997).
Hartmann, Frank et al., "Radioimmunotherapy of Nude Mice Bearing a Human Interleukin 2 Receptor α-expressing Lymphoma Utilizing the α-emitting Radionuclide-conjugated Monoclonal Antibody $^{212}$Bi-anti-Tac," *Cancer Research*, vol. 54:4362-4370 (1994).
Jakob, Thilo et al., "Stage-dependent Expression of CD7, CD45RO, CD45RA and CD25 on CD4-positive Peripheral Blood T-lymphocytes in Cutaneous T-cell Lymphoma," *Acta dermatovenereologica*, vol. 76(1):34-36 (1996).
Jones, Emma et al., "Depletion of CD25+ regulatory cells results in suppression of melanoma growth and induction of autoreactivity in mice," *Cancer Immunity*, vol. 2(1):1-12 (2002).
Kreitman, Robert J. et al., "Phase I Trial of Recombinant Immunotoxin Anti-Tac(Fv)-PE38 (LMB-2) in Patients With Hematologic Malignancies," *Journal of Clinical Oncology*, vol. 18(8):1622-1636 (2000).
Krueger, James G. et al., "Sucessful in vivo blockade of CD25 (high-affinity interleukin 2 receptor) on T cells by administration of humanized anti-Tac antibody to patients with psoriasis," *J. Am. Acad. Dermatol.*, vol. 43:448-458 (2000).
Kupiec-Weglinski, Jerzy W., "CD25-Targeted Therapy Revisited," *Transplantation*, vol. 69(3):328-330 (2000).
Laurie, Karen L. et al., "The role of CD4+CD25+ immunoregulatory T cells in the induction of autoimmune gastritis," *Immunology and Cell Biology*, vol. 80:567-573 (2002).
Mrowietz, Ulrich et al., "Treatment of Severe Psoriasis With Anti-CD25 Monoclonal Antibodies," *Arch. Dermatol.*, vol. 136:675-676 (2000).
Onizuka, Shozaburo et al., "Tumor Rejectino by In Vivo Administration of Anti-CD25 (Interleukin-2 Receptor α) Monoclonal Antibody," *Cancer Research*, vol. 59:3128-3133 (1999).
Pfister, K. et al., "The in vitro anti-inflammatory effects of recombinant anti-CD25 immunotoxin on lamina propria T cells of patients with inflammatory bowel disease are not sufficient to cure experimental colitis in mice," *Int. J. Colorectal Dis.*, vol. 17:77-84 (2002).
Sakaguchi, Shimon et al., "Immunologic tolerance maintained by CD25+ CD4+ regulatory T cells: their common role in controlling autoimmunity, tumor immunity, and transplantation tolerance," *Immunological Reviews*, vol. 182:18-32 (2001).
Schnell, R. et al., "Treatment of refractory Hodgkin's lymphoma patients with an anti-CD25 ricin A-chain immunotoxin," *Leukemia*, vol. 14:129-135 (2000).
Shevach, Ethan M., "CD4+CD25+ Suppressor T Cells: More Questions than Answers," *Nature Reviews*, vol. 2:389-400 (2002).
Shimizu, Jun et al., "Induction of Tumor Immunity by Removing CD25+CD4+ T Cells: A Common Basis Between Tumor immunity and Autoimmunity," *The Journal of Immunology*, vol. 163:5211-5218 (1999).
Shimizu, Jun et al., "Stimulation of CD25+CD4+ regulatory T cells through GITR breaks immunological self-tolerance," *Nature Immunology*, vol. 3(2):135-142 (2002).
Smith, Paul J. et al., "Characteristics of a Novel Deep Red/Infrared Fluorescent Cell-Permeant DNA Probe, DRAQ5, in Intact Human Cells Analyzed by Flow Cytometry, Confocal and Multiphoton Microscopy," *Cytometry*, vol. 40:280-291 (2000).
Steitz, Julia et al., "Depletion of CD25+ CD4+ T Cells and Treatment with Tyrosinase-related Protein 2-transduced Dendritic Cells Enhance the Interferon α-induced, CD8+ T-Cell-dependent Immune Defense of B16 Melanoma," *Cancer Research*, vol. 61:8643-8646 (2001).
Szabolcs, P. et al., "Combination treatment of bullous pemphigold with anti-CD20 and anti-CD25 antibodies in a patient with chronic graft-versus-host disease," *Bone Marrow Transplantation*, vol. 30:327-329 (2002).
van Besouw, N.M. et al., "Anti-CD25 Therapy Impairs Donor-Specific Th1 and Th2 Cytokine-Producing Peripheral Blood Cells After Clinical Heart Transplantation," *Transplantation Proceedings*, vol. 34:2942-2943 (2002).
Waldmann, Thomas A., "Anti-IL-2 Receptor Monoclonal Antibody (Anti-Tac) Treatment of T-Cell LYmphoma 8," *Important Advances in Oncology*, pp. 131-141 (1994).

Waldmann, Thomas A. et al., "Radioimmunotherapy of Interleukin-2Rα-Expressing Adult T-Cell Leukemia With Yttrium-90-Labeled Anti-Tac," *Blood*, vol. 86(11):4063-4075 (1995).

Wang, Hua et al., "TACI-ligand interactions are required for T cell activation and collagen-induced arthritis in mice," *Nature Immunology*, vol. 2(7):632-637 (2001).

Woo, Edward Y. et al., "Regulatory CD4+CD25+ T Cells in Tumors from Patients with Early-Stage Non-Small Cell Lung Cancer and Late-Stage Ovarian Cancer," *Cancer Research*, vol. 61:4766-4772 (2001).

* cited by examiner

Figure 1

Light chain sequences

```
1         10        20        30        40
EIVLTQSPGTLSLSPGERATLSCRASQSVSSSYLAWYQQK          germ-line
EIVLTQSPGTLSLSPGERATLSCRASQSVSSSFLAWYQQK          (1)  AB1
ENVLTQSPGTLSLSPGERATLSCRASQSGSSSYLAWYQQK          (1)  AB7
EIVLTQSPGTLSLSPGERATLSCRASQSVSSSFLAWYQQK          (1)  AB11
EIVLTQSPGTLSLSPGERATLSCRASQSVSS-YLAWYQQK          (1)  AB12

41        50        60        70        80
PGQAPRLLIYGASSRATGIPDRFSGSGSGTDFTLTISRLE          germ-line
PGQAPRLLIYGASSRATGIPDRFSGSGSGTDFTLTISRLE          (41) AB1
PGQAPRLLIYGASSRATGIPDRFSGSGSGTDFTLTISRLE          (41) AB7
PGQAPRLLIYGASSRATGIPDRFSGSGSGTDFTLTISRLE          (41) AB11
PGQAPRLLIYGASSRATGIPDRFSGSGSGTDFTLTISRLE          (41) AB12

81        90        100       110       120
PEDFAVYYCQQYGSSP-----------------------          germ-line
PEDFAVYYCQQYSSSPLTFGGGTKVEIKRTVAAPSVFIFP          (81) AB1
PEDFAVYYCQQYGSSPITFGQGTRLEIKRTVAAPSVFIFP          (81) AB7
PEDFAVYYCQQYSSSPLTFGGGTKVEIKRTVAAPSVFIFP          (81) AB11
PEDFAVYYCQQYGSSPLTFGGGTKVEIKRTVAAPSVFIFP          (81) AB12
```

CDR1, CDR2, and CDR3 have been underlined.

Figure 2

Heavy chain sequences

```
1         10        20        30        40
QVQLVQSGAEVKKPGSSVKVSCKASGGTFSSYAISWVRQA         germ-line
QVQLVQSGAEVKKPGSSVKVSCKASGGTFSRYPINWVRQA    (1)  AB1
QVQLVQSGAEVKKPGSSVKVSCKASGGTFSRYAINWVRQA    (1)  AB7
QVQLVQSGAEVKKPGSSVKVSCKASGGTFSRYPINWVRQA    (1)  AB11
QVQLVQSGAEVKKPGSSVKVSCKASGGTFSRYIINWVRQA    (1)  AB12

41        50        60        70        80
PGQGLEWMGRIIPILGIANYAQKFQGRVTITADKSTSTAY         germ-line
PGQGLEWMGRIIPILGIADYAQRFQGRVTITADKSTNTAY    (43) AB1
PGQGLEWMGRIIPILDIADYAQKFQDRVTITADKSTNTAY    (43) AB7
PGQGLEWMGRIIPILGIADYAQRFQGRVTITADKFTNTAY    (43) AB11
PGQGLEWMGRIIPILGVENYAQKFQGRVTITADKSTSTAY    (43) AB12

81        90        100       110       120
MELSSLRSEDTAVYYCAR-----------------------        germ-line
MELSSLRSEDTAVYYCARRDWGDYWGQGTLVTVSSASTKG    (85) AB1
MELSSLRSEDTAVYYCARKDWFDPWGQGTLVTVSSASTKG    (85) AB7
MELSSLRSEDTAVYYCARRDWGDYWGQGTLVTVSSASTKG    (85) AB11
MELSSLRSEDTAVYYCARKDWFDYWGQGTLVTVSSASTKG    (85) AB12

121
-------                germ-line
PSVFPLA           (121) AB1
PSVFPLA           (121) AB7
PSVFPLA           (121) AB11
PSVFPLA           (121) AB12
```

CDR1, CDR2, and CDR3 regions have been underlined.

Figure 3

VHAB1noleader

```
         AB62
         ├──────────────────────────────────────── FR1 ────────────────────────────────────────┤
      Q   V   Q   L   V   Q   S   G   A   E   V   K   K   P   G   S   S   V   K   V
+1
 1    CAGGTTCAGC TGGTGCAGTC TGGGGCTGAG GTGAAGAAGC CTGGGTCCTC GGTGAAAGTC
                                                                      ├─── FR2 ───
                                       ├─────── CDR1 ───────┤
      S   C   K   A   S   G   T   F   S   R   Y   P   I   N   W   V   R   Q   A
+1
61    TCCTGCAAGG CTTCTGGAGG CACCTTCAGC CGTTATCCTA TCAACTGGGT GCGACAGGCC
         ────────────── FR2 ──────────────┤       ├─────────── CDR2 ───────────
      P   G   Q   G   L   E   W   M   G   R   I   I   P   I   L   G   I   A   D   Y
+1
121   CCTGGACAAG GGCTTGAGTG GATGGGAAGG ATCATCCCTA TCCTTGGTAT AGCAGACTAC
              CDR2 ────────┤                     ├──────────────── FR3
      A   Q   R   F   Q   G   R   V   T   I   T   A   D   K   S   T   N   T   A   Y
+1
181   GCACAGAGGT TCCAGGGCAG AGTCACGATT ACCGCGGACA AATCCACGAA CACAGCCTAC
                                                                      ├── CDR3 ──
                                                                      ├─── JH4b
      M   E   L   S   S   L   R   S   E   D   T   A   V   Y   Y   C   A   R   R   D
+1
241   ATGGAGCTGA GCAGCCTGAG ATCTGAGGAC ACGGCCGTGT ATTATTGTGC GAGGAGGGAC
         ──────────────── FR3 ────────────────┤
                                                                    gamma-1 constant
         AB90                                                       ────────────────
      W   G   D   Y   W   G   Q   G   T   L   V   T   V   S   S   A   S   T   K   G
+1
301   TGGGGAGACT ACTGGGGCCA GGGAACCCTG GTCACCGTCT CCTCAGCCTC CACCAAGGGC
         CDR3 ──┤├─── JH4b ───┤├──────────── FR4 ────────────┤
                gamma-1 constant
      P   S   V   F   P   L   A
+1
361   CCATCGGTCT TCCCCCTGGC A
```

Figure 4

VLAB1withleader

```
                                    AB125                    leader
        M  E  A  P  A  Q  L  L  F  L  L  L  W  L  P  D  T  T  G
+1
 1      ATGGAAGCCC CAGCACAGCT TCTCTTCCTC CTGCTACTCT GGCTCCCAGA TACCACCGGA
                         AB11                                                      FR1
        E  I  V  L  T  Q  S  P  G  T  L  S  L  S  P  G  E  R  A  T
+1
 61     GAAATTGTGT TGACGCAGTC TCCAGGCACC CTGTCTTTGT CTCCAGGGGA AAGAGCCACC
           FR1                     CDR1                                            FR2
        L  S  C  R  A  S  Q  S  V  S  S  F  L  A  W  Y  Q  Q  K
+1
121     CTCTCCTGCA GGGCCAGTCA GAGTGTTAGC AGCAGCTTCT TAGCCTGGTA CCAGCAGAAA
                                                                              FR3
        P  G  Q  A  P  R  L  L  I  Y  G  A  S  S  R  A  T  G  I  P
+1
181     CCTGGCCAGG CTCCCAGGCT CCTCATCTAT GGTGCATCCA GCAGGGCCAC TGGCATCCCA
                     FR2                          CDR2                              FR3
        D  R  F  S  G  S  G  S  G  T  D  F  T  L  T  I  S  R  L  E
+1
241     GACAGGTTCA GTGGCAGTGG GTCTGGGACA GACTTCACTC TCACCATCAG CAGACTGGAG
                                                                             JK4
        P  E  D  F  A  V  Y  Y  C  Q  Q  Y  S  S  S  P  L  T  F  G
+1
301     CCTGAAGATT TTGCAGTGTA TTACTGTCAG CAGTATAGTA GTAGCCCGCT CACTTTCGGC
                  FR3                                CDR3                                    AB16
        G  G  T  K  V  E  I  K  R  T  V  A  A  P  S  V  F  I  F  P
+1
361     GGAGGGACCA AGGTGGAGAT CAAACGAACT GTGGCTGCAC CATCTGTCTT CATCTTCCCG
                JK4          FR4                        kappa constant
```

Figure 5

VHAB7noleader

```
              AB62
         Q  V  Q  L  V  Q  S  G  A  E  V  K  K  P  G  S  S  V  K  V
+1
  1      CAGGTTCAGC TGGTGCAGTC TGGGGCTGAG GTGAAGAAGC CTGGGTCCTC GGTGAAGGTC
                              FR1                                    FR2

S  C  K  A  S  G  T  F  S     R  Y  A  I  N  W  V  R  Q  A
+1                                         CDR1
 61      TCCTGCAAGG CTTCTGGAGG CACCTTCAGC AGATATGCTA TCAACTGGGT GCGACAGGCC
                   FR1                                         FR2

P  G  Q  G  L  E  W  M  G     R  I  I  P  I  L  D  I  A  D  Y
+1                                         CDR2
121      CCTGGACAAG GACTTGAGTG GATGGGAAGG ATCATCCCTA TCCTTGATAT AGCAGACTAC
                              FR2                                    FR3

A  Q  K  F  Q  D  R  V  T  I  T  A  D  K  S  T  N  T  A  Y
+1           CDR2
181      GCACAGAAGT TCCAGGACAG AGTCACGATT ACCGCGGACA AGTCCACGAA CACAGCCTAC
                              FR3                                    CDR3
                                                                     JH5b
         M  E  L  S  S  L  R  S  E  D  T  A  V  Y  Y  C  A  R  K  D
+1
241      ATGGAGCTGA GCAGCCTGAG ATCTGAGGAC ACGGCCGTGT ATTACTGTGC GAGAAAGGAC
                              FR3                                    FR4
                                                                     gamma-1 constant
         W  F  D  P  W  G  Q  G  T  L  V  T  V  S  S  A  S  T  K  G
+1          CDR3                       JH5b
301      TGGTTCGACC CCTGGGGCCA GGGAACCCTG GTCACCGTCT CCTCAGCCTC CACCAAGGGC
                              gamma-1 constant
                              AB90
         P  S  V  F  P  L  A
+1
361      CCATCGGTCT TCCCCCTGGC A
```

Figure 6

VLAB7wihtleader

```
                    leader
         AB125
      M  E  A  P  A  Q  L  L  F  L  L  L  W  L  P  D  I  T  G
+1
 1    ATGGAAGCCC CAGCACAGCT TCTCTTCCTC CTGCTACTCT GGCTCCCAGA TATCACCGGA
                                                              FR1

E  N  V  L  T  Q  S  P  G  T  L  S  L  S  P  G  E  R  A  T
+1
 61   GAAAATGTGT TGACGCAGTC TCCAGGCACC CTGTCTCTGT CTCCAGGGGA AAGAGCCACC
      FR1                                                         FR2

L  S  C  R  A  S  Q  S  G  S  S  S  Y  L  A  W  Y  Q  Q  K
+1
121   CTCTCCTGCA GGGCCAGTCA GAGTGGTAGC AGCAGCTACT TAGCCTGGTA CCAGCAGAAA
                           CDR1                                   FR3
              FR2

P  G  Q  A  P  R  L  L  I  Y  G  A  S  S  R  A  T  G  I  P
+1
181   CCTGGCCAGG CTCCCAGGCT CCTCATCTAT GGTGCATCCA GTAGGGCCAC TGGCATCCCA
                                      CDR2

D  R  F  S  G  S  G  S  G  T  D  F  T  L  T  I  S  R  L  E
+1
241   GACAGGTTCA GTGGCAGTGG GTCTGGGACA GACTTCACTC TCACCATCAG CAGACTGGAG
                          FR3                                     JK5

P  E  D  F  A  V  Y  Y  C  Q  Q  Y  G  S  S  P  I  T  F  G
+1
301   CCTGAAGATT TTGCAGTGTA TTACTGTCAG CAGTATGGTA GTTCACCGAT CACCTTCGGC
              FR4                  CDR3                           AB16
         JK5

Q  G  T  R  L  E  I  K  R  T  V  A  A  P  S  V  F  I  F  P
+1
361   CAAGGGACAC GACTGGAGAT TAAACGAACT GTGGCTGCAC CATCTGTCTT CATCTTCCCC
                                     kappa constant
```

Figure 8

VLAB11withleader leader
AB125

+1     M   E   A   P   A   Q   L   F   L   L   L   W   L   P   D   T   T   G
  1    ATGGAAGCCC CAGCACAGCT TCTCTTCCTC CTGCTACTCT GGCTCCCAGA TACCACCGGA
                                                   FR1

+1     E   I   V   L   T   Q   S   P   G   T   L   S   L   S   P   G   E   R   A   T
 61    GAAATTGTGT TGACGCAGTC TCCAGGCACC CTGTCTTTGT CTCCAGGGGA AAGAGCCACC
       FR1                                                            FR2

+1     L   S   C   R   A   S   Q   S   V   S   S   S   F   L   A   W   Y   Q   Q   K
121    CTCTCCTGCA GGGCCAGTCA GAGTGTTAGC AGCAGCTTCT TAGCCTGGTA CCAGCAGAAA
                                       CDR1

+1     P   G   Q   A   P   R   L   L   I   Y   G   A   S   S   R   A   T   G   I   P
181    CCTGGCCAGG CTCCCAGGCT CCTCATCTAT GGTGCATCCA GCAGGGCCAC TGGCATCCCA
              FR2                            CDR2                         FR3

+1     D   R   F   S   G   S   G   S   G   T   D   F   T   L   T   I   S   R   L   E
241    GACAGGTTCA GTGGCAGTGG GTCTGGGACA GACTTCACTC TCACCATCAG CAGACTGGAG
                                       FR3

+1     P   E   D   F   A   V   Y   Y   C   Q   Q   Y   S   S   S   P   L   T   F   G
301    CCTGAAGATT TTGCAGTGTA TTACTGTCAG CAGTATAGTA GCTCACCGCT CACTTTCGGC
                                                  CDR3                       JK4

+1     G   G   T   K   V   E   I   K   R   T   V   A   A   P   S   V   F   I   F   P
361    GGAGGGACCA AGGTGGAGAT CAAACGAACT GTGGCTGCAC CATCTGTCTT CATCTTCCCC
              FR4
       JK4                                kappa constant

VHAB12noleader

```
              AB63
         Q  V  Q  L  V  Q  S  G  A  E  V  K  K  P  G  S  S  V  K  V
+1                              FR1
  1   CAGGTGCAGC TGGTGCAGTC TGGGGCTGAG GTGAAGAAGC CTGGGTCCTC GGTGAAGGTC
                                                                  FR2

S  C  K  A  S  G  G  T  F  S     R  Y  I  I  N  W  V  R  Q  A
+1                                            CDR1
 61   TCCTGCAAGG CTTCTGGAGG CACCTTCAGC AGGTATATTA TCAACTGGGT GCGACAGGCC
           FR2

P  G  Q  G  L  E  W  M  G  R  I  I  P  I  L  G  V  E  N  Y
+1                                                        CDR2
121   CCTGGACAAG GGCTTGAGTG GATGGGAAGG ATCATCCCTA TCCTTGGTGT AGAAAACTAC
            CDR2                                                 FR3

A  Q  K  F  Q  G  R  V  T  I  T  A  D  K  S  T  S  T  A  Y
+1
181   GCACAGAAGT TCCAGGGCAG AGTCACGATT ACCGCGGACA AATCCACGAG CACAGCCTAC
                                               FR3                           CDR3
                                                                              JH4b
         M  E  L  S  S  L  R  S  E  D  T  A  V  Y  Y  C  A  R  K  D
+1
241   ATGGAGCTGA GCAGCCTGAG ATCTGAGGAC ACGGCCGTGT ATTACTGTGT GAGAAAGGAC
          CDR3                                                 FR4
                    JH4b                                                gamma-1constant
         W  F  D  Y  W  G  Q  G  T  L  V  T  V  S  S  A  S  T  K  G
+1
301   TGGTTTGATT ACTGGGGCCA GGGAACCCTG GTCACCGTCT CCTCAGCCTC CACCAAGGGC
         AB90
              gamma-1constant
         P  S  V  F  P  L  A
+1
361   CCATCGGTCT TCCCCCCTGGC A
```

Figure 16
A
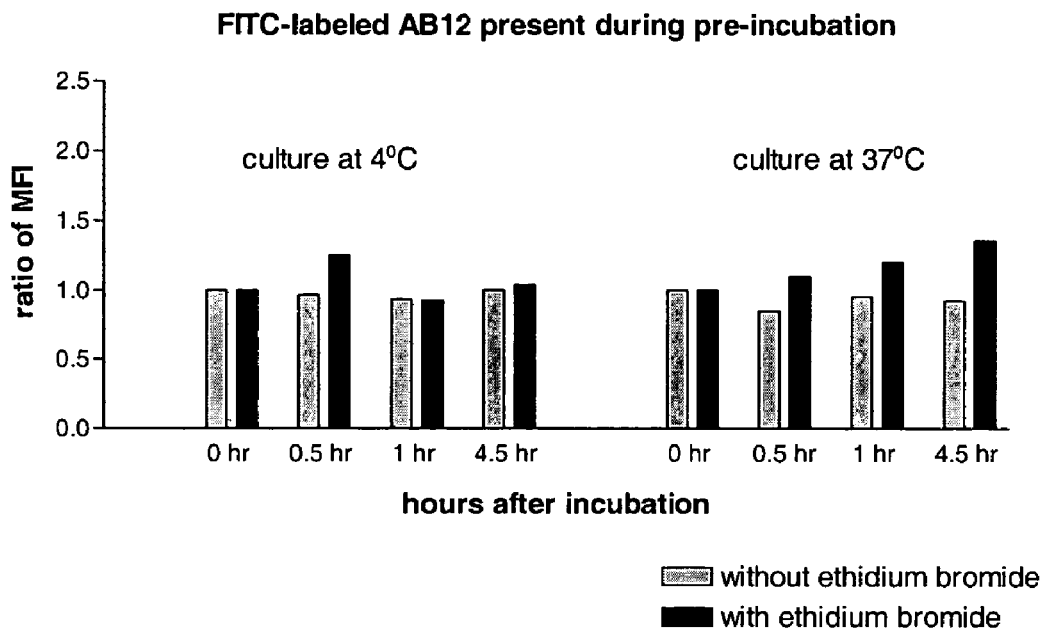
B
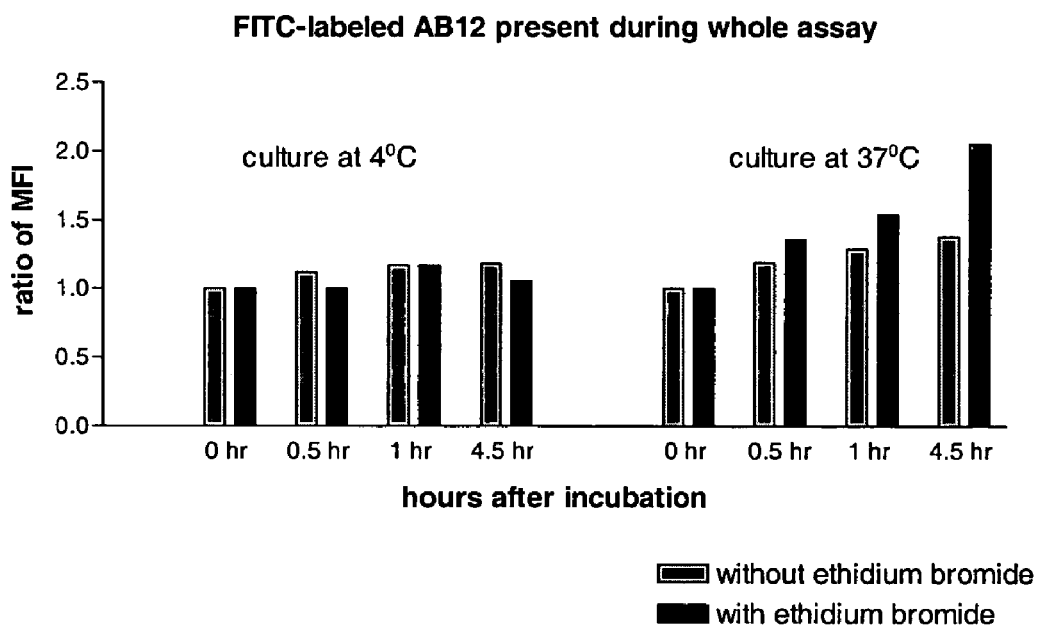

HUMAN MONOCLONAL ANTIBODIES AGAINST CD25

BACKGROUND OF THE INVENTION

The high affinity interleukin-2 receptor (IL-2R) is a heterotrimeric cell surface receptor composed of α, β and $γ_c$-polypeptide chains ($K_D$ $10^{-11}$ M). The 55 kDa α-chain, also known as IL-2Rα, CD25, p55, and Tac (T cell activation) antigen, is unique to the IL-2R. The β (CD122; P75) and $γ_c$ (CD132) chains are part of a cytokine receptor superfamily (hematopoietin receptors) and are functional components of other cytokine receptors, such as IL-15R (Waldmann (1993) *Immunol. Today* 14(6):264-70; Ellery et al. (2002) *Cytokine Growth Factor Rev.* 13(1): 27-40). The intermediate affinity receptor is a dimer composed of a β- and a $γ_c$-chain ($K_D$ $10^{-9}$ M) while the low affinity receptor consists of a monomeric α-subunit that has no signal transduction capacity ($K_D$ $10^{-8}$ M) (Waldmann (1993) *Immunol. Today* 14(6):264-70).

Resting T cells, B cells, and monocytes express few CD25 molecules. However, the receptor is rapidly transcribed and expressed upon activation (Ellery et al. (2002) *Cytokine Growth Factor Rev.* 13(1): 27-40; Morris et al. (2000) *Ann. Rheum. Dis.* 59 (Suppl. 1):i109-14). Cells expressing the high affinity IL-2R express CD25 (the CD25-subunit) in excess which leads to both high and low affinity IL-2 binding profiles (Waldmann et al. (1993) *Blood* 82(6):1701-12; de Jong et al. (1996) *J. Immunol.* 156(4):1339-48). CD25 is highly expressed by T cells in some autoimmune diseases, such as rheumatoid arthritis, scleroderma, and uveitis, as well as skin disorders, e.g., psoriasis and atopic dermatitis, and a variety of lymphoid neoplasms, e.g., T cell leukemia, and Hodgkin's disease (Waldmann (1993) *Immunol. Today* 14(6):264-70; Kuttler et al. (1999) *J. Mol. Med.* 77(1):226-9). In addition, CD25 expression is associated with allograft rejection and graft-versus-host responses (Jones et al. (2002) *J. Immunol.* 168(3):1123-1130; Anasetti et al. (1994) *Blood* 84(4): 1320-7).

Accordingly, CD25 is an important target for antibody-mediated therapy, for example, to reduce inflammation in autoimmune diseases, treat tumors, and prevent transplant rejection. However, while the results obtained and clinical experience to date clearly establish CD25 as a useful target for immunotherapy, they also show that currently available murine and chimeric antibodies do not constitute ideal therapeutic agents. Therefore, the need exists for further therapeutic antibodies against CD25 which are effective in preventing and/or treating a range of diseases involving cells expressing CD25.

SUMMARY OF THE INVENTION

The present invention provides novel antibody therapeutics for treating and/or preventing diseases associated with cells expressing CD25, including organ, tissue and cell transplant rejection, including allograft and xenograft rejection, graft-versus-host disease, autoimmune diseases, inflammatory and hyperproliferative skin disorders, and lymphoid neoplasms, among others. The antibodies encompassed by the invention are improved in that they are fully human and, thus, are potentially less immunogenic in patients. The antibodies are also advantageous based on their superior functional (e.g., therapeutic) properties.

As shown herein, the human antibodies of the invention bind to CD25 when tested by ELISA or flow cytometry.

The human antibodies of the invention typically bind to CD25 with a dissociation equilibrium constant ($K_D$) of approximately $10^{-8}$ M or less, such as $10^{-9}$ M or less, $10^{-10}$ M or less, or $10^{-11}$ M or even less when determined by surface plasmon resonance (SPR) technology in a BIAcore 3000 instrument using recombinant human IL-2Rα as the ligand and the antibody as the analyte. Such antibodies typically do not cross-react with related cell-surface antigens and do thus not inhibit their function.

Furthermore, the human antibodies of the present invention inhibit (e.g., block) the interaction of CD25 with its ligand, IL-2. For example, binding can be inhibited by at least about 10%, 20%, 30%, 40%, 50%, 60%, 70%, 80%, 90%, or 100%. Examples of cells which express CD25 and, the cellular function of which therefore, can be inhibited by the human antibodies of the present invention include, among others T cells, B cells and monocytes. For example, as shown herein, the human antibodies of the invention can inhibit IL-2 binding to CD25. Such inhibition of IL-2 binding to CD25 concomitantly inhibits various cellular mechanisms induced by IL-2 binding. As also shown herein, human antibodies of the invention can inhibit anti-CD3 antibody-induced T cell proliferation in a dose-dependent manner. As also shown herein, human antibodies of the invention can inhibit mixed lymphocyte reaction (MLR) in a dose-dependent manner. Inhibition of proliferation in such experiments may be monitored by a decrease in the accumulation of cell mass as measured in ELISA or by a decrease in the incorporation of BrdU in the cell's DNA.

Human antibodies of the invention include IgG1 (e.g., IgG1,κ and IgG1,λ), and IgG4 (e.g., IgG4,κ and IgG4,λ) antibodies. However, other antibody isotypes are also encompassed by the invention, including IgG2, IgG3, IgM, IgA1, IgA2, secretory IgA, IgD, and IgE. The antibodies can be whole antibodies or antigen-binding fragments thereof including, for example, Fab, Fab', F(ab)2, F(ab')$_2$, Fv, single chain Fv (scFv) fragments or bispecific antibodies. Furthermore, the antigen-binding fragments include binding-domain immunoglobulin fusion proteins comprising (i) a binding domain polypeptide (such as a heavy chain variable region or a light chain variable region) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. Such binding-domain immunoglobulin fusion proteins are further disclosed in US 2003/0118592 and US 2003/0133939. Particular human antibodies of the present invention include those referred to as AB1, AB7, AB11, and AB12, encoded by human heavy chain and human kappa light chain nucleic acids comprising nucleotide sequences in their variable regions as set forth in SEQ ID NOs:1, 5, 9, or 13 and SEQ ID NOs:3, 7, 11, or 15, respectively, and conservative sequence modifications thereof. In another embodiment, the human antibodies are characterized by having human heavy chain and human kappa light chain variable regions comprising the amino acid sequences as set forth in SEQ ID NOs:2, 6, 10, or 14 and SEQ ID NOs:4, 8, 12, or 16, respectively, and conservative sequence modifications thereof.

Other particular human antibodies of the invention include those which comprise a CDR (complementarity determining region) having a human heavy and light chain CDR1, a human heavy and light chain CDR2, and a human heavy and light chain CDR3, wherein (a) the human heavy chain CDR1, CDR2, and CDR3 comprise an amino acid sequence selected from the group consisting of the CDR1, CDR2, and CDR3 amino acid sequences shown in FIGS. 1-10 (SEQ ID NOs:17-19, 23-25, 29-31, or 35-37), and conservative sequence modifications thereof, and (b) the human light chain CDR1, CDR2, and CDR3 comprise an amino acid sequence selected from the group consisting of the CDR1, CDR2, and CDR3 amino acid sequences shown in FIGS. 1-10 (SEQ ID NOs: 20-22, 26-28, 32-34, or 38-40), and conservative sequence modifications thereof.

In another embodiment, human anti-CD25 antibodies of the present invention can be characterized by one or more of the following properties:

a) specificity for human CD25;

b) a binding affinity to CD25 corresponding to a $K_D$ of approximately $10^{-8}$ M or less, such as $10^{-9}$ M or less, $10^{-10}$ M or less, or $10^{-11}$ M or even less, when determined by surface plasmon resonance (SPR) technology in a BIAcore 3000 instrument using recombinant IL-2Rα as the ligand and the antibody as the analyte;

c) the ability to tolerize T cells;

d) the ability to block the interaction of CD25 with its ligand, IL-2;

e) the ability to eliminate T cells expressing CD25;

f) the ability to inhibit proliferation of T cells expressing CD25;

g) the ability to inhibit anti-CD3 antibody-induced T cell proliferation of peripheral blood mononuclear cells (PB-MCs);

h) the ability to block mixed lymphocyte reaction (MLR); and/or i) internalization of CD25 expressed on T cells.

The term "tolerized", as used herein, means that the T cells are not capable to react to an antigen after a rechallenge with this antigen.

Human anti-CD25 antibodies of the present invention can be derivatized, linked to or co-expressed with other binding specificities. In a particular embodiment, the antibodies are linked to one or more binding specificities for a different target antigen, such as an antigen on an effector cell.

Accordingly, the present invention also includes bispecific and multispecific molecules that bind to both human CD25 and to one or more different target antigens, such as CD3, CD4, IL-15R, membrane bound or receptor bound TNF-α, or membrane bound or receptor bound IL-15.

In another embodiment, human anti-CD25 antibodies of the invention are derivatized, linked to or co-expressed with another functional molecule, e.g., another peptide or protein (e.g., a Fab fragment). For example, the antibody can be functionally linked (e.g., by chemical coupling, genetic fusion, noncovalent association or otherwise) to one or more other molecular entities, such as another antibody (e.g., to produce a bispecific or a multispecific antibody), a cytotoxin, cellular ligand or antigen (e.g., to produce an immunoconjugate, such as an immunotoxin). The antibody also can be linked to other therapeutic moieties, e.g., a radioisotope, a small molecule anti-cancer drug, an anti-inflammatory agent, or an immunosuppressive agent. Accordingly, the present invention encompasses a large variety of antibody conjugates, bispecific and multispecific molecules, and fusion proteins, all of which bind to CD25-expressing cells and which can be used to target other molecules to such cells.

Human antibodies, immunoconjugates, bispecific and multispecific molecules and compositions of the present invention can be used in a variety of methods for inhibiting, killing and/or modulating activity and/or growth (e.g, proliferation) of cells expressing CD25. In one embodiment, the method includes inhibiting the proliferation of T cells expressing CD25. In another embodiment, the method includes inhibiting graft-versus-host responses, e.g., MLR. In still another embodiment, the method includes killing of cells expressing CD25 (e.g., by complement-mediated lysis or by linking the antibody to a cytotoxin). The cells are preferably killed or inhibited without killing or inhibiting the activity of cells which do not express CD25 but which may, for example, express a structurally related cell-surface antigen (i.e., without cross-reactivity to related but functionally distinct cell surface antigens). Cells expressing CD25 which can be inhibited or killed using the human antibodies of the invention include, for example, activated T lymphocytes, B lymphocytes, monocytes, macrophages, Kuppfer cells of the liver, and Langerhans' cells of the skin expressing CD25.

Accordingly, human antibodies of the present invention can be used to treat and/or prevent a variety of diseases and conditions wherein activated cells expressing CD25 play an active role in the pathogenesis by administering the antibodies to patients suffering from such diseases and conditions. Exemplary diseases that can be treated (e.g., ameliorated) or prevented include, but are not limited to, transplant rejection, including allograft and xenograft rejection, in patients undergoing or who have undergone organ or tissue transplantation, such as heart, lung, combined heart-lung, trachea, kidney, liver, pancreas, oesophagus, bowel, skin, limb, umbilical cord, stem cell, islet cell transplantation, etc. Antibodies of the present invention may thus be used as prophylactics in allograft and xenograft rejection, or be used to reverse, treat, or otherwise ameliorate acute allograft or xenograft rejection episodes.

Further diseases than can be treated include graft-versus-host disease, e.g. blood transfusion graft-versus-host disease and bone marrow graft-versus-host disease; inflammatory, immune or autoimmune diseases, such as rheumatoid arthritis, ankylosing spondylitis, psoriatic arthritis, type 1 diabetes, insulin-requiring type 2 diabetes, multiple sclerosis, systemic lupus erythematosus, myasthenia gravis, inflammatory bowel disease, Crohn's disease, ulcerative colitis, dermato-polymyositis, Sjögren's syndrome, arteritides, including giant cell arteritis, aplastic anemia, asthma, scleroderma, and uveitis; inflammatory or hyperproliferative skin disorders, e.g., psoriasis, including plaque psoriasis, pustulosis palmoplantaris (PPP), erosive lichen planus, pemphigus bullosa, epidermolysis bullosa, contact dermatitis and atopic dermatitis; and a variety of lymphoid neoplasms, e.g., T cell leukemia, Hodgkin's disease, hairy cell leukemia, or cutaneous T cell lymphoma, including mycosis fungoides, and Sezary's syndrome.

Further diseases that can be treated are malignancies wherein an inhibition of infiltrating CD25+ regulatory T cells is beneficial, such as gastric cancer, esophageal cancers, malignant melanoma, colorectal cancer, pancreas cancer, breast cancer, small cell lung cancer, non-small cell lung cancer, cervical cancer, ovarian cancer, and renal cell carcinoma;

hematological disorders, such as adult T cell leukemia/lymphoma, anaplastic large cell lymphoma, chronic lymphocytic leukemia (CLL)/small lymphocytic lymphoma (SLL), peripheral T cell lymphoma, and secondary amyloidosis;

skin disorders, such as pyoderma gangraenosum, granuloma annulare, allergic contact dermatitis, cicatricial pemphigoid, and herpes gestationis;

hepato-gastrointestinal disorders, such as collagen colitis, sclerosing cholangitis, chronic active hepatitis, lupoid hepatitis, autoimmune hepatitis, alcoholic hepatitis, chronic pancreatis, and acute pancreatitis;

cardiac disorders, such as myocarditis, and pericarditis;

vascular disorders, such as arteriosclerosis, giant cell arteritis/polymyalgia rheumatica, Takayasu arteritis, polyarteritis nodosa, Kawasaki syndrome, Wegener's granulomatosis, microscopic polyangiitis, Churg-Strauss syndrome, leukocytoclastic angiitis, and secondary leukocytoclastic vasculitis;

renal disorders, such as acute glomerulonphritis, chronic glomerulonephritis, minimal change nephritis, and Goodpasture's syndrome;

pulmonary disorders, such as alveolitis, bronchiolitis obliterans, silicosis, and berylliosis;

neurological disorders, such as multiple sclerosis, Alzheimer's disease, myasthenia gravis, chronic demyelinating polyneuropathy, and polyradiculitis including Guillain-Barré syndrome;

connective tissue disorders, such as relapsing polychondritis, sarcoidosis, systemic lupus erythematosus, CNS lupus, discoid lupus, lupus nephritis, chronic fatigue syndrome, and fibromyalgia;

endocrinological disorders, such as Graves' disease, Hashimoto's thyroiditis, and subacute thyroiditis; and viral infections, such as tropical spastic paraparesis.

In a particular embodiment of the invention, the subject being administered the antibody is additionally treated with one or more further therapeutic agents, such as immunosuppressive agents, anti-inflammatory agents, chemotherapeutic agents, cytotoxic agents or other agents which serve to enhance the therapeutic effect of the antibody.

In yet another aspect, the present invention provides a method for detecting in vitro or in vivo the presence of CD25 in a sample or individual, e.g., for diagnosing a CD25-related disease, preferably at an early stage. This can also be useful for monitoring the disease and effect of treatment with an anti-CD25 antibody and for determining and adjusting the dose of the antibody to be administered. In one embodiment, detecting the presence of CD25 in a sample is achieved by contacting a sample to be tested, optionally along with a control sample, with a human monoclonal antibody of the invention under conditions that allow for formation of a complex between the antibody and CD25. Complex formation is then detected (e.g., using ELISA, flow cytometry or Western blotting). When using a control sample along with the test sample, complex is detected in both samples and any statistically significant difference in the formation of complexes between the samples is indicative of the presence of CD25 in the test sample. The in vivo method can be performed using imaging technique such as PET (positron emission tomography) or SPECT (single photon emission computed tomography).

In a further aspect, the invention relates to anti-idiotypic antibodies which bind to the human monoclonal antibodies of the invention. These anti-idiotypic antibodies can be used as an immunodiagnostic tool to detect and quantify levels of human monoclonal antibodies against CD25 in laboratory or patient samples. This may be useful for examining pharmakokinetics of the anti-CD25 antibody or for determining and adjusting the dosage of the anti-CD25 antibody and for monitoring the disease and the effect of treatment in a patient.

Mouse anti-idiotypic antibodies can be made e.g. by immunizing Balb/C mice with the human monoclonal antibodies according to the invention, and generating hybridomas from spleens of these mice by fusion with myeloma cells such as NS1 using standard techniques.

In yet another aspect, the invention provides a transgenic non-human animal, such as a transgenic mouse, which express human monoclonal antibodies that bind to CD25. In a particular embodiment, the transgenic non-human animal is a transgenic mouse having a genome comprising a human heavy chain transgene or transchromosome and a human light chain transgene or transchromosome encoding all or a portion of an antibody of the invention. The transgenic non-human animal can be immunized with a purified or enriched preparation of CD25 antigen and/or cells expressing CD25. Preferably, the transgenic non-human animal, e.g., the transgenic mouse, is capable of producing multiple isotypes of human monoclonal antibodies to CD25 (e.g., IgG, IgA and/or IgM) by undergoing V-D-J recombination and isotype switching. Isotype switching may occur by, e.g., classical or non-classical isotype switching.

Accordingly, in yet another aspect, the invention provides isolated B cells from a transgenic non-human animal as described above, e.g., a transgenic mouse, which expresses human anti-CD25 antibodies. The isolated B cells can then be immortalized by fusion to an immortalized cell to provide a source (e.g., a hybridoma) of human anti-CD25 antibodies. Such hybridomas (i.e., which produce human anti-CD25 antibodies) are also included within the scope of the invention.

As exemplified herein, human antibodies of the invention can be obtained directly from hybridomas which express the antibody, or can be cloned (e.g., from hybridomas or phage which display antigen-binding portions of the antibodies) and recombinantly expressed in a host cell (e.g., a CHO (Chinese Hamster Ovary) cell, or a NS/0 cell). Further examples of host cells are microorganisms, such as *E. coli*, and fungi, such as yeast. Alternatively, they can be produced recombinantly in a transgenic non-human animal or plant. Accordingly, in another aspect, the present invention provides methods for producing human monoclonal antibodies which bind to human CD25. In one embodiment, the method includes immunizing a transgenic non-human animal, e.g., a transgenic mouse, as previously described (e.g., having a genome comprising a human heavy chain transgene and a human light chain transgene encoding all or a portion of an anti-CD25 antibody), with a purified or enriched preparation of human CD25 antigen and/or cells expressing human CD25. B cells (e.g., splenic B cells) of the animal are then obtained and fused with myeloma cells to form immortal, hybridoma cells that secrete human monoclonal antibodies against CD25.

In yet another aspect, the invention provides nucleic acid molecules encoding human anti-CD25 antibodies (e.g., variable regions thereof), as well as recombinant expression vectors which include the nucleic acids of the invention, and host cells transfected with such vectors. Methods of producing the antibodies by culturing these host cells are also encompassed by the invention. Particular nucleic acids provided by the invention comprise the nucleotide sequences shown in SEQ ID NOs:1, 5, 9, or 13 and SEQ ID NOs:3, 7, 11, or 15 encoding the heavy and light chains, respectively, of human anti-CD25 antibodies AB 1, AB7, AB11, and AB12.

Other features and advantages of the instant invention will be apparent from the following detailed description and claims.

BRIEF DESCRIPTION OF THE DRAWINGS

FIG. 1 shows the amino acid sequences of the light (kappa) chain VJ regions of human monoclonal antibodies AB1, AB7, AB11, and AB12 (SEQ ID NOs: 4 (residues 21-140), 8 (residues 21-140), 12 (residues 21-140), and 16 (residues 21-139), respectively) with CDRs designated (germ-line sequence disclosed as SEQ ID NO: 71).

FIG. 2 shows the amino acid sequences of the heavy chain VDJ regions of human monoclonal antibodies AB1, AB7, AB11, and AB12 (SEQ ID NOs: 2, 6, 10, and 14, respectively) with CDRs designated (germ-line sequence disclosed as SEQ ID NO: 72).

FIG. 3 shows the amino acid sequence (SEQ ID NO: 2) and the corresponding nucleotide sequence (SEQ ID NO: 1) of the heavy chain VDJ region of human monoclonal antibody AB 1 with CDRs designated.

FIG. 4 shows the amino acid sequence (SEQ ID NO: 4) and the corresponding nucleotide sequence (SEQ ID NO: 3) of the light (kappa) chain VJ region of human monoclonal antibody AB 1 with CDRs designated.

FIG. 5 shows the amino acid sequence (SEQ ID NO: 6) and the corresponding nucleotide sequence (SEQ ID NO: 5) of the heavy chain VDJ region of human monoclonal antibody AB7 with CDRs designated.

FIG. 6 shows the amino acid sequence (SEQ ID NO: 8) and the corresponding nucleotide sequence (SEQ ID NO: 7) of the light (kappa) chain VJ region of human monoclonal antibody AB7 with CDRs designated.

FIG. 8 shows the amino acid sequence (SEQ ID NO: 12) and the corresponding nucleotide sequence (SEQ ID NO: 11) of the light (kappa) chain VJ region of human monoclonal antibody AB11 with CDRs designated.

FIG. 9 shows the amino acid sequence (SEQ ID NO: 14) and the corresponding nucleotide sequence (SEQ ID NO: 13) of the heavy chain VDJ region of human monoclonal antibody AB12 with CDRs designated.

FIG. 15A shows the result for T cell blasts pre-incubated with FITC-labeled AB12 after 18 hours incubation at 37° C., and FIG. 15B shows the result for T cell blasts cultured for 18 hours at 37° C. in the presence of FITC-labeled AB12. For comparison FIG. 15C shows the result for T cell blasts cultured for 18 hours at 37° C. in the presence of FITC-labeled isotype control antibody (anti-KHL).

FIG. 16 shows the internalization of CD25 by FITC-labeled AB12 as measured by flow cytometry where a ratio of mean fluorescence intensity (MFI) of above 1 indicates that internalization has taken place. FIG. 16A shows the result for T cell blasts pre-incubated with FITC-labeled AB12 at 4° C. and 37° C., respectively, and FIG. 16B shows the result of T cell blasts cultured in the presence of FITC-labeled AB12 at 4° C. and 37° C., respectively.

DETAILED DESCRIPTION OF THE INVENTION

Figure 7:
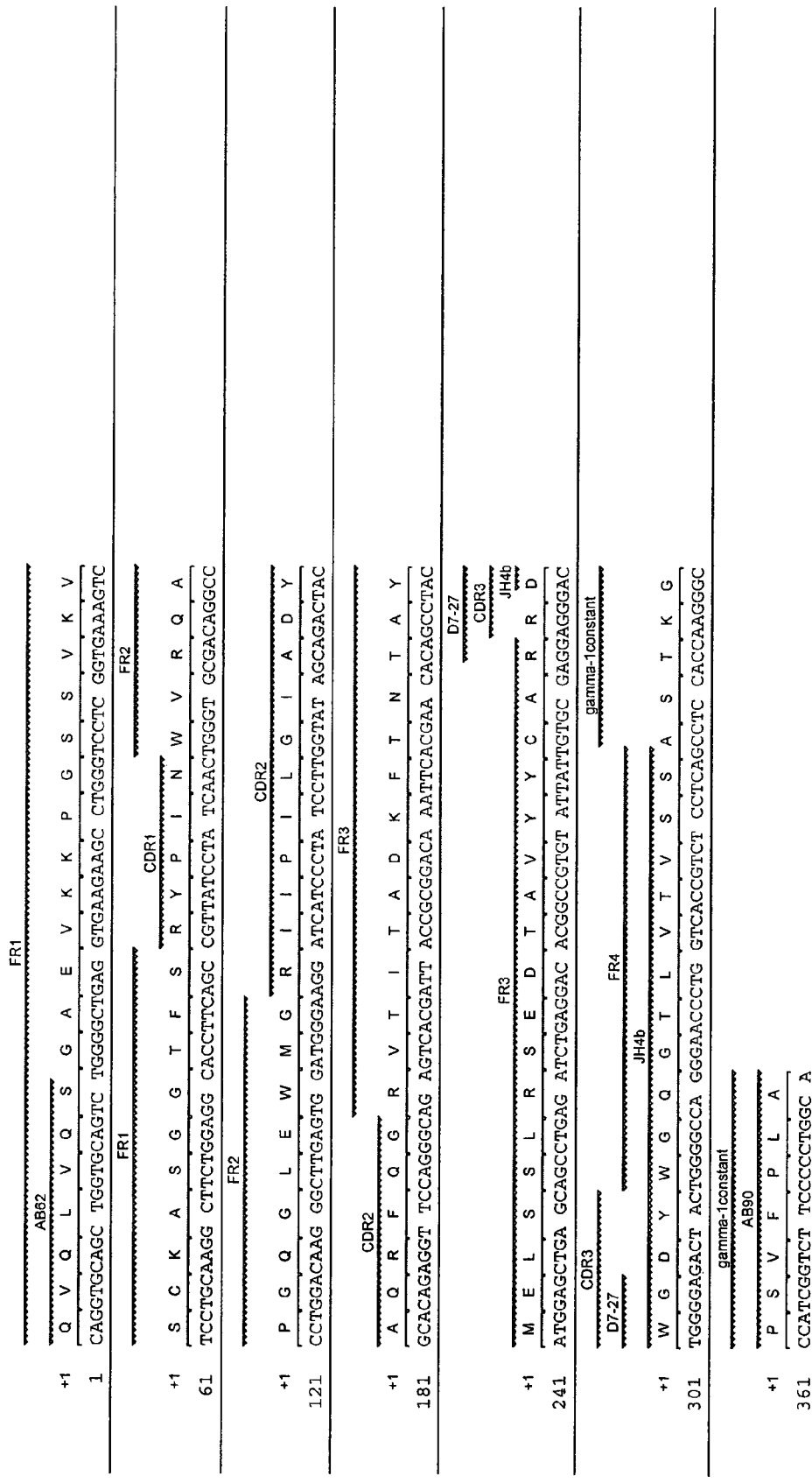
FIG. 7 shows the amino acid sequence (SEQ ID NO: 10) and the corresponding nucleotide sequence (SEQ ID NO: 9) of the heavy chain VDJ region of human monoclonal antibody AB11 with CDRs designated.
Figure 10:
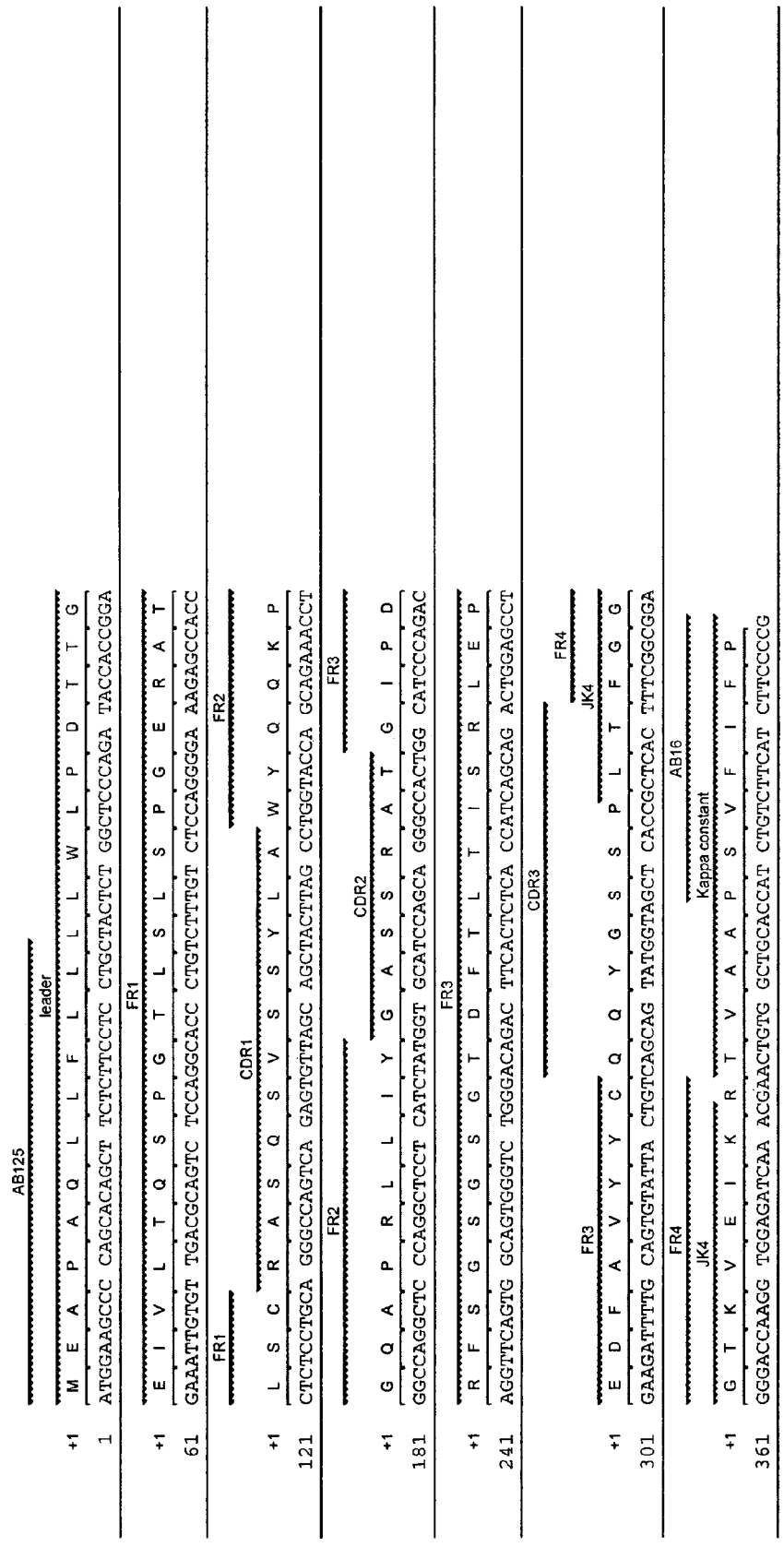
FIG. 10 shows the amino acid sequence (SEQ ID NO: 16) and the corresponding nucleotide sequence (SEQ ID NO: 15) of the light (kappa) chain VJ region of human monoclonal antibody AB12 with CDRs designated.

The present invention provides antibody-based therapies for treating and diagnosing a variety of disorders involving cells expressing CD25. Therapies of the invention employ isolated human monoclonal antibodies which specifically bind to an epitope present on CD25. Such antibodies include all known isotypes, e.g., IgA, IgG1-4, IgE, IgM, and IgD antibodies.

In one embodiment the antibody is an IgG1 antibody, more particularly an IgG1,κ or IgG1,λ isotype. In another embodiment the antibody is an IgG3 antibody, more particularly an IgG3,κ or IgG3,λ isotype. In yet another embodiment the antibody is an IgG4 antibody, more particularly an IgG4,κ or IgG4,λ isotype. In still another embodiment the antibody is an IgA1 or IgA2 antibody. In still a further embodiment the antibody is an IgM antibody.

In one embodiment, the human antibodies are produced in a nonhuman transgenic animal, e.g., a transgenic mouse, capable of producing multiple isotypes of human monoclonal antibodies to CD25 by undergoing V-D-J recombination and isotype switching. Such transgenic animal can also be a transgenic rabbit for producing polyclonal antibodies such as disclosed in US 2003/0017534. Accordingly, the invention also encompasses human polyclonal antibodies which specifically bind to CD25. Accordingly, aspects of the invention include not only antibodies, antibody fragments, and pharmaceutical compositions thereof, but also nonhuman transgenic animals, B cells, host cell transfectomas, and hybridomas which produce monoclonal antibodies. Methods of using the antibodies of the invention to block or inhibit cells expressing CD25 are also provided and are useful in the treatment of disorders associated with CD25. Methods of using the antibodies of the invention to detect a cell expressing CD25 are encompassed by the invention.

In order that the present invention may be more readily understood, certain terms are first defined. Additional definitions are set forth throughout the detailed description.

The terms "CD25" and "CD25 antigen" are used interchangeably herein, and include any variants, isoforms and species homologs of human CD25 which are naturally expressed by cells or are expressed on cells transfected with the CD25 gene. Synonyms of CD25, as recognized in the art, include CD25, p55, and Tac (T cell activation) antigen. Binding of an antibody of the invention to the CD25 antigen inhibits and/or blocks CD25 from binding to its ligand, IL-2, and, concomitantly, the resultant cellular function thereof. For example, in one embodiment, the human antibodies of the invention inhibit anti-CD3 antibody-induced T cell proliferation. In another embodiment, the human monoclonal antibodies inhibit MLR.

As used herein, the term "inhibits growth" (e.g., referring to cells) is intended to include any measurable decrease in the cell growth when contacted with an anti-CD25 antibody as compared to the growth of the same cells not in contact with an anti-CD25 antibody, e.g., the inhibition of growth of a cell culture by at least about 10%, 20%, 30%, 40%, 50%, 60%, 70%, 80%, 90%, 99%, or 100%.

As used herein, the terms "inhibits binding" and "blocks binding" (e.g., referring to inhibition/blocking of binding of IL-2 to CD25) are used interchangeably and encompass both partial and complete inhibition/blocking. The inhibition/blocking of binding of IL-2 to CD25 preferably reduces or alters the normal level or type of cell signaling that occurs when IL-2 binds to CD25 without inhibition or blocking. Inhibition and blocking are also intended to include any measurable decrease in the binding affinity of IL-2 to CD25 when in contact with an anti-CD25 antibody as compared to the ligand not in contact with an anti-CD25 antibody, e.g., the blocking of binding of IL-2 to CD25 by at least about 10%, 20%, 30%, 40%, 50%, 60%, 70%, 80%, 90%, 99%, or 100%.

The term "antibody" as referred to herein includes intact antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. Each light chain is comprised of a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., CD25). It has been shown that the antigen-binding function of an antibody can be performed by fragments of an intact or full-length antibody. Examples of binding fragments encompassed within the term "antigen-binding portion" of an antibody include (i) a Fab fragment, a monovalent fragment consisting of the $V_L, V_H, C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of a $V_L$ and $V_H$ domain; (v) a dAb fragment (Ward et al., (1989) Nature 341:544-546), which consists of a $V_H$ domain; (vi) an isolated complementarity determining region (CDR), and (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost by treatment with denaturing solvents.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell.

The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to CD25 and to other targets, such as Fc receptors on effector cells.

The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

The term "human antibody derivatives" refers to any modified form of the antibody, e.g., a conjugate of the antibody and another agent or antibody.

The term "human antibody", as used herein, is intended to include antibodies having variable and constant regions derived from human germline immunoglobulin sequences. The human antibodies of the invention may also include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic or transchromosomal nonhuman animal, e.g., a transgenic mouse, having a genome comprising a human heavy chain transgene and a light chain transgene, fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "transfectoma", as used herein, includes recombinant eukaryotic host cell expressing the antibody, such as CHO cells, NS/0 cells, HEK293 cells, plant cells, or fungi, including yeast cells.

As used herein, a "heterologous antibody" is defined in relation to the transgenic nonhuman organism producing such an antibody. This term refers to an antibody having an amino acid sequence or an encoding nucleic acid sequence corresponding to that found in an organism not consisting of the transgenic nonhuman animal, and generally from a species other than that of the transgenic nonhuman animal.

An "isolated antibody," as used herein, is intended to refer to an antibody which is substantially free of other antibodies having different antigenic specificities (e.g., an isolated antibody that specifically binds to CD25 is substantially free of antibodies that specifically bind antigens other than CD25). An isolated antibody that specifically binds to an epitope, isoform or variant of human CD25 may, however, have cross-reactivity to other related antigens, e.g., from other species (e.g., CD25 species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding" refers to antibody binding to a predetermined antigen. Typically, the antibody binds with an affinity corresponding to a $K_D$ of about $10^{-8}$ M or less, such as about $10^{-9}$ M or less, about $10^{-10}$ M or less, or about $10^{-11}$ M or even less when determined by surface plasmon resonance (SPR) technology in a BIAcore 3000 instrument using recombinant IL-2Rα as the ligand and the antibody as the analyte, and binds to the predetermined antigen with an affinity corresponding to a $K_D$ that is at least ten-fold lower, preferably at least 100 fold lower than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

The term "$k_d$" ($sec^{-1}$), as used herein, is intended to refer to the dissociation equilibrium rate constant of a particular antibody-antigen interaction. Said value is also referred to as the $k_{off}$ value.

The term "$k_a$" ($M^{-1} \times sec^{-1}$), as used herein, is intended to refer to the association equilibrium rate constant of a particular antibody-antigen interaction.

The term "$K_D$" (M), as used herein, is intended to refer to the dissociation equilibrium constant of a particular antibody-antigen interaction.

The term "$K_A$" ($M^{-1}$), as used herein, is intended to refer to the association equilibrium constant of a particular antibody-antigen interaction and is obtained by dividing the $k_a$ by the $k_d$.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $σ_μ$ and human $Σ_μ$ (δ-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a μ switch region, will be 5' (i.e., upstream) of the construct region to be deleted during the switch recombination. The "switch acceptor" region will be between the construct region to be deleted and the replacement constant region (e.g., γ, ε, etc.).

As used herein, "glycosylation pattern" is defined as the pattern of carbohydrate units that are covalently attached to a protein, more specifically to an immunoglobulin (antibody) protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding whole antibodies or antibody portions (e.g., $V_H$, $V_L$, CDR3) that bind to CD25, is intended to refer to a nucleic acid molecule in which the nucleotide sequences encoding the intact antibody or antibody portion are free of other nucleotide sequences encoding whole antibodies or antibody portions that bind antigens other than CD25, which other sequences may naturally flank the nucleic acid in human genomic DNA. In one embodiment, the human anti-CD25 antibody includes the heavy chain ($V_H$) and light chain ($V_L$) variable amino acid regions of AB1, AB7, AB11, or AB12 encoded by the nucleotide sequences shown in SEQ ID NOs: 1, 5, 9, or 13 and SEQ ID NOs: 3, 7, 11, or 15, respectively.

As disclosed and claimed herein, the sequences set forth in SEQ ID NOs: 1-40 include "conservative sequence modifications," i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into SEQ ID NOs: 1-40 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CD25 antibody is preferably replaced with another amino acid residue from the same side chain family.

The present invention also encompasses "derivatives" of the amino acid sequences as set forth in SEQ ID NOs: 2, 4, 6, 8, 10, 12, 14, 16, and 17-40 and conservative sequence modifications thereof, wherein one or more of the amino acid residues have been derivatised, e.g. by acylation or glycosylation, without significantly affecting or altering the binding characteristics of the antibody to CD25.

Furthermore, the present invention comprises antibodies in which one or more alterations have been made in the Fc region in order to change functional or pharmacokinetic properties of the antibodies. Such alterations may result in a decrease or increase of Clq binding and CDC or of FcγR binding and antibody-dependent cellular cytotoxicity (ADCC). Substitutions can for example be made in one or more of the amino acid residues 234, 235, 236, 237, 297, 318, 320, and 322 of the heavy chain constant region, thereby causing an alteration in an effector function while retaining binding to antigen as compared with the unmodified antibody, cf. U.S. Pat. No. 5,624,821 and U.S. Pat. No. 5,648,260. Further reference may be had to WO 00/42072 disclosing antibodies with altered Fc regions that increase ADCC, and WO 94/29351 disclosing antibodies having mutations in the N-terminal region of the CH2 domain that alter the ability of the antibodies to bind to FcRI and thereby decreases the ability of the antibodies to bind to Clq which in turn decreases the ability of the antibodies to fix complement. Furthermore, Shields et al., *J. Biol. Chem.* (2001) 276:6591-6604 teaches combination variants, e.g. T256A/S298A, S298A/E333A, and S298A/E333A/K334A, that improve FcγRIII binding.

The in vivo half-life of the antibodies can also be improved by modifying the salvage receptor epitope of the Ig constant domain or an Ig-like constant domain such that the molecule does not comprise an intact CH2 domain or an intact Ig Fc region, cf. U.S. Pat. No. 6,121,022 and U.S. Pat. No. 6,194,551. The in vivo half-life can furthermore be increased by making mutations in the Fc region, e.g. by substituting threonine for leucine at position 252, threonine for serine at position 254, or threonine for phenylalanine at position 256, cf. U.S. Pat. No. 6,277,375.

Furthermore, the glycosylation pattern of the antibodies can be modified in order to change the effector function of the antibodies. For example, the antibodies can be expressed in a transfectoma which does not add the fucose unit normally attached to the carbohydrate attached to Asn at position 297 of Fc in order to enhance the affinity of Fc for FcγRIII which in turn will result in an increased ADCC of the antibodies in the presence of NK cells, cf. Shield et al. (2002) *J. Biol. Chem.*, 277:26733. Furthermore, modification of galactosylation can be made in order to modify CDC. Further reference may be had to WO 99/54342 and Umana et al., *Nat. Biotechnol.* (1999) 17:176 disclosing a CHO cell line engineered to express GntIII resulting in the expression of monoclonal antibodies with altered glycoforms and improved ADCC activity.

Furthermore, the antibody fragments, e.g. Fab fragments; of the invention can be pegylated to increase the half-life. This can be carried out by pegylation reactions known in the art, as described, for example, in *Focus on Growth Factors* (1992) 3:4-10; EP 154 316 and EP 401 384.

Alternatively, in another embodiment, mutations can be introduced randomly along all or part of a anti-CD25 antibody coding sequence, such as by saturation mutagenesis, and the resulting modified anti-CD25 antibodies can be screened for binding activity.

Accordingly, antibodies encoded by the (heavy and light chain variable region) nucleotide sequences disclosed herein and/or containing the (heavy and light chain variable region) amino acid sequences disclosed herein (i.e., SEQ ID NOs: 2, 4, 6, 8, 10, 12, 14, 16, and 17-40) include substantially similar antibodies encoded by or containing similar sequences which have been conservatively modified. Further discussion as to how such substantially similar antibodies can be generated based on the partial (i.e., heavy and light chain variable regions) sequences disclosed herein as SEQ ID NOs: 2, 4, 6, 8, 10, 12, 14, 16, and 17-40 is provided below.

For nucleotide and amino acid sequences, the term "homology" indicates degree of identity between two nucleic acid or amino acid sequences when optimally aligned and compared with appropriate insertions or deletions. Alternatively, substantial homology exists when the DNA segments will hybridize under selective hybridization conditions, to the complement of the strand. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the internet at the website at gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*Comput. Appl. Biosci.*, 4:11-17 (1988)) which has been incorporated into the ALIGN program (version 2.0), using a PAM 120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5,or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score =100, wordlength =12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See the internet at the website of ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof, may be mutated in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription of regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells and NS/0 cells.

As used herein, the term "subject" includes any human or nonhuman animal. The term "nonhuman animal" includes all vertebrates, e.g., mammals and non-mammals, such as non-human primates, sheep, dog, cow, chickens, amphibians, reptiles, etc.

The term "transgenic, nonhuman animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-CD25 antibodies when immunized with CD25 antigen and/or cells expressing CD25. The human heavy and light chain transgene and/or transchromosome can be integrated into the chromosomal DNA of the mouse or maintained extrachromosomally. Such transgenic and transchromosomal mice (collectively referred to herein as "transgenic mice") are capable of producing multiple isotypes of human monoclonal antibodies to CD25 (e.g., IgG, IgA, IgM, IgD and/or IgE) by undergoing V-D-J recombination and isotype switching. Transgenic, nonhuman animal can also be used for production of a specific anti-CD25 antibody by introducing genes encoding such specific anti-CD25 antibody, for example by operatively linking the genes to a gene which is expressed in the milk of the animal. Various aspects of the invention are described in further detail in the following subsections.

I. Production of Human Antibodies to CD25

Human monoclonal antibodies of the invention can be produced by a variety of techniques, including conventional monoclonal antibody methodology, e.g., the standard somatic cell hybridization technique of Kohler and Milstein, *Nature* 256: 495 (1975). Although somatic cell hybridization procedures are preferred, in principle, other techniques for producing monoclonal antibody can be employed, e.g., viral or oncogenic transformation of B lymphocytes or phage display techniques using libraries of human antibody genes.

The preferred animal system for preparing hybridomas that secrete human monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

In a preferred embodiment, human monoclonal antibodies directed against CD25 can be generated using transgenic or transchromosomal mice carrying parts of the human immune system rather than the mouse system. These transgenic and transchromosomic mice include mice referred to herein as HuMAb mice, e.g. HCo7 and HCo12 mice, and KM mice, respectively, and are collectively referred to herein as "transgenic mice."

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) *Nature* 368 (6474):856-859). Accordingly, the mice exhibit reduced expression of mouse IgM or κ light chain and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol. Vol.* 13:65-93, and Harding, F. and Lonberg, N. (1995) *Ann. N.Y. Acad. Sci* 764:536-546). The preparation of HuMAb mice is described in detail in Taylor, L. et al. (1992) *Nucleic Acids Research* 20:6287-6295; Chen, J. et al (1993) *International Immunology* 5:647-656; Tuaillon et al. (1994) *J. Immunol.* 152:2912-2920; Lonberg N. et al., (1994) *Nature* 368(6474):856-859; Lonberg, N. (1994) *Handbook of Experimental Pharmacology* 113:49-101; Taylor, L. et al. (1994) International Immunology 6:579-591; Lonberg, N. and Huszar, D. (1995) *Intern. Rev. Immunol. Vol.* 13:65-93; Harding, F. and Lonberg, N. (1995) *Ann. N.Y. Acad. Sci* 764:536-546; Fishwild, D. et al. (1996) *Nature Biotechnology* 14:845-851. See further, U.S. Pat. No. 5,545,806; U.S. Pat. No. 5,569,825; U.S. Pat. No. 5,625,126; U.S. Pat. No. 5,633,425; U.S. Pat. No. 5,789,650; U.S. Pat. No. 5,877,397; U.S. Pat. No. 5,661,016; U.S. Pat. No. 5,814,318; U.S. Pat. No. 5,874,299; and U.S. Pat. No. 5,770,429; all to Lonberg and Kay, as well as U.S. Pat. No. 5,545,807 to Surani et al.; WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al. (1993) *EMBO J.* 12: 821-830), a CMD disruption in their endogenous heavy chain genes (as described in Example 1 of WO 01/14424), a KCo5 human kappa light chain transgene (as described in Fishwild et al. (1996) *Nature Biotechnology* 14:845-851), and a HCo7 human heavy chain transgene (as described in U.S. Pat. No. 5,770,429).

The HCo12 mice have a JKD disruption in their endogenous light chain (kappa) genes (as described in Chen et al. (1993) *EMBO J.* 12: 821-830), a CMD disruption in their endogenous heavy chain genes (as described in Example 1 of WO 01/14424 by Korman et al.), a KCo5 human kappa light chain transgene (as described in Fishwild et al. (1996) *Nature Biotechnology* 14:845-851), and a HCo12 human heavy chain transgene (as described in Example 2 of WO 01/14424 by Korman et al.). In the KM mouse strain, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of WO 01/09187. This mouse strain carries a human kappa light chain transgene, KCo5, as described in Fishwild et al. (1996) *Nature Biotechnology* 14:845-851. This mouse strain also carries a human heavy chain transchromosome composed of chromosome 14 fragment hCF (SC20) as described in WO $O_2$/43478.

Immunizations

To generate fully human monoclonal antibodies to CD25, transgenic or transchromosomal mice containing human immunoglobulin genes (e.g., HCo12, HCo7 or KM mice) can be immunized with an enriched preparation of CD25 antigen, recombinant CD25, and/or cells expressing CD25, as described, for example, by Lonberg et al. (1994), supra; Fishwild et al. (1996), *supra*, and WO 98/24884. Alternatively, mice can be immunized with DNA encoding human CD25. Preferably the mice will be 6-16 weeks of age upon the first infusion. For example, an enriched preparation of the CD25 antigen or recombinant CD25 antigen can be used to immunize the HuMAb mice intraperitoneally. In the event that immunizations using a purified or enriched preparation of the CD25 antigen do not result in antibodies, mice can also be immunized with cells expressing CD25, e.g., a cell line, to promote immune responses.

Cumulative experience with various antigens has shown that the HuMAb transgenic mice respond best when initially immunized intraperitoneally (IP) or subcutaneously (SC) with CD25 expressing cells in complete or incomplete Freund's adjuvant, followed by IP immunizations (up to a total of 10) with CD25 expressing cells, e.g. in phosphate buffered saline (PBS). The immune response can be monitored over the course of the immunization protocol with serum samples being obtained by retroorbital bleeds. The serum can be screened by FACS analysis (as described below), and mice with sufficient titers of anti-CD25 human immunoglobulin can be used for fusions. Mice can be boosted intravenously with CD25 expressing cells before, for example 3 and 2 days before, sacrifice and removal of the spleen and lymph nodes.

Generation of Hybridomas Producing Human Monoclonal Antibodies to CD25

To generate hybridomas producing human monoclonal antibodies to human CD25, splenocytes and lymph node cells from immunized mice can be isolated and fused to an appropriate immortalized cell line, such as a mouse myeloma cell line. The resulting hybridomas can then be screened for the production of antigen-specific antibodies. For example, single cell suspensions of splenic lymphocytes from immunized mice can be fused to SP2/0-Ag14 myeloma cells (ATCC, CRL 1581) with 50% PEG (w/v). Cells can be plated at approximately 1×10⁵ per well in flat bottom microtiter plate, followed by a two-week incubation in selective medium containing besides usual reagents 10% fetal Clone Serum, 5 Origen Hybridoma Cloning Factor (IGEN) and 1X HAT (Sigma). After approximately two weeks, cells can be cultured in medium in which the HAT is replaced with HT (Sigma). Individual wells can then be screened by ELISA for human kappa-light chain containing antibodies and by FACS analysis using CD25 expressing cells for CD25 specificity. Once extensive hybridoma growth occurs, the clones can be screened for IgG production, usually after 7-10 days. The antibody-secreting hybridomas can be replated, screened again, and if still positive for human IgG, anti-CD25 monoclonal antibodies can be subcloned at least twice by limiting dilution. The stable subclones can then be cultured in vitro to generate antibody in tissue culture medium for characterization.

Generation of Transfectomas Producing Human Monoclonal Antibodies to CD25

Human antibodies of the invention also can be produced in a host cell transfectoma using, for example, a combination of recombinant DNA techniques and gene transfection methods as is well known in the art (Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or β-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include CHO cells (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS/0 myeloma cells, COS cells, HEK293 cells and SP2 cells. In particular for use with NS/0 myeloma cells, another preferred expression system is the GS (glutamine synthetase) gene expression system disclosed in WO 87/04462, WO 89/01036 and EP 338 841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Further Recombinant Means for Producing Human Monoclonal Antibodies to CD25

Alternatively the cloned antibody genes can be expressed in other expression systems, including prokaryotic cells, such as microorganisms, e.g. *E. coli* for the production of scFv antibodies, algi, as well as insect cells. Furthermore, the antibodies can be produced in transgenic nonhuman animals, such as in milk from sheep and rabbits or eggs from hens, or in transgenic plants. See e.g. Verma, R., et al. (1998). Antibody engineering: Comparison of bacterial, yeast, insect and mammalian expression systems. *J. Immunol. Meth.* 216:165-181; Pollock, et al. (1999). Transgenic milk as a method for the production of recombinant antibodies. *J. Immunol. Meth.* 231:147-157; and Fischer, R., et al. (1999). Molecular farming of recombinant antibodies in plants. *Biol. Chem.* 380:825-839.

Use of Partial Antibody Sequences to Express Intact Antibodies

Antibodies interact with target antigens predominantly through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; and Queen, C. et al. (1989) *Proc. Natl. Acad. Sci. U.S.A.* 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody which contains mutations throughout the variable gene but typically clustered in the CDRs. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see WO 99/45962). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak (1991) *J. Biol. Chem.* 266:19867-19870); and HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site of the gamma heavy chain) in the PCR amplification to generate fragments that can easily be cloned into the expression vector constructs.

The reconstructed heavy and light chain variable regions are then combined with cloned promoter, leader sequence, translation initiation, constant region, 3' untranslated, polyadenylation, and transcription termination sequences to form expression vector constructs. The heavy and light chain expression constructs can be combined into a single vector, co-transfected, serially transfected, or separately transfected into host cells which are then fused to form a host cell expressing both chains.

A similar procedure may be followed to graft novel antigen-specificity into an existing mature antibody. Preferably, an acceptor antibody is chosen which originates from the same variable germ-line gene as the CDR-donor antibody. One or more CDRs from the donor antibody are then transferred using the techniques described above.

Exemplary plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human IgG1,κ or IgG4,κ antibodies. Similar plasmids can be constructed for expression of other heavy chain isotypes, or for expression of antibodies comprising lambda light chains.

Accordingly, in another embodiment, the invention provides various methods for preparing human anti-CD25 antibodies. In one embodiment, the method involves:

preparing an antibody comprising (1) human heavy chain framework regions and human heavy chain CDRs, wherein at least one of the human heavy chain CDRs comprises an amino acid sequence selected from the amino acid sequences of CDRs shown in FIGS. 1-10 (or corresponding amino acid residues in SEQ ID NOs:17-19, 23-25, 29-31, or 35-37); and (2) human light chain framework regions and human light chain CDRs, wherein at least one of the human light chain CDRs comprises an amino acid sequence selected from the amino acid sequences of CDRs shown in FIGS. 1-10 (or corresponding amino acid residues in SEQ ID NOs: 20-22, 26-28, 32-34, or 38-40); wherein the antibody retains the ability to bind to CD25.

The ability of the antibody to bind to CD25 can then be determined using standard binding assays, such as those set forth in the Examples (e.g., a FACS analysis).

Since it is well known in the art that antibody heavy and light chain CDR3 domains play a particularly important role in the binding specificity/affinity of an antibody for an antigen, the recombinant antibodies of the invention prepared as set forth above preferably comprise the heavy and light chain CDR3s of AB1, AB7, AB11, or AB12. The antibodies further can comprise the CDR2s of AB1, AB7, AB11, or AB12. The antibodies further can comprise the CDRs of AB1, AB7, AB11, or AB12. Accordingly, the invention further provides anti-CD25 antibodies comprising: (1) human heavy chain framework regions, a human heavy chain CDR1 region, a human heavy chain CDR2 region, and a human heavy chain CDR3 region, wherein the human heavy chain CDR3 region is the CDR3 of AB1, AB7, AB11, or AB12 as shown in FIGS. 1-10 (or corresponding amino acid residues as shown in SEQ ID NOs: 19, 25, 31, or 37); and (2) human light chain framework regions, a human light chain CDR1 region, a human light chain CDR2 region, and a human light chain CDR3 region, wherein the human light chain CDR3 region is the CDR3 of AB11, AB7, AB11, or AB12 as shown in FIGS. 1-10 (or corresponding amino acid residues as shown in SEQ ID NOs:22, 28, 34, or 40), wherein the antibody binds to CD25. The antibody may further comprise the heavy chain CDR2 and/or the light chain CDR2 of AB1, AB7, AB11, or AB12. The antibody may further comprise the heavy chain CDR1 and/or the light chain CDR1 of AB1, AB7, AB11, or AB12.

Preferably, the CDR1, 2, and/or 3 of the engineered antibodies described above comprise the exact amino acid sequence(s) as those of AB1, AB7, AB11, or AB12 disclosed herein. However, the ordinarily skilled artisan will appreciate that some deviation from the exact CDR sequences of AB1, AB7, AB11, or AB12 may be possible while still retaining the ability of the antibody to bind CD25 effectively (e.g., conservative substitutions). Accordingly, in another embodiment, the engineered antibody may be composed of one or more CDRs that are, for example, 90%, 95%, 98% or 99.5% homologous to one or more CDRs of AB1, AB7, AB111, or AB12.

In addition or alternative to simply binding CD25, engineered antibodies such as those described above may be selected for their retention of other functional properties of antibodies of the invention, such as:

(1) high affinity binding to CD25;
(2) inhibition or blocking of CD25 binding to IL-2;
(3) elimination of T cells expressing CD25;
(4) tolerization of T cells;
(5) inhibition of proliferation of T cells expressing CD25;
(6) inhibition of anti-CD3 antibody-induced T cell proliferation of PBMCs;
(7) inhibition of MLR; and/or
(8) internalization of CD25 expressed on T cells.

Characterization of Binding of Human Monoclonal Antibodies to CD25

Human anti-CD25 antibodies of the invention can be isolated and characterized in a number of different ways. For example, selected hybridomas can be grown in suitable flasks for monoclonal antibody purification. Supernatants can then be filtered and concentrated before affinity chromatography with protein A-sepharose (for IgG1 isotype antibodies) (Pharmacia, Piscataway, N.J.) or anti-human IgG coated sepharose or protein G-sepharose in case of IgG3 isotype antibodies.

Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected human anti-CD25 monoclonal antibodies bind to unique epitopes, site-directed or multi-site directed mutagenesis can be used.

To determine the isotype of purified antibodies, isotype ELISAs can be performed. Wells of microtiter plates can be coated with 10 μg/ml of anti-human Ig overnight at 4° C. After blocking with 5% BSA (bovine serum albumin), the plates are reacted with 10 μg/ml of monoclonal antibodies or purified isotype controls, at ambient temperature for two hours. The wells can then be reacted with either human IgG1, IgG2, IgG3 or IgG4, IgE, IgA1, IgA2, or human IgM-specific alkaline phosphatase-conjugated probes. After washing, the plates are developed with pNPP substrate (1 mg/ml) and analyzed by OD at 405 nm.

In order to demonstrate the presence of anti-CD25 antibodies in sera of immunized mice or the binding of monoclonal antibodies to live cells expressing the CD25, flow cytometry can be used. Briefly, cell lines expressing CD25 (grown under standard growth conditions) are mixed with various concentrations of monoclonal antibodies in PBS containing 0.1% BSA and 0.02% sodium-azide, and incubated at 4° C. for 30 minutes. After washing, the cells are reacted with fluorescein-labeled anti-human IgG antibody under the same conditions as the primary antibody staining. The samples can be analyzed by flow cytometry with a flow cytometer (e.g., Becton Dickinson FACS instrument) using light and side scatter properties to gate on single, living cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-CD25 human IgGs can be further tested for reactivity with CD25 antigen by Western blotting. Briefly, cell extracts from cells expressing CD25 can be prepared and subjected to sodium dodecyl sulfate (SDS) polyacrylamide gel electrophoresis. After electrophoresis, the separated antigens will be transferred to nitrocellulose membranes, blocked with 20% non-fat milk, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Inhibition of Activity of Cells Expressing CD25

In addition to binding specifically to CD25, human monoclonal anti-CD25 antibodies can be tested for their ability to inhibit various activities of cells, such as T cell and other lymphocytes, expressing CD25. For example, T cell proliferation assays can be carried out using known techniques. In one technique, human PBMCs are diluted in a suitable medium and then stimulated with, for example, an anti-CD3 antibody, before adding varying concentrations of the experimental antibodies to determine the effect they have on T cell proliferation. T cell proliferation of purified T cells can also be assessed in the presence of anti-CD3 and anti-CD28 monoclonal antibodies.

Assays for MLR can also be conducted using known techniques. For example, PBMCs from a first donor can be irradiated and mixed with PBMCs from a second donor. Varying concentrations of antibody can then be added to the cells, followed by measurement of the MLR response.

II. Production of Transgenic Non-human Animals Which Generate Human Monoclonal Anti-CD25 Antibodies In yet another aspect, the invention provides transgenic and transchromosomal nonhuman animals, such as transgenic or transchromosomal mice, which are capable of expressing human antibodies that specifically bind to CD25. In a particular embodiment, the invention provides a transgenic or transchromosomal mouse having a genome comprising a human heavy chain transgene, such that the mouse produces human anti-CD25 antibodies when immunized with cells expressing CD25. The human heavy chain transgene can be integrated into the chromosomal DNA of the mouse, as is the case for transgenic, e.g., HuMAb mice, as described in detail herein and exemplified. Alternatively, the human heavy chain transgene can be maintained extrachromosomally, as is the case for transchromosomal (e.g., KM) mice as described in WO $O_2$/43478. Such transgenic and transchromosomal animals are capable of producing multiple isotypes of human monoclonal antibodies to CD25 (e.g., IgG, IgA and/or IgE) by undergoing V-D-J/V-J recombination and isotype switching. The design of a transgenic or transchromosomal nonhuman animal that responds to foreign antigen stimulation with a heterologous antibody repertoire, requires that the heterologous immunoglobulin transgenes contained within the transgenic animal function correctly throughout the pathway of B cell development. This includes, for example, isotype switching of the heterologous heavy chain transgene. Accordingly, transgenes are constructed so that isotype switching can be induced and one or more of the following characteristics of antibody genes: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology*, 2nd edition (1989), Paul William E., ed. Raven Press, N.Y.

In certain embodiments, the transgenic or transchromosomal nonhuman animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al., *Nucl. Acids Res.* 15:7305-7316 (1991); Sideras et al., *Intl. Immunol.* 1:631-642 (1989)). For each of the foregoing transgenic animals, functionally rearranged heterologous heavy and light chain immunoglobulin transgenes are found in a significant fraction of the B cells of the transgenic animal (at least 10%).

The transgenes used to generate the transgenic nonhuman animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic animal in that they are derived from, or correspond to, DNA encoding immunoglobulin heavy and light chain gene segments from a species not consisting of the transgenic nonhuman animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic animal when exposed to CD25 antigen.

In an alternate embodiment, the transgenes comprise an unrearranged "mini-locus". Such transgenes typically comprise a substantial portion of the C, D, and J segments as well as a subset of the V gene segments. In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the nonhuman animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

Preferred transgenic and transchromosomal nonhuman animals, e.g., mice, will exhibit immunoglobulin production with a significant repertoire, ideally substantially similar to that of a human after adjusting for volume.

The repertoire will ideally approximate that shown in a human when adjusted for volume, usually with a diversity at least about 10% as great, preferably 25 to 50% or more. Generally, at least about a thousand different immunoglobulins (ideally IgG), preferably $10^4$ to $10^6$ or more, will be produced, depending on the number of different V, J and D regions introduced into the mouse genome and driven by the additional diversity generated by V(-D-)J gene segment rearrangements and random nucleotide additions at the joining regions. Typically, the immunoglobulins will exhibit an affinity ($K_D$) for preselected antigens of below $10^{-8}$ M, such as of below $10^{-9}$ M, $10^{-10}$ M or $10^{-11}$ M or even lower.

Transgenic and transchromosomal nonhuman animals, e.g., mice, as described above can be immunized with, for example, cells expressing CD25. Alternatively, the transgenic animals can be immunized with DNA encoding human CD25. The animals will then produce B cells which undergo class-switching via switch recombination (cis-switching) and express immunoglobulins reactive with CD25. The immunoglobulins will be human antibodies (also referred to as "human sequence antibodies"), wherein the heavy and light chain polypeptides are encoded by human transgene sequences, which may include sequences derived by somatic mutation and V region recombinatorial joints, as well as germline-encoded sequences; these human antibodies can be referred to as being substantially identical to a polypeptide sequence encoded by a human $V_L$ and $J_L$ or $V_H$, $D_H$ and $J_H$ gene segments, even though other non-germline sequences may be present as a result of somatic mutation and differential V-J and V-D-J recombination joints. The variable regions of each antibody chain are typically at least 80 percent similar to human germline V, and J gene segments, and, in the case of heavy chains, human germline V, D, and J gene segments; frequently at least 85 percent similar to human germline sequences present on the transgene; often 90 or 95 percent or more similar to human germline sequences present on the transgene. However, since non-germline sequences are introduced by somatic mutation and VJ and VDJ joining, the human sequence antibodies will frequently have some variable region sequences which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

Another aspect of the invention includes B cells derived from transgenic or transchromosomal nonhuman animals as described herein. The B cells can be used to generate hybridomas expressing human monoclonal antibodies which bind with high affinity (e.g., a dissociation equilibrium constant ($K_D$) of lower than $10^{-8}$ M) to human CD25. Thus, in another embodiment, the invention provides a hybridoma which produces a human antibody having an affinity ($K_D$) of below $10^{-8}$ M, such as of below $10^{-9}$ M, $10^{-10}$ M or $10^{-11}$ M or even lower when determined by scatchard analysis of CD25 expressing cells using a radio-actively labeled monoclonal antibody or by determination of the half-maximal binding concentration using FACS analysis, or by analysis using surface plasmon resonance as measured on a BIAcore instrument.

Herein the monoclonal antibody comprises a human sequence light chain composed of (1) a light chain variable region having a polypeptide sequence which is substantially identical to a polypeptide sequence encoded by a human $V_L$ gene segment and a human $J_L$ segment, and (2) a light chain constant region encoded by a human $C_L$ gene segment; and a human sequence heavy chain composed of a (1) a heavy chain variable region having a polypeptide sequence which is substantially identical to a polypeptide sequence encoded by a human $V_H$ gene segment, a D region, and a human $J_H$ segment, and (2) a constant region encoded by a human $C_H$ gene segment. It should be noted that human D genes may be substantially altered by recombination and somatic mutation events such that the original human germ-line sequence may not be readily recognized.

The development of high affinity human monoclonal antibodies against CD25 can be facilitated by a method for expanding the repertoire of human variable region gene segments in a transgenic nonhuman animal having a genome comprising an integrated human immunoglobulin transgene, said method comprising introducing into the genome a V gene transgene comprising V region gene segments which are not present in said integrated human immunoglobulin transgene. Often, the V region transgene is a yeast artificial chromosome (YAC) comprising a portion of a human $V_H$ or $V_L$ ($V_K$) gene segment array, as may naturally occur in a human genome or as may be spliced together separately by recombinant methods, which may include out-of-order or omitted V gene segments. Often at least five or more functional V gene segments are contained on the YAC. In this variation, it is possible to make a transgenic animal produced by the V repertoire expansion method, wherein the animal expresses an immunoglobulin chain comprising a variable region sequence encoded by a V region gene segment present on the V region transgene and a C region encoded on the human Ig transgene. By means of the V repertoire expansion method, transgenic animals having at least 5 distinct V genes can be generated; as can animals containing at least about 24 V genes or more. Some V gene segments may be non-functional (e.g., pseudogenes and the like); these segments may be retained or may be selectively deleted by recombinant methods available to the skilled artisan, if desired.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a nonhuman animal germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast is no longer necessary (i.e., prior to introduction into a mouse ES cell or mouse prozygote). Methods of propagating the trait of human sequence immunoglobulin expression, include breeding a transgenic animal having the human Ig transgene(s), and optionally also having a functional YAC having an expanded V segment repertoire. Both $V_H$ and $V_L$ gene segments may be present on the YAC. The transgenic animal may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal of the invention, other embodiments are contemplated which have been classified in three categories:

I. Transgenic animals containing an unrearranged heavy and rearranged light chain immunoglobulin transgene;

II. Transgenic animals containing an unrearranged heavy and unrearranged light chain immunoglobulin transgene; and III. Transgenic animal containing rearranged heavy and an unrearranged light chain immunoglobulin transgene.

Of these categories of transgenic animal, the preferred order of preference is as follows II>I>III where the endogenous light chain genes (or at least the κ gene) have been knocked out by homologous recombination (or other method) and I>I>III where the endogenous light chain genes have not been knocked out and must be dominated by allelic exclusion.

III. Bispecific/Multispecific Molecules which Bind to CD25

In yet another embodiment of the invention, human monoclonal antibodies to CD25 can be derivatized or linked to another functional molecule, e.g., another peptide or protein (e.g., an Fab' fragment) to generate a bispecific or multispecific molecule which binds to multiple binding sites or target epitopes. For example, an antibody of the invention can be functionally linked (e.g., by chemical coupling, genetic fusion, noncovalent association or otherwise) to one or more other binding molecules, such as another antibody, peptide or binding mimetic.

Accordingly, the present invention includes bispecific and multispecific molecules comprising at least one first binding specificity for CD25 and a second binding specificity for a second target epitope. In a particular embodiment of the invention, the second target epitope is CD3, CD4, IL-15R, membrane bound or receptor bound TNF-α, or membrane bound or receptor bound IL-15. In another embodiment, the second target epitope is an Fc receptor, e.g., human FcγRI (CD64) or human FcαRI (CD89), or a T cell receptor. Therefore, the invention includes bispecific and multispecific molecules capable of binding both to FcγR, FcαR or FcεR expressing effector cells (e.g., monocytes, macrophages or polymorphonuclear cells (PMNs)), and to target cells expressing CD25. These bispecific and multispecific molecules target CD25 expressing cells to effector cell and, like the human monoclonal antibodies of the invention, trigger Fc receptor-mediated effector cell activities, such as phagocytosis of a CD25 expressing cells, ADCC, cytokine release, or generation of superoxide anion.

Bispecific and multispecific molecules of the invention can further include a third binding specificity, in addition to an anti-Fc binding specificity and the anti-CD25 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, a functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T cell (e.g. via CD2, CD3, CD8, CD28, CD4, CD40, ICAM-1 or other immune cell that results in an increased immune response against the target cell).

In one embodiment, the bispecific and multispecific molecules of the invention comprise as a binding specificity at least one antibody, including, e.g., an Fab, Fab', F(ab')$_2$, Fv, or scFv. The antibody may also be a light chain or heavy chain dimer, or any minimal fragment thereof such as a Fv or a single chain construct as described in Ladner et al. U.S. Pat. No. 4,946,778. The antibody may also be a binding-domain immunoglobulin fusion protein as disclosed in US 2003/0118592 and US 2003/0133939.

In one embodiment, the binding specificity for an Fc receptor is provided by a human monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fcγ receptor is a human high affinity FcγRI.

The production and characterization of these preferred monoclonal antibodies are described by Fanger et al. in WO 88/00052 and in U.S. Pat. No. 4,954,617. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are MAb 22, MAb 32, MAb 44, MAb 62 and MAb 197. In other embodiments, the anti-FcγRI antibody is a humanized form of MAb 22 (H22). The production and characterization of the H22 antibody is described in Graziano, R. F. et al. (1995) *J. Immunol.* 155 (10): 4996-5002 and WO 94/10332. The H22 antibody producing cell line was deposited at the American Type Culture Collection on Nov. 4, 1992 under the designation HA022CL1 and has the accession No. CRL 11177.

In still other preferred embodiments, the binding specificity for an Fc receptor is provided by an antibody that binds to a human IgA receptor, e.g., FcαRI (CD89), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al., 1992, *J. Immunol.* 148:1764).

FcαRI and FcγRI are preferred trigger receptors for use in the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); and (4) mediating enhanced antigen presentation of antigens, including self-antigens, targeted to them.

An "effector cell specific antibody" as used herein refers to an antibody or functional antibody fragment that binds the Fc receptor of effector cells. Preferred antibodies for use in the subject invention bind the Fc receptor of effector cells at a site which is not bound by endogenous immunoglobulin.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing ADCC, e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of FcγRI has been found to be up-regulated by interferon gamma (IFN-γ). This enhanced expression increases the cytotoxic activity of FcγRI-bearing cells against targets. An effector cell can phagocytose or lyse a target antigen or a target cell.

"Target cell" shall mean any cell in a subject (e.g., a human or animal) that can be targeted by a composition (e.g., a human monoclonal antibody, a bispecific or a multispecific molecule) of the invention. In preferred embodiments, the target cell is a cell expressing or overexpressing CD25. Cells expressing CD25 typically include activated T cells, monocytes and B cells.

Bispecific and multispecific molecules of the present invention can be made using chemical techniques (see e.g., D. M. Kranz et al. (1981) Proc. Natl. Acad. Sci. USA 78:5807), "polydoma" techniques (See U.S. Pat. No. 4,474,893, to Reading), or recombinant DNA techniques.

In particular, bispecific and multispecific molecules of the present invention can be prepared by conjugating the constituent binding specificities, e.g., the anti-FcR and anti-CD25 binding specificities, using methods known in the art and described in the examples provided herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis-(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohexane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described by Paulus, Behring Ins. Mitt. (1985) No. 78,118-132; Brennan et al., Science (1985) 229:81-83, and Glennie et al,. J. Immunol. (1987) 139:2367-2375. Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a MAb×MAb, MAb×Fab, Fab×F(ab')$_2$ or ligand×Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing such bi- and multi-specific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), BIAcore analysis, or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a γ counter or a scintillation counter or by autoradiography.

IV. Immunoconjugates

In another aspect of the invention, human anti-CD25 antibodies are conjugated to a therapeutic moiety, such as a cytotoxin, a drug (e.g., an immunosuppressant) or a radioisotope. Such conjugates are referred to herein as "immunoconjugates". Immunoconjugates which include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Suitable therapeutic agents for forming immunoconjugates of the invention include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cisplatin (cis-dichlorodiamine platinum (II) (DDP)), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other examples of therapeutic cytotoxins that can be conjugated to an antibody of the invention include calicheamicins and duocarmycins.

Antibodies of the present invention also can be conjugated to a radioisotope, e.g., iodine-131, yttrium-90 or indium-111, to generate cytotoxic radiopharmaceuticals for treating a CD25-related disorder, such as a cancer. The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin A, or diphtheria toxin, or an agent active at the cell surface, such as phospholipase enzymes, e.g. phospholipase C.

Techniques for conjugating such therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985); and Thorpe et al., "The Preparation And Cytotoxic Properties Of Antibody-Toxin Conjugates", *Immunol. Rev.*, 62:119-58 (1982).

In a further embodiment, the human monoclonal antibodies according to the invention are attached to a linker-chelator, (e.g. tiuxetan), which allows for the antibody to be conjugated to a radioisotope.

V. Pharmaceutical Compositions

In another aspect, the present invention provides compositions, including, pharmaceutical compositions, containing one or a combination of human monoclonal antibodies of the present invention. The compositions may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

Compositions of the invention also can be administered in combination therapy, i.e., combined with other agents relevant for the disease or condition to be treated. For example, the combination therapy can include a composition of the present invention with at least one immunosuppressive agent, at least one anti-inflammatory agent, at least one psoriasis agent, or at least one chemotherapeutic agent.

In one embodiment, such therapeutic agents include one or more immunosuppressive agents, such as cyclosporine, azathioprine, mycophenolic acid, mycophenolate mofetil, corticosteroids, such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, etc.

In a further embodiment, the compositions of the invention are administered in combination with two or more immunosuppressive agents, such as prednisone and cyclosporine; prednisone, cyclosporine and azathioprine; or prednisone, cyclosporine and mycophenolate mofetil.

In a further embodiment, such therapeutic agents include one or more anti-inflammatory agents, such as a steroidal drug or a NSAID (nonsteroidal anti-inflammatory drug). Preferred agents include, for example, aspirin and other salicylates, Cox-2 inhibitors, such as rofecoxib and celecoxib, NSAIDs such as ibuprofen, fenoprofen, naproxen, sulindac, diclofenac, piroxicam, ketoprofen, diflunisal, nabumetone, etodolac, oxaprozin, and indomethacin.

In another embodiment, such therapeutic agents include one or more DMARDs, such as methotrexate, hydroxychloroquine, sulfasalazine, pyrimidine synthesis inhibitors, e.g. leflunomide, IL-1 receptor blocking agents, e.g. anakinra, and TNF-α blocking agents, e.g. etanercept, infliximab and adalimumab. Further suitable DMARDs are anti-IL-6R antibodies, CTLA4Ig, and anti-IL-15 antibodies.

In another embodiment, such therapeutic agents include one or more agents for treating inflammatory or hyperproliferative skin disorders, such as topical medications, including coal tar, A vitamin, anthralin, calcipotrien, tarazotene, and corticosteroids, oral or injected medications, such as corticosteroids, methotrexate, retinoids, e.g. acicretin, cyclosporine, etanercept, alefacept, efaluzimab, 6-thioguanine, mycophenolate mofetil, tacrolimus (FK-506), and hydroxyurea. Other examples are CTLA4Ig and infliximab. Other treatments may include exposure to sunlight or phototherapy, including UVB (broad-band and narrow-band ultraviolet B), UVA (ultraviolet A) and PUVA (psoralen methoxalen plus ultraviolet A).

In a further embodiment, the compositions of the invention are administered in combination with two or more of the above therapies, such as methotrexate+phototherapy (PUVA or UVA); methotrexate+acitretin; acitretin+phototherapy (PUVA or UVA); methotrexate+acitretin+phototherapy (PUVA or UVB); hydroxyurea+phototherapy (PUVA or UVB); hydroxyurea+acitretin; cyclosporine+methotrexate; or calcipotrien+phototherapy (UVB).

In yet another embodiment, such therapeutic agents include one or more chemotherapeutics, such as doxorubicin, cisplatin, bleomycin, carmustine, cyclophosphamide, vindesine, vincristine, and chlorambucil.

In yet another embodiment, the present antibodies may be administered in conjunction with radiotherapy and/or bone marrow transplantation.

In still another embodiment, the present antibodies may be administered in combination with other antibodies, e.g. other immunosuppressive human monoclonal antibodies, such as antibodies binding to p75 of the IL-2 receptor, or antibodies binding to e.g. MHC, CD2, CD3, CD4, CD7, CD28, B7, CD40, CD45, IFN-γ, TNF-α, IL-4, IL-5, IL-6R, IL-7, IL-8, IL-10, CD11a, CD20 or CD58, or antibodies binding to their ligands; or in combination with other immunomodulatory compounds, e.g., soluble IL-15R or IL-10.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous intramuscular, subcutaneous, parenteral, spinal or epidermal administration (e.g., by injection or infusion).

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous acids and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Compositions of the present invention, including pharmaceutical (therapeutic) compositions, can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., *Sustained and Controlled Release Drug Delivery Systems*, J. R. Robinson, ed., Marcel Dekker, Inc., New York, 1978.

To administer compositions of the invention by certain routes of administration, it may be necessary to coat the compound with, or co-administer the compound with, a material to prevent its inactivation. For example, the compound may be administered to a subject in an appropriate carrier, for example, liposomes, or a diluent.

Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions can be brought about by including in the composition an agent that delays absorption, for example, monostearate salts and gelatin.

In one embodiment the human monoclonal antibodies of the invention are administered in crystalline form by subcutaneous injection, cf. Yang et al. (2003) *PNAS,* 100(12):6934-6939.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Therapeutic compositions of the present invention can be formulated for particular routes of administration, such as oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01% to about 99% of active ingredient, preferably from about 0.1% to about 70%, most preferably from about 1% to about 30%.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. While it is possible for a compound of the present invention to be administered alone, it is preferable to administer the compound as a pharmaceutical formulation (composition). The dosage can be determined or adjusted by measuring the amount of circulating monoclonal anti-CD25 antibodies at different time points following administration in a biological sample by making use of anti-idiotypic antibodies targeting the anti-CD25 antibodies.

Human monoclonal antibodies of the invention may be administered for prevention of transplant rejection by induction treatment, i.e. as a prophylactic short-term therapy for single or multiple administration before transplantation and in the very early phase following transplantation, e.g. shortly before the transplantation and up to 3 months after transplantation.

In one embodiment, monoclonal antibodies of the invention may e.g. be administered for prevention of transplant rejection in total dosages of about 20 to 100 mg e.g. administered as 15 or 20 mg intravenous infusions with the first dose given pre-operatively and the subsequent doses given within the first 10 days post-operatively. Alternatively, the dosages may be administered by bolus injections. In another embodiment monoclonal antibodies of the invention may be administered for prevention of transplant rejection in a dosage of from 0.5-1.5 mg/kg intravenously, every other week for up to five doses with the first dose given pre-operatively. Such administration may be combined with immunosuppressive therapy, e.g. steroids, such as prednisone or methylprednisolone, and cyclosporine; steroids, such as prednisone or methylprednisolone, cyclosporine and azathioprine; or steroids, such as prednisone or methylprednisolone, cyclosporine and mycophenolate mofetil. Administration of the human antibodies may advantageously be steroid sparing or result in rapid steroid withdrawal.

In another embodiment, human monoclonal antibodies of the invention may be administered for treating or preventing transplant rejection by a two-dose intravenous infusion regimen (about 20 mg per dose on the day of transplantation and about 20 mg at day 4 post-transplantation). Such administration may be combined with immunosuppressive therapy, e.g. as disclosed above. For example, 1 g mycophenolate mofetil may be administered orally before surgery, and 500 mg methylprednisolone at the time of anesthesia induction. Cyclosporine may be introduced on the second day after transplantation and mycophenolate mofetil may be continued at 1 g after transplantation. Steroids may be tapered to prednisone 20 mg orally on the fourth postoperative day.

In yet another embodiment, human monoclonal antibodies of the invention may be administered for treating or preventing transplant rejection by a two-dose induction therapy the first 1 mg/kg dose given 1 hour before surgery and the second dose 4 days after transplantation. Such administration may be combined with immunosuppressive therapy, e.g. as disclosed above.

Human monoclonal antibodies of the invention may be administered for prevention of transplant rejection by long-term therapy, e.g. by administration of a dose in the range of 10 to 150 mg, such as 20 to 40 mg, on a weekly basis or monthly basis, for example 3 to 8 weekly administrations, optionally followed by one or more monthly administrations. By long-term therapy cyclosporine maintenance therapy may be reduced or avoided.

Therapeutic antibody compositions can be administered with medical devices known in the art. For example, in a preferred embodiment, a therapeutic composition of the invention can be administered with a needleless hypodermic injection device, such as the devices disclosed in U.S. Pat. No. 5,399,163; U.S. Pat. No. 5,383,851; U.S. Pat. No. 5,312,335; U.S. Pat. No. 5,064,413; U.S. Pat. No. 4,941,880; U.S. Pat. No. 4,790,824; or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, human monoclonal antibodies of the invention can be formulated to ensure proper distribution in vivo. For example, the blood-brain barrier (BBB) excludes many highly hydrophilic compounds. To ensure that the therapeutic compounds of the invention can cross the BBB (if desired), they can be formulated, for example, in liposomes. For methods of manufacturing liposomes, see, e.g., U.S. Pat. No. 4,522,811; U.S. Pat. No. 5,374,548; and U.S. Pat. No. 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the desired area, e.g., the site of inflammation or infection, or the site of a tumor. The composition must be fluid to the extent that easy syringability exists. It must be stable under the conditions of manufacture and storage and must be preserved against the contaminating action of microorganisms such as bacteria and fungi.

The efficient dosages and the dosage regimens for the human monoclonal antibodies of the invention depend on the disease or condition to be treated and can be determined by the persons skilled in the art.

A "therapeutically effective dosage" for preventing transplant rejection preferably will reduce the number and severity of early transplant rejection episodes.

A "therapeutically effective dosage" for rheumatoid arthritis preferably will result in an ACR20 Preliminary Definition of Improvement in the patients, more preferred in an ACR50 Preliminary Definition of Improvement and even more preferred in an ARC70 Preliminary Definition of Improvement.

ACR20 Preliminary Definition of Improvement is defined as: $\geq$20% improvement in: Tender Joint Count (TJC) and Swollen Joint Count (SJC) and $\geq$20% improvement in 3 of following 5 assessments: Patient Pain Assessment (VAS), Patient Global assessment (VAS), Physician Global Assessment (VAS), Patient Self-Assessed Disability (HAQ), and Acute Phase Reactant (CRP or ESR).

ACR50 and ACR70 are defined in the same way with $\geq$50% and $\geq$70% improvements, respectively. For further details see Felson et al. in American College of Rheumatology Preliminary Definition of Improvement in Rheumatoid Arthritis; *Arthritis Rheumatism* (1995) 38:727-735.

Alternatively, a therapeutically effective dosage for rheumatoid arthritis can be measured by DAS (disease activity score), including DAS28 and, more preferably, DAS56, as defined by EULAR.

A "therapeutically effective dosage" for psoriasis preferably will result in a PASI50, more preferably a PASI75, and even more preferably a PASI90 in the patients or a reduction in the overall psoriasis evaluation comparing impression of improvement after drug treatment when compared to pre-treatment condition. PASI (Psoriasis Area and Severity Index) is a score system used for evaluation of the area and severity of the disease. PASI50 is defined as $\geq$50% improvement of the score. In the same way, PASI75 and PASI90 are defined as $\geq$75% and $\geq$90% improvement of the score, respectively.

A "therapeutically effective dosage" for tumor therapy can be measured by objective tumor responses which can either be complete or partial. A complete response (CR) is defined as no clinical, radiological or other evidence of disease. A partial response (PR) results from a reduction in aggregate tumor size of greater than 50%. Median time to progression is a measure that characterizes the durability of the objective tumor response.

A "therapeutically effective dosage" for tumor therapy can also be measured by its ability to stabilize the progression of disease. The ability of a compound to inhibit cancer can be evaluated in an animal model system predictive of efficacy in human tumors. Alternatively, this property of a composition can be evaluated by examining the ability of the compound to inhibit cell growth or to induce apoptosis by in vitro assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

VI. Uses and Methods of the Invention

Human antibodies of the present invention, as well as derivatives/conjugates and compositions thereof, have numerous utilities involving the treatment of CD25 mediated disorders or disorders involving cells expressing CD25.

In one embodiment, human antibodies of the present invention can be administered in vivo to a subject to block or inhibit binding of CD25 to its ligand (IL-2). This, in turn, can be used to prevent or inhibit a variety of diseases associated with CD25 bearing cells.

Exemplary diseases that can be treated (e.g., ameliorated) or prevented include, but are not limited to, transplant rejection, including allograft and xenograft rejection, in patients undergoing or who have undergone organ or tissue transplantation, such as heart, lung, combined heart-lung, trachea, kidney, liver, pancreas, oesophagus, bowel, skin, limb transplantation, umbilical cord transplantation, stem cell transplantation, islet cell transplantation, etc. Such patients includes adults but can also be pediatric patients.

Antibodies of the present invention may thus be used in prophylaxis of allograft and xenograft rejection or be used to reverse, treat, or otherwise ameliorate acute allograft or zenograft rejection episodes.

Further diseases that can be treated include graft-versus-host disease, e.g. blood transfusion graft-versus-host disease and bone marrow graft-versus-host disease; inflammatory, immune or autoimmune diseases, such as rheumatoid arthritis, ankylosing spondylitis, psoriatic arthritis, type 1 diabetes, insulin-requiring type 2 diabetes, multiple sclerosis, systemic lupus erythematosus, myasthenia gravis, inflammatory bowel disease, Crohn's disease, ulcerative colitis, dermato-polymyositis, Sjögren's syndrome, arteritides, including giant cell arteritis, aplastic anemia, asthma, scleroderma, and uveitis; inflammatory or hyperproliferative skin disorders, e.g., psoriasis, including plaque psoriasis, pustulosis palmoplantaris (PPP), erosive lichen planus, pemphigus bullosa, epidermolysis bullosa, contact dermatitis and atopic dermatitis; and a variety of lymphoid neoplasms, e.g., T cell leukemia, Hodgkin's disease, hairy cell leukemia, or cutaneous T cell lymphoma, including mycosis fungoides and Sezary's syndrome.

Further diseases that can be treated are
malignancies wherein an inhibition of infiltrating CD25+ regulatory T cells is beneficial, such as gastric cancer, esophageal cancers, malignant melanoma, colorectal cancer, pancreas cancer, breast cancer, small cell lung cancer, non-small cell lung cancer, cervical cancer, ovarian cancer, and renal cell carcinoma;

hematological disorders, such as adult T cell leukemia/lymphoma, anaplastic large cell lymphoma, chronic lymphocytic leukemia (CLL)/small lymphocytic lymphoma (SLL), peripheral T cell lymphoma, and secondary amyloidosis;

skin disorders, such as pyoderma gangraenosum, granuloma annulare, allergic contact dermatitis, cicatricial pemphigoid, and herpes gestationis;

hepato-gastrointestinal disorders, such as collagen colitis, sclerosing cholangitis, chronic active hepatitis, lupoid hepatitis, autoimmune hepatitis, alcoholic hepatitis, chronic pancreatis, and acute pancreatitis;

cardiac disorders, such as myocarditis, and pericarditis;

vascular disorders, such as arteriosclerosis, giant cell arteritis/polymyalgia rheumatica, Takayasu arteritis, polyarteritis nodosa, Kawasaki syndrome, Wegener's granulomatosis, microscopic polyangiitis, Churg-Strauss syndrome, leukocytoclastic angiitis, and secondary leukocytoclastic vasculitis;

renal disorders, such as acute glomerulonphritis, chronic glomerulonphritis, minimal change nephritis, and Goodpasture's syndrome;

pulmonary disorders, such as alveolitis, bronchiolitis obliterans, silicosis, and berylliosis;

neurological disorders, such as multiple sclerosis, Alzheimer's disease, myasthenia gravis, chronic demyelinating polyneuropathy, and polyradiculitis including Guillain-Barré syndrome;

connective tissue disorders, such as relapsing polychondritis, sarcoidosis, systemic lupus erythematosus, CNS lupus, discoid lupus, lupus nephritis, chronic fatigue syndrome, and fibromyalgia;

endocrinological disorders, such as Graves' disease, Hashimoto's thyroiditis, and subacute thyroiditis; and viral infections, such as tropical spastic paraparesis.

Suitable routes of administering the antibody compositions (e.g., human antibodies and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

The antibody can be administered alone or along with another therapeutic agent, such as an immunosuppressive agent, an anti-inflammatory agent, an agent for treating inflammatory or hyperproliferative skin disorders, a chemotherapeutic agent, or a cytotoxin which acts in conjunction with or synergistically with the antibody composition to treat or prevent diseases associated with cells expressing CD25, especially activated T cells.

As previously described, human anti-CD25 antibodies of the invention can be co-administered with one or other more therapeutic agents, e.g., an immunosuppressive agent or an anti-inflammatory agent to increase the overall anti-inflammatory effect. The antibody can be linked to the agent (as an immunocomplex) or can be administered separate from the agent. In the latter case (separate administration), the antibody can be administered before, after or concurrently with the agent.

Also within the scope of the present invention are kits comprising the antibody compositions of the invention (e.g., human antibodies and immunoconjugates) and instructions for use. The kit can further contain one ore more additional agents, such as an immunosuppressive agent, or one or more additional human antibodies of the invention.

Accordingly, patients treated with antibody compositions of the invention can be additionally administered (prior to, simultaneously with, or following administration of a human antibody of the invention) with another therapeutic agent, such as an immunosuppressive agent, an anti-inflammatory agent, an agent for treating inflammatory or hyperproliferative skin disorders, or a chemotherapeutic agent, which enhances or augments the therapeutic effect of the human antibodies.

In yet another embodiment, immunoconjugates of the invention can be used to target compounds (e.g., therapeutic agents, labels, cytotoxins, immunosuppressants, etc.) to cells which have CD25 bound to their surface by linking such compounds to the antibody. Thus, the invention also provides methods for localizing ex vivo or in vitro cells expressing CD25 (e.g., with a detectable label, such as a radioisotope, a fluorescent compound, an enzyme, or an enzyme co-factor). In another embodiment, the invention provides methods for killing cells which have CD25 bound to their surface by administering immunotoxins of the present invention.

In a further embodiment, the antibodies of the invention can be used in vivo or in vitro for diagnosing diseases wherein activated cells expressing CD25 play an active role in the pathogenesis by detecting levels of CD25, or levels of cells which contain CD25 on their membrane surface. This can be achieved, for example, by contacting a sample to be tested, optionally along with a control sample, with the human antibody under conditions that allow for formation of a complex between the antibody and CD25. Complex formation is then detected (e.g., using an ELISA). When using a control sample along with the test sample, complex is detected in both samples and any statistically significant difference in the formation of complexes between the samples is indicative of the presence of CD25 in the test sample.

The present invention is further illustrated by the following examples which should not be construed as further limiting.

EXAMPLES

Example 1

Production of Human Antibodies Against CD25

Antigen: A transfectant cell line expressing cell surface CD25 was developed to use as a reagent for immunizing HuMAb mice and characterizing anti-CD25 antibodies. This cell line was a CHO cell line engineered to express the extracellular domains of CD25 coupled to the transmembrane domain of platelet-derived growth factor receptor. The CD25 sequences were amplified from cDNA prepared from HUT102 cells and the platelet derived-growth factor receptor sequences were obtained from the pDISPLAY vector (Invitrogen Corporation). An expression construct encoding the fusion protein was engineered in an expression vector. The CHO transfectant cell line underwent 2 rounds of methotrexate amplification in 5 nM and 50 nM methotrexate to increase the expression levels of CD25.

CHO-CD25 transfectoma culture: CHO-CD25 transfectoma cells (Medarex Inc., NJ, USA) were cultured in CHO-S-SFM II medium (Gibco BRL), without hypoxanthine, without thymidine, with penicillin (5000 U/ml), streptamycin (5000 mg/ml; BioWhittaker, Belgium), and methotrexate (final concentration 50 nM, Sigma). Cells were refreshed every two to three days.

Transgenic Mice: HCo7 and HCo12 mice were housed in filter cages and were evaluated to be in good physical condition on dates of immunization, bleeds, and the day of the fusion. The mice that produced the selected hybridomas were all males. Mouse ID's 23185, 23196, 23197, and 23198 have the (CMD)++; (HCo7) 11952+; (JKD)++; (KCo5) 9272+ genotype. Mouse ID 23175 was of (CMD)++; (HCo12) 15087+; (JKD)++; (KCo5) 9272+ genotype. Individual transgene designations are in parentheses, followed by line numbers for randomly integrated transgenes. The symbols ++ and + indicate homozygous or hemizygous; however, because the mice are routinely screened using a PCR-based assay, it was not possible to distinguish between heterozygosity and homozygosity for the randomly integrated human Ig transgenes. A + designation may be given to mice that are actually homozygous for these elements.

Immunization Procedure and Schedule: Mice were immunized with antigen in two forms: Live cells (the CD25 transfected CHO cells described above) and purified protein (recombinant human CD25 (rhCD25), an NS/0-expressed recombinant protein from R&D Systems, (cat# 223-2A/CF), Minneapolis, Minn.). Soluble rhCD25 was mixed with complete Freund's adjuvant (CFA) or incomplete Freund's adjuvant (IFA). Freund's adjuvant was obtained from Gibco-BRL, Rockville, Md. Mice were injected with 0.2 ml prepared antigen into the intraperitoneal cavity. Final tail vein immunizations were performed with soluble CD25 in sterile PBS or saline (0.9% NaCl). Immunizations with transfected cells were administered into the intraperitoneal cavity (i.p.) at 0.2 ml in sterile saline at $1.0$-$2.0 \times 10^7$ cells per mouse. All immunizations were injected into the intraperitoneal cavity. Three and two days prior to fusion, intravenous (i.v.) boosts were performed. The immunization schedule is described in Table 1. All mice were included among a cohort of twelve (12) mice from HCo7 and HCo12 genotypes.

TABLE 1

| Date of activity | Immunization: adjuvant, Antigen | Bleed and titer*/Fusions |
|---|---|---|
| Day 1 | $1.5 \times 10^7$ live CD25 transfected cells, IP in saline | |
| Day 12 | CFA, rhCD25 (20 µg) | |
| Day 21 | $1.5 \times 10^7$ live CD25 transfected cells, IP in saline | |
| Day 28 | CFA, rhCD25 (20 µg) | |
| Day 35 | | Titer |
| Day 42 | | Fusion 23175/23197 |
| Day 42 | $1.5 \times 10^7$ live CD25 transfected cells, IP in saline | |
| Day 56 | CFA, rhCD25 (20 µg) | |
| Day 63 | | Titer |
| Day 68 | $1.5 \times 10^7$ live CD25 transfected cells, IP in saline | |
| Day 71 | | Fusion 23196/23198 |
| Day 81 | | Titer |
| Day 85 | | Fusion 23185 |

*For titers, please see Table 2.

Mouse titers: The titers for mouse #s 23175, 23185, 23196, 23197, and 23198 are shown below in Table 2. The titers shown in Table 2 indicate serum dilutions which showed positive in CD25 specific tests. The response to the antigen after repeated immunizations show a robust response level and the mouse was prepared for fusion.

TABLE 2

| Mouse # | Titer Day 35 | Titer Day 63 | Titer Day 81 |
|---|---|---|---|
| 23175 | 12800 | | |
| 23185 | 6400 | 12800 | 12800 |
| 23196 | 6400 | 25600 | |
| 23197 | 50000 | | |
| 23198 | 3200 | 25600 | |

Fusion Procedure: The SP2/0-ag14 myeloma cell line (ATCC CRL 1581, lot F-15087) was used for the fusions. The original ATCC vial was thawed and expanded in culture. A seed stock of frozen vials was prepared from this expansion. Cells were maintained in culture for 6-8 weeks, passed twice a week.

High Glucose DMEM: (Mediatech Cellgro, # 1001233) containing 10% FBS (Hyclone cat# SH30071), antibiotic-antimycotic (100×) (Gibco, #15240062), and 0.1% L-glutamine was used to culture myeloma cells. Additional media supplements were added to the hybridoma growth media, including 5% Origen-Hybridoma Cloning Factor (Igen), $4.5 \times 10^{-4}$ M sodium pyruvate, HAT ($1.0 \times 10^{-4}$ M hypoxanthine, $4.0 \times 10^{-4}$ M aminopterin, $1.6 \times 10^{-5}$ M thymidine; Sigma), and fetal bovine serum (Hyclone, Logan, Utah).

The spleen from mouse number #23197 was normal in size and yielded $4.0 \times 10^8$ viable cells. The spleen from mouse number #23175 was normal in size and yielded $2.6 \times 10^8$ viable cells. Spleens from mouse #23196 and #23198 were normal in size and yielded $2.4 \times 10^8$ and $2.0 \times 10^8$ viable cells, respectively. The last spleen from mouse #23185 was normal in size and yielded $1.9 \times 10^8$ viable cells. The splenocytes were fused according to standard procedure.

Media Used for hybridoma generation (fusion): High glucose DMEM (Mediatech, lot#10013264) containing 10% fetal bovine serum (FBS); (Hyclone, Logan, Utah, SH30071 lot#AJE10321) antibiotic-antimycotic (GibcoBRL, lot#15240062), and 0.1% L-glutamine (Gibco, lot#1013845) were used to culture the myeloma cells. Additional media supplements were added to the hybridoma growth media, which included: 5% Origen-Hybridoma Cloning Factor (Igen, lot#36600 and 36782 and 36684), $4.5 \times 10^{-4}$ M sodium pyruvate, HAT (Sigma, H 0262): $1.0 \times 10^{-4}$ M hypoxanthine, $4.0 \times 10^{-7}$ M aminopterin, $1.6 \times 10^{-5}$ M thymidine, or HT (Sigma, H0137): $1.0 \times 10^{-4}$ M hypoxanthine, $1.6 \times 10^{-5}$ M thymidine.

The spleen and lymph nodes were removed from the immunized mice and these organs were placed into a tube containing DMEM+10% FBS. The tube was transferred to a tissue culture room and a single cell suspension was made from the spleen and lymph nodes and the cells were counted. An appropriate volume of SP2/0 cells (ATCC CRL 1581, lot F-15087; 6 spleen or lymph node cells per 1 cell of SP2/0) was transferred and the cells were mixed and resuspended. Approximately 1.2 ml of PEG was added (1 minute while gently swirling the tube in a beaker containing 37° C. water). The tube was left for 90 seconds, 15 ml of DMEM was added and washing with medium was performed. After spinning the cells down, the supernatant was removed and the cells were resuspended. Ten (10) ml of HAT-containing medium was added to the tube. After incubating for 30-60 minutes in a $CO_2$ incubator, the cells were plated into 96-well culture plates, 2001 µl/well (about $1 \times 10^7$ cells per 96-well plate). On day 7, cells were fed with HT-containing medium, 250 µl/well (HT medium is HAT medium with aminopterin removed).

The initial ELISA screen for human IgG,κ antibodies was performed 7-10 days post fusion. Human IgG,κ positive wells were then screened on soluble CD25 coated ELISA plates. Antigen positive hybridomas were then transferred to 24-well plates, and eventually to tissue culture flasks. Antigen positive hybridomas were preserved at several stages in the development process by freezing cells in Origen DMSO freeze medium (Fisher Cat # IG-50-0715).

ELISA protocol for IgG/κ detection (used for screening the fusions): ELISA plates were coated overnight with anti-human-κ, 1 µg/ml (Immunotech, lot#0173) or anti-human-γ, 1 µg/ml (Jackson, lot#109-006-098), 50 µg/well. Plates were emptied and residual binding sites were blocked with PBS supplemented with tween-20 (0.05%) and 5% chicken serum (PBSTC) for 1 hour at room temperature (RT). Plates were washed 3 times with PBS supplemented with 0.05% tween-20 (PBST). Supernatants derived from the fusions and subclones were generally tested diluted 1:2 in PBSTC. As a positive control, human IgG (Calbiochem) was used. After incubating the samples for about 2 hours, the plates were washed with PBST and a secondary antibody, anti-human-IgG-Fc-HRP conjugated (Jackson, lot#109-036-098), 1:5000 diluted in PBSTC was added to the wells (100 µl). After incubation of 1 hour at RT, the ELISA was developed using ABTS (Sigma) according to the manufacturer's recommendations.

Isotype determination by ELISA: 96-well ELISA plates (Greiner, Germany) were coated overnight (100 µl/well, room temperature (RT)) with mouse-anti-human IgG1 (CLB, Netherlands, dilute 1:5,000 from stock) or with mouse-anti-human IgG3 (CLB, dilute 1:10,000 from stock). After washing the plates 3× with PBST (150 µl/well), plates were incubated with PBSTC for 1 hour at RT. Supernatants of human CD25 monoclonal antibody clones were then added (100 µl/well; 2 hours at RT). Anti-KLH IgG1 (1 µg/ml) and anti-KLH IgG3 (1 µg/ml) supernatants served as positive controls. Culture medium and PBSTC served as negative controls. After washing in PBST (3×), goat-anti-hIgG-HRP (Fc specific; Jackson Labs, Maine, USA) was added (1 hour at RT).

For detection of IgG1, the conjugate was diluted 1:500, whereas for detection of IgG3 the conjugate was diluted 1:2000. After washing in PBST (3×), 10 mg ABTS (Roche) per 10 ml ABTS buffer (Roche) was made and 100 µl added to each well. After 20 minutes, absorption was read at 405 nm with an ELISA reader (EL 808, Bio-Tek Instruments, Vermont, USA).

Based on the immunization procedure 4 antigen specific hybridomas were selected which were all derived from HCo mice: AB1, AB7, AB11 and AB12. Isotypes of these four clones were found to be IgG1,κ.

The antibodies of the invention can be recombinantly expressed as other isotypes, for example IgG2, IgG3, IgG4, IgM, and IgA.

Media used for maintaining the hybridomas after selection: All human CD25 monoclonal antibody hybridoma cell lines were cultured in Dulbecco's Modified Eagle Medium (Biowhittaker, lot#BE12-709F) supplemented with 10% FCS (Wisent Multicell optimum C241), 2 mM L-glutamine (Glutamax-II), 50 IU/ml penicillin, 50 µg/ml streptomycin (pen/strep), 2 µM β-ME (all derived from Gibco BRL, Life Technologies, Scotland), 24% HCF (Origen, Igen International Inc., Gaithersburg, USA).

Purification of antibodies: Before purification or concentration of the human CD25 specific antibodies from the culture supernatant, the cell culture supernatant must be filtered through a vacuum driven disposable bottle top filter to remove gross material such as cell rests or other impurities. The sample can be concentrated if the volume of the sample is above 500 ml to a volume beneath 500 ml with a Prep/scale™ TFF, 1 ft² cartridge (Millipore, USA).

Protein A purification of the CD25 specific antibodies was performed using affinity chromatography.

After equilibration of the 5 ml Protein A column (ProtA 5 ml SP, version 041201, Amersham Pharmacia Biotech AB, Sweden) with PBS, pH 7.4, and priming of the sample-pump A with PBS, pH 7.4, the supernatant containing CD25 specific antibodies was loaded onto the column, unbound sample washed out, and the system-pump B rinsed with 0.1 M citric acid, pH 5, (elution buffer 1). Thereafter, bovine IgG (present in the culture supernatant) was eluted with elution buffer 1 via the system pump B. After rinsing the system-pump A with 0.1 M citric acid, pH 3, (elution buffer 2), human CD25 specific antibodies were eluted via the system-pump A with elution buffer 2. System-pump B was then rinsed with 0.1 M citric acid, pH 2, (elution buffer 3) and all remaining IgG bound to the column was eluted via system-pump B with elution buffer 3. The eluted CD25 specific antibodies were neutralized with 10% (v/v) 2 M Tris-HCl (Sigma), pH 9, and the peak-fractions were then pooled.

Pooled peak-fractions from elution-step 2 were dialyzed to PBS (30 ml purified material to 5 l PBS), for 18 hours at 4° C. To preserve and store the purified material, the samples were concentrated. The concentration of human IgG was determined using Nephelometric assay (Dade-Behring, BNII) using polyclonal anti-IgG antibodies (CLB, Amsterdam, The Netherlands, lot#M1090). The antibodies were aliquoted, snap frozen, and stored at −80° C.

Example 2

Antibody Sequencing of Human Antibodies Against CD25

Sequencing of the $V_L$ and $V_H$ regions of the antibodies

Sequencing: The VDJ-regions were sequenced after cloning in the pGEMT-Vector System II. Sequencing was performed at Baseclear (Leiden, Netherlands). The sequences were aligned to germline V-gene sequences in Vbase available on the internet at the website mrc-cpe.cam.ac.uk.

RNA preparation: Total RNA was prepared from $5 \times 10^6$ cells of four (4) different human CD25 hybridoma cell lines (AB1, AB7, AB11, AB12) with Rneasy kit (Qiagen, Westburg, Leusden, Netherlands) according to the manufacturer's protocol.

cDNA preparation: Complementary DNA (cDNA) of RNA from human CD25 hybridoma cells was prepared from 3 μg total RNA with AMV Reverse Transcriptase with buffer (Roche Diagnostics GmbH, Mannheim, Germany), oligo d(T)$_{15}$ (Promega, Madison, Wis., USA), dNTP (Roche Diagnostics GmbH, Mannheim, Germany) and RNAsin (Promega) according to the manufacturer's protocol (2000, version 3).

$V_H$ and $V_L$ regions were amplified using the following PCR primers:

```
V_H: FR1 5' primers
    AB62   CAg gTK CAg CTg gTg CAg TC           (SEQ ID NO:41)

AB63   SAg gTg CAg CTg KTg gAg TC           (SEQ ID NO:42)

AB65   gAg gTg CAg CTg gTg CAg TC           (SEQ ID NO:43)

V_H leader 5' primers
    AB85   ATg gAC Tgg ACC Tgg AgC ATC          (SEQ ID NO:44)

AB86   ATg gAA TTg ggg CTg AgC Tg           (SEQ ID NO:45)

AB87   ATg gAg TTT ggR CTg AgC Tg           (SEQ ID NO:46)

AB88   ATg AAA CAC CTg Tgg TTC TTC          (SEQ ID NO:47)

AB89   ATg ggg TCA ACC gCC ATC CT           (SEQ ID NO:48)

V_H 3' primer
    AB90   TgC CAg ggg gAA gAC CgA Tgg          (SEQ ID NO:49)

V_K: FR1 5' primers
    AB8    RAC ATC CAg ATg AYC CAg TC           (SEQ ID NO:50)

AB9    gYC ATC YRg ATg ACC CAg TC           (SEQ ID NO:51)

AB10   gAT ATT gTg ATg ACC CAg AC           (SEQ ID NO:52)

AB11   gAA ATT gTg TTg ACR CAg TC           (SEQ ID NO:53)

AB12   gAA ATW gTR ATg ACA CAg TC           (SEQ ID NO:54)

AB13   gAT gTT gTg ATg ACA CAG TC           (SEQ ID NO:55)

AB14   gAA ATT gTg CTg ACT CAg TC           (SEQ ID NO:56)

V_K leader 5' primers:
    AB123  CCC gCT Cag CTC CTg ggg CTC CTg      (SEQ ID NO:57)

AB124  CCC TgC TCA gCT CCT ggg gCT gC       (SEQ ID NO:58)

AB125  CCC AgC gCA gCT TCT CTT CCT CCT gC   (SEQ ID NO:59)

AB126  ATg gAA CCA Tgg AAg CCC CAg CAC AgC  (SEQ ID NO:60)

V_K 3' primer
    AB16   Cgg gAA gAT gAA gAC AgA Tg           (SEQ ID NO:61)
```

In the above primer sequences, K, S, R, Y and W have the following meanings:
K=G or T
S=C or G
R=A or G
Y=C or T
W=A or T PCR conditions used to amplify $V_H$ and $V_L$ regions for cloning: Polymerase chain reactions (PCR) were performed with AmpliTaq polymerase (Perkin Elmer) on a T1 Thermocycler 96 (Biometra, Westburg, Leusden, Netherlands).

| PCR cycling protocol: | |
| --- | --- |
| | 94° C. 2 min |
| 11 cycles | 94° C. 30 sec |
| | 65° C. 30 sec, minus 1° per cycle |
| | 72° C. 30 sec |
| 30 cycles | 94° C. 30 sec |
| | 55° C. 30 sec |
| | 72° C. 30 sec |
| | 72° C. 10 min |
| | cool down to 4° C. |

Cloning of $V_H$ and $V_L$ in pGEMT-Vector System II: After analysing the PCR products on an agarose gel, the products were purified with the QIAEX H Gel Extraction Kit (Qiagen, Westburg, Leusden, Netherlands). Always 2 independently amplified PCR products, using FR1 or leader primers, of each $V_H$ and $V_L$ region were cloned in pGEMT-Vector System II (Promega) according to manufacturer's protocol (1999, version 6).

After transformation to *E. coli* JM109, individual colonies were screened by colony PCR using T7 and SP6 primers, 30 annealing cycles at 55° C. Plasmid DNA from colonies was purified using Qiaprep Spin miniprep kit (Qiagen). To further analyse the $V_H$ and $V_L$ regions a Nco1/Not1 (NE Biolabs, Westburg, Leusden, Netherlands) digestion was performed and analysed on agarose gel.

The four selected hybridoma cell lines expressed the following antibody sequences:

AB1: a human monoclonal IgG1,κ antibody with the amino acid sequences: SEQ ID NOs: 2 and 4;

AB7: a human monoclonal IgG1,κ antibody with the amino acid sequences: SEQ ID NOs: 6 and 8;

AB11: a human monoclonal IgG1,κ antibody with the amino acid sequences: SEQ ID NOs: 10 and 12; and AB12: a human monoclonal IgG1,κ antibody with the amino acid sequences: SEQ ID NOs: 14 and 16.

The sequences obtained are shown in FIGS. 1-10.

Example 3

Binding Characteristics of Human Antibodies Against CD25

Binding of supernatants of human CD25 monoclonal antibodies to CD25 constitutively expressed on CHO cells: AB1, AB7, AB11 and AB12 all bound to CD25 expressed on transfected CHO cells when determined by flow cytometry (see Table 3).

Binding of supernatants of human CD25 monoclonal antibodies to hrCD25 in ELISA assay: AB1, AB7, AB11, and AB12 all bound CD25 when tested in an ELISA using hrCD25 as the coating antigen. 96-well plates (Greiner) were coated overnight at RT with rhCD25 (100 ng/ml; R&D), were upon non-specific binding was blocked by coating the plates with PBSTC for 1 hour at RT. After washing (3×) the plates with PBST, 100 µl of sample antibody was added. After washing the plates 3× (PBST), plates were incubated with streptavidin-poly-HRP (1:10,000) in PBS and 100 µl added to each well (1 hour, RT). After washing the plates (3×in PBST), 10 mg ABTS (Roche) per 10 ml ABTS buffer (Roche) was made and 100 µl added to each well. After 20 minutes, absorption was read at 405 nm with an ELISA reader (EL 808, Bio-Tek Instruments).

TABLE 3

Clone names, isotypes, and binding to CD25

| Clone | Subclass | CD25-binding[1] | CHO-CD25[2] |
| --- | --- | --- | --- |
| AB1 | IgG1 | + | + |
| AB7 | IgG1 | + | + |
| AB11 | IgG1 | + | + |
| AB12 | IgG1 | + | + |

Figure 11:
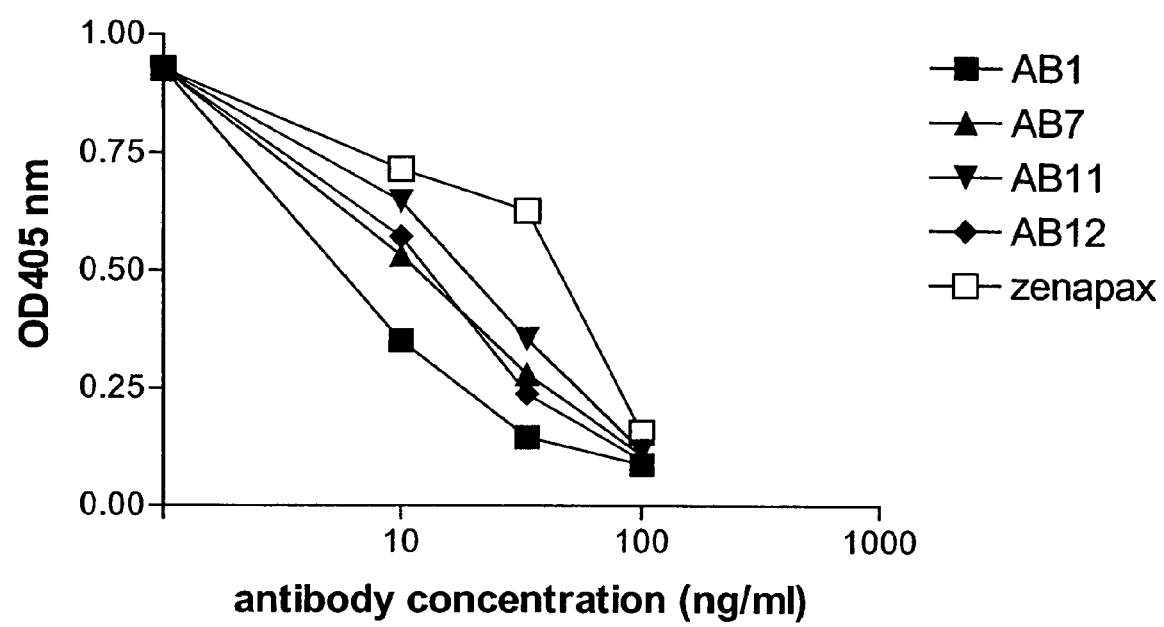
FIG. 11 is a graph showing inhibition of IL-2 binding to its receptor, CD25, by supernatants of human monoclonal antibodies AB1, AB7, AB11, and AB12, compared to inhibition of IL-2 binding by Zenapax® antibody (daclizumab, recombinant humanized IgG1 anti-CD25 antibody, Roche).

[1]Binding of clone culture supernatants as determined by rhCD25 ELISA
[2]Binding to CD25 expressed on transfected CHO cells and determined by flow cytometry Inhibition of binding of biotinylated IL-2 to its receptor by supernatants of human CD25monoclonal antibodies: In order to examine the extent of which human monoclonal antibodies block or inhibit IL-2 binding to CD25 96-well plates (Greiner) were coated overnight at RT with rhCD25 (100 ng/ml; R&D systems, MN, USA), whereupon non-specific binding was blocked by coating the plates with PBSTC for 1 hour at RT. After washing (3×) the plates with PBST, 100 µl of sample antibody (concentration range: 10, 33, and 100 ng/ml) was added. For comparison Zenapax® antibody was also added. After 10 minutes, rIL-2-biotin (50 ng/ml) was added (1.5 hours, RT). After washing the plates 3× (in PBST), plates were incubated with streptavidin-poly-HRP (dilute 1:10,000 from stock) in PBS, and 100 µl was added to each well (1 hour, RT). After washing the plates (3× in PBST), 10 mg ABTS (Roche) per 10 ml ABTS buffer (Roche) was made and 100 µl added to each well. After 20 minutes, absorption was read at 405 nm with an ELISA reader (EL 808, Bio-Tek Instruments). Data show one out of two representative experiments. As shown in FIG. 11, supernatants of human CD25 monoclonal antibodies AB1, AB7, AB11 and AB12 were able to inhibit binding of biotinylated IL-2 to CD25 more efficiently than Zenapax® antibody.

Figure 12:
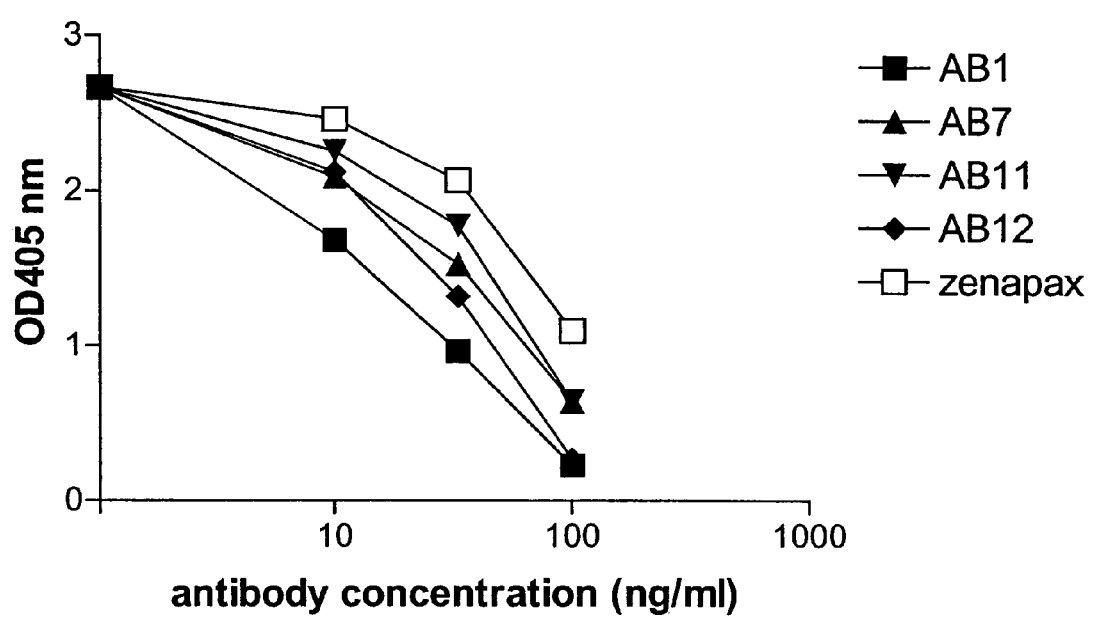
FIG. 12 is a graph showing inhibition of Zenapax® antibody binding to CD25 by human monoclonal antibodies AB1, AB7, AB11, and AB12.

Inhibition of binding of Zenapax® antibody to CD25 by supernatants of human CD25 monoclonal antibodies: In order to examine the extent of which human monoclonal antibodies block or inhibit binding of Zenapax® antibody to CD25, 96-well plates (Greiner) were coated overnight at RT with rhCD25 (100 ng/ml; R&D systems, MN, USA), whereupon non-specific binding was blocked by coating the plates with PBSTC for 1 hour at RT. After washing (3×) the plates with PBST, 100 µl of sample (concentration range: 10, 33, and 100 ng/ml) was added. After 10 minutes, biotinylated Zenapax® antibody (5 ng/ml) was added (1.5 hours, RT). After washing the plates 3× (in PBST), plates were incubated with streptavidin-poly-HIRP (dilute 1:10,000 from stock) in PBS, and 100 µl was added to each well (1 hour, RT). After washing the plates (3× in PBST), 10 mg ABTS (Roche) per 10 ml ABTS buffer (Roche) was made and 100 µl added to each well. After 20 minutes, absorption was read at 405 nm with an ELISA reader (EL 808, Bio-Tek Instruments). Data show one out of two representative experiments. As shown in FIG. 12, supernatants of human monoclonal antibodies AB1, AB7, AB 11, and AB12 block Zenapax® antibody binding to CD25.

Example 4

Human Monoclonal Antibodies Against CD25 Inhibit Anti-CD3 Antibody-Induced T Cell Proliferation Human antibodies were tested for their ability to inhibit T cell proliferation using the T cell proliferation assay. For comparison Zenapax® antibody as well as an isotype control antibody (hIgG1/κ) were also tested.

PBMC isolation: Human blood cells (obtained in buffy coats from Dutch Red Cross Blood Bank, Utrecht, Netherlands) were put on a ficoll gradient (Pharmacia, 2500 rpm, 25 minutes). With a pipette, PBMCs were collected in RPMI 1640 (supplemented with 10% FCS (Wisent Multicell optimum C241), 2 mM L-glutamine, 50 IU/ml penicillin, 50 μg/ml streptomycin, 25 mM HEPES (all derived from Bio Whittaker, Europe)).

T cell proliferation assay: Human PBMCs were diluted in RPMI 1640 (supplemented with 10% FCS (Wisent Multicell optimum C241), 2 mM L-glutamine, 50 IU/ml penicillin, 50 μg/ml streptomycin, 25 mM HEPES (all derived from Bio Whittaker, Europe)) to $1.5 \times 10^5$ cells/well (in triplet) in 96-well flat bottom plates (Greiner). The cells were stimulated with anti-CD3 antibody (CLB-T3/4.E, cat#M1654, 10 ng/ml). Then, 50 μl of increasingly diluted experimental antibodies were added to the cells (ranging from 500 ng/ml to 7.8 ng/ml, in two-step dilutions). After five days (37° C., 5% $CO_2$) proliferation was quantified by using BrdU (end concentration: 10 μM, Roche) according to the method described below.

BrdU labeling assay (Roche BrdU-staining kit, cat no 1 647 229): BrdU labeling solution (100 μM) was added to the wells and cells were incubated overnight (37° C., 5% $CO_2$). Cells were resuspended in wells and centrifuged (10 minutes, 300 g). Supernatant was discarded and cell pellet was dried (1 hour, 60° C.). The pellet was then incubated with FixDenat (200 μl/well; 30 minutes, RT). After incubation, FixDenat was discarded and 100 μl/well anti-BrdU-POD (add 100 μl anti-BrdU stock solution to 10 ml Ab-dilution solution) was added to the pellet (1 hour, RT). After discarding the supernatant, plates were washed (3×) with washing solution (200 μl/well). Finally, 100 ml/well substrate solution was added to the pellet (5 minutes, RT). Coloring reaction was stopped by $H_2SO_4$ (25 μl/well, IM) and optical density was read by ELISA reader at 450 nm (Bio-Tek Instruments).

Figure 13:
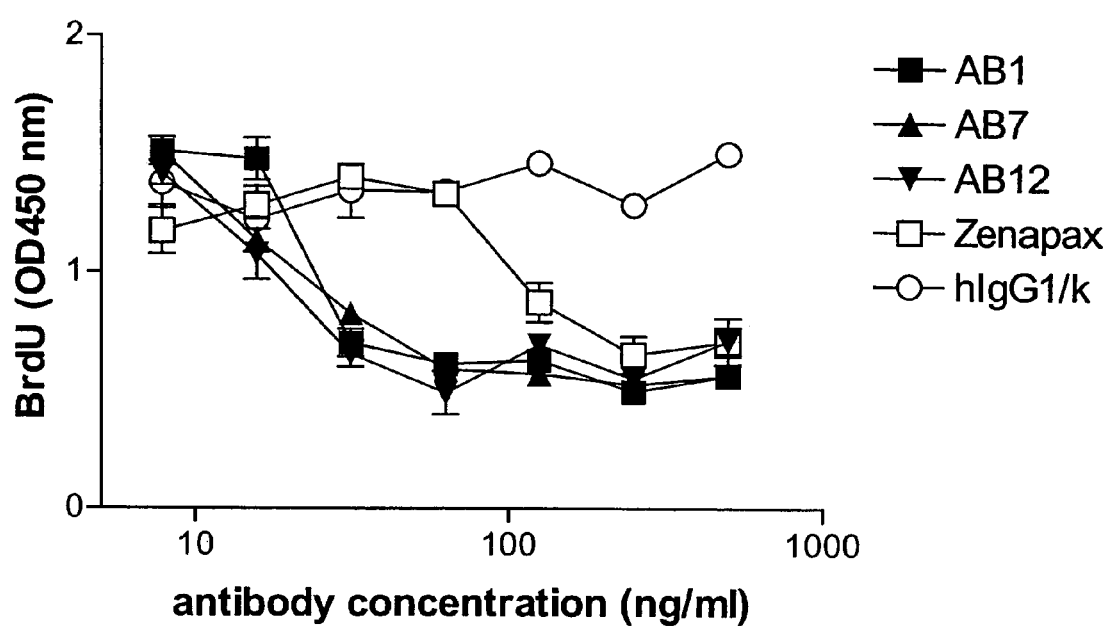
FIG. 13 is a graph showing inhibition of anti-CD3 antibody-induced T cell proliferation (using PBMCs) by human monoclonal antibodies AB1, AB7, AB12, compared to inhibition by a control antibody (hIgG1/κ) and Zenapax® antibody.

As shown in FIG. 13, human monoclonal antibodies AB1, AB7, and AB12 inhibited anti-CD3 antibody-induced T cell proliferation in a dose-dependent manner. The inhibition by the human antibodies was more efficient than by Zenapax® antibody. Data show one out of three representative experiments.

Example 5

Human Monoclonal Antibodies Against CD25 Inhibit MLR

Human antibodies were tested for their ability to inhibit MLR using the MLR assay. For comparison Zenapax® antibody as well as an isotype control antibody (hIgG1/κ) were also tested. Human PBMCs (obtained in buffy coats from Dutch Red Cross Blood Bank, Utrecht, Netherlands) from two non-MHC-matching donors were diluted in RPMI 1640 (supplemented with 10% FCS (Wisent Multicell optimum C241), 2 mM L-glutamine, 50 IU/ml penicillin, 50 μg/ml streptomycin (all derived from Gibco BRL, Life Technologies, Paisley, Scotland)) to $2.0 \times 10^6$ cells/ml. PBMCs from the first donor were irradiated (2000 rads) and mixed ($1.0 \times 10^5$ cells/well) with PBMCs from the second donor ($1.0 \times 10^5$ cells/well) in 96-well flat bottom plates (Greiner) in triplet. Then, 50 μl of increasingly diluted experimental antibodies were added to the cells (ranging from 50 ng/ml to 0.8 ng/ml, in two-step dilutions). After six days of culture, (37° C., 5% $CO_2$) proliferation was quantified by using BrdU (end concentration: 10 μM, Roche) according to the method described above.

Figure 14:
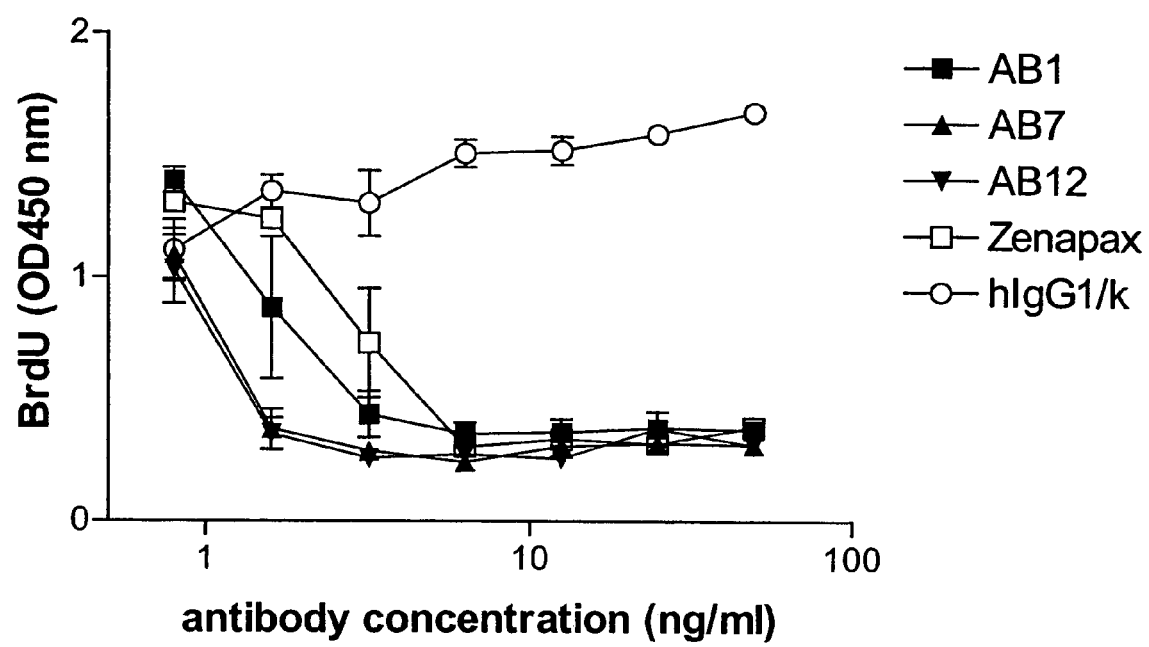
FIG. 14 is a graph showing inhibition of MLR by human monoclonal antibodies AB1, AB7, AB12, compared to inhibition by a control antibody (hIgG1/κ) and Zenapax® antibody.

As shown in FIG. 14, human monoclonal antibodies AB1, AB7, and AB12 inhibited the MLR in a dose-dependent manner. Inhibition of MLR by AB1, AB7, and AB12 (at doses between about 1 and 3 ng/ml) was more efficient than inhibition by Zenapax® antibody. Data show one out of three representative experiments.

Example 6

Kinetic Analysis of AB12 on Biacore 3000 Instrument

Affinity analyses were assessed by monitoring changes in surface plasmon resonance using a BIAcore 3000 instrument. A BIAcore 3000 and BIAcore 3000 software control (BIAcore, Uppsala, Sweden, lot#BR-1100-43) was used. Human CD25 (R&D Systems, lot#223-2A/CFO) was immobilized to a CM-5 sensor chip at low-density (BIAcore, lot#BR-1000-14) using amine-coupling chemistry according to the manufacturer's recommendations. After blocking the residual binding sites of the activated sensor chip using ethanolamine-HCl, a kinetic analysis was performed at 25° C. (according to the manufacturer's recommendations) using human monoclonal antibody AB12 and for comparison Zenapax® antibody. Samples containing AB12 and Zenapax® antibody, respectively, were flowed over the surface of the coated sensor chip allowing AB12 and Zenapax® antibody to associate with rhCD25. The association and dissociation of AB12 and Zenapax® antibody, respectively, were monitored using surface plasmon resonance (SPR) on the sensor chip. The results were visualized using a BIAcore 3000 (Biotek Instruments) and analyzed using the BIAevaluation Software 3.1 (BIAcore, Uppsala, Sweden) and Languir binding 1:1 was used as pre-fixed model.

The $K_D$ of AB12 for the binding to rhCD25 determined by BIAcore analysis: $4.74 \times 10^{-11} \pm 0.43 \times 10^{-11}$.

The $K_D$ of Zenapax® antibody for the binding to rhCD25 determined by BIAcore analysis: $1.52 \times 10^{-10} \pm 0.27 \times 10^{-10}$.

Example 7

AB12-Treatment of T Cell Blasts Results in Internalization of CD25

AB12 was tested for its ability to induce internalization of CD25. Anti-KLH (human IgG1/K isotype antibody, specific for keyhole limpet hemocyanin) was included as isotype control antibody.

Induction of T cell blasts: After isolation of peripheral blood mononuclear cells (PBMCs) from heparin-blood samples using lymphocyte separation medium gradient, PBMCs were stimulated for three to four days with 5 μg/ml phytohemagglutinin (PHA; Difco, cat # 211796) in culture medium (37° C., 5% $CO_2$).

Stimulation of T cell blasts to examine internalization: After harvesting cells and washing in PBS, cells were counted with trypan blue. One part of T-cell blasts ($1 \times 10^6$ cells/ml) was pre-incubated (4° C., for 15 min) with FITC-labeled AB12 (2 μg/ml AB12-FITC), or FITC-labeled anti-KLH (2 μg/ml) as isotype control, or without addition of antibodies. After pre-incubation, cells were washed in PBS, and $1 \times 10^6$ cells (in 1 ml culture medium) were added to 24-well plates, and incubated for 18 hours (37° C., 5% $CO_2$). The remainder of T cell blasts was incubated in the absence or presence of FITC-labeled AB12 (2 µg/ml), or FITC-labeled anti-KLH (2 µg/ml) for 18 hours (37° C., 5% $CO_2$).

After incubation, cells were harvested, and labeled with rhodamine-labeled wheat-germ agglutinin (1 µg/ml, membrane labeling; Molecular Probes, cat No. W-849), at 4° C. for 15 min. Thereafter, cells were washed with PBS, and resuspended in 25 µl Vectashield DAPI (Vector Laboratories, Burlingame, Calif., USA). Then, 10 µl of the cell suspension was pipetted on tissue slides, covered, and analyzed by fluorescence microscopy (Carl Zeiss), and photographs taken with TRITC filter for rhodamine-staining (filter set 15, Zeiss), or FITC filter for the FITC-staining (filter set 09, Zeiss). The membrane staining, obtained with the rhodamine-labeled wheat-germ agglutinin, is not shown.

Figure 15:
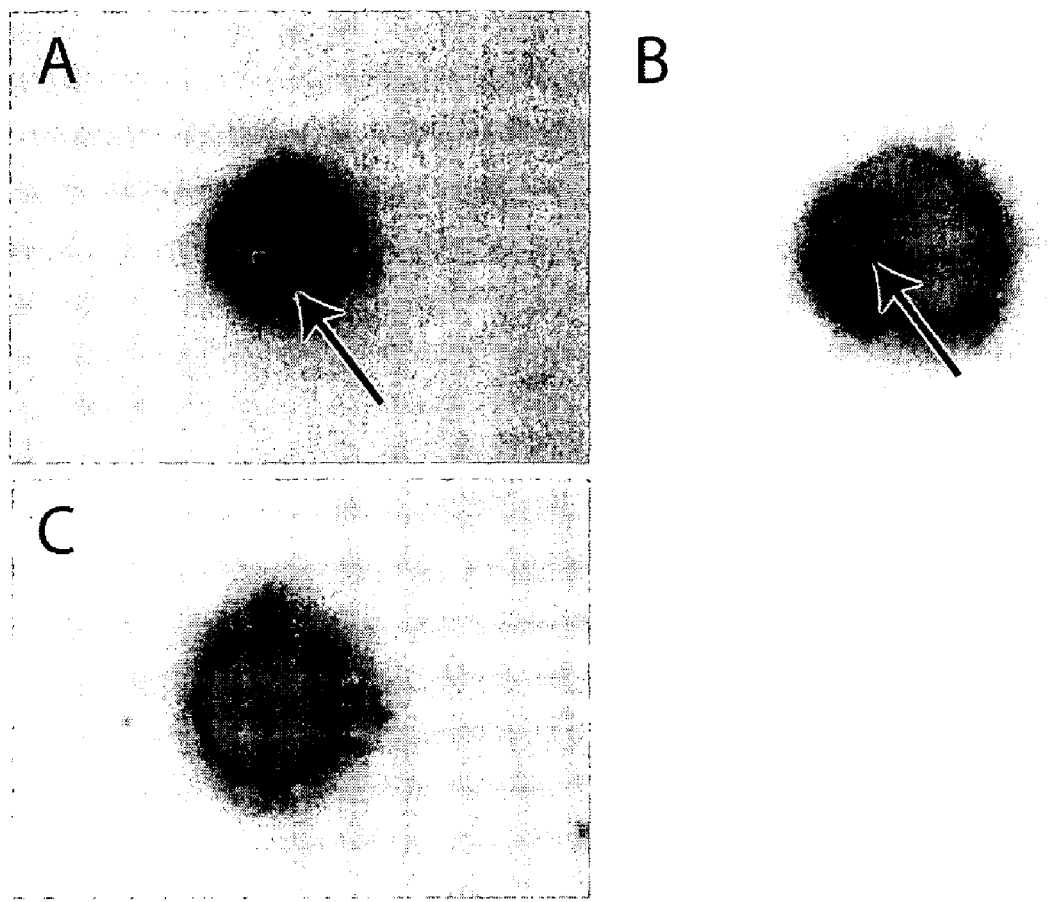
FIG. 15 shows photographs using FITC filter visualizing the internalization of CD25 by FITC-labeled AB12.

As shown in FIGS. 15A and 15B, after 18 hours of culture, the AB12-FITC signal can be found inside the cells. FIG. 15A shows the result after culturing the cells for 18 hours following pre-incubation (15 min) with AB12-FITC and washing, and FIG. 15B shows the result after culturing the cells for 18 hours in the presence of AB12-FITC. A control experiment with the irrelevant FITC-conjugated anti-KLH antibody (FIG. 15C) shows no internalization of FITC-labeled antibody.

Example 8

AB12-Treatment of T Cell Blasts Results in Internalization of CD25 as Measured by Flow Cytometry In another experiment flow cytometry was used to determine internalization of FITC-labeled AB12 in T cell blasts at different time intervals.

After isolation of peripheral blood mononuclear cells (PB-MCs) from heparin-blood samples using lymphocyte separation medium gradient (Ficoll), PBMCs were stimulated for three to four days with 5 µg/ml phytohemagglutinin (PHA; Difco, cat No 211796) in culture medium (37° C., 5% $CO_2$).

After three days of culture the T cell blasts were harvested, washed with PBS, and counted with trypan blue. To the T cell blasts ($2.5 \times 10^6$ cells in 2 ml culture medium), 2 µg/ml FITC-labeled AB12 or FITC-labeled anti-KLH (isotype control antibody) was added. After pre-incubation of cells (4° C., 1 hour), cells were split into two portions. One portion was washed in culture medium, whereas the other portion was not washed. After washing, the pre-incubation samples were resuspended in culture medium. Both portions were incubated at 4° C. or 37° C.

After 0, 0.5, 1, or 4.5 hours of incubation (either at 4° C. or 37° C.), 3 ml of FACS buffer (PBS supplemented with 0.05% BSA and 0.01 µg/ml sodium azide) was added to the cells, and the cells were spun down at 300 g (4° C.). In one portion, cells were resuspended in 200 µl FACS buffer, whereas in the other portion, cells were resuspended in 200 µl FACS buffer and 1 mg/ml ethidium bromide (Sigma, cat No. E8751). The ethidium bromide was added immediately before cell acquisition by flow cytometry.

Ethidium bromide was used to quench the fluorescence signal on the cell surface. As shown in FIG. 16, the fluorescence ratio of the samples incubated at 4° C. measured with or without ethidium bromide was approximately one. This indicates that no internalization has taken place. Cells cultured at 37° C. showed an increase of this fluorescence ratio over time. This indicates that internalization of AB 12-FITC has occurred. As expected, incubation of cells in the continued presence of FITC-labeled AB12 results in higher levels of internalization (FIG. 16B) as compared to cells only pre-incubated with FITC-labeled AB12 (FIG. 16A). FIG. 16A shows the ratio of mean fluorescence intensity (MFI) for cells pre-incubated for 1 hour and excess FITC-labeled-AB12 washed away. FIG. 16B shows the result after culturing the cells in the presence of FITC-labeled AB12. The ratio of MFI is determined by dividing MFI of test samples by MFI of sample at 0 hours. No staining was observed with the isotype control antibody (anti-KLH-FITC, data not shown).

This internalization characteristic of the antibodies of the invention will make them suitable for conjugating with a toxin for the treatment of for example adult T cell leukemia/lymphoma, anaplastic large cell lymphoma, cutanoeus T cell lymphoma (including mycosis fungoides and Sezary's syndrome), peripheral T cell lymphomas, Hodgkin's lymphoma, hairy cell leukemia, and chronic lymphocytic leukemia (CLL)/small lymphocytic lymphoma (SLL).

In another setting, the antibodies of the invention are subjected to reasiolabeling with a suitable radioisotope for the treatment of for example adult T cell leukemia/lymphoma, anaplastic large cell lymphoma, cutanoeus T cell lymphoma (including mycosis fungoides and Sezary's syndrome), peripheral T cell lymphomas, Hodgkin's lymphoma, hairy cell leukemia, and chronic lymphocytic leukemia (CLL)/small lymphocytic lymphoma (SLL).

Furthermore, the antibodies may be labeled with $^{111}$In for determining the tumor burden and thereby adjusting the dosage of radiolabeled antibody to be administered.

Equivalents

Those skilled in the art will recognize or be able to ascertain, using no more than routine experimentation, many equivalents of the specific embodiments of the invention described herein. Such equivalents are intended to be encompassed by the following claims. Any combination of the embodiments disclosed in the dependent claims are also contemplated to be within the scope of the invention.

Incorporation by Reference

All patents, pending patent applications and other publications cited herein are hereby incorporated by reference in their entirety.

SEQUENCE LISTING

<160> NUMBER OF SEQ ID NOS: 61

<210> SEQ ID NO 1
<211> LENGTH: 381
<212> TYPE: DNA
<213> ORGANISM: Homo sapiens

<400> SEQUENCE: 1

```
caggttcagc tggtgcagtc tggggctgag gtgaagaagc ctgggtcctc ggtgaaagtc      60
tcctgcaagg cttctggagg caccttcagc cgttatccta tcaactgggt gcgacaggcc     120
cctggacaag gcttgagtg gatgggaagg atcatcccta tccttggtat agcagactac     180
gcacagaggt tccagggcag agtcacgatt accgcggaca atccacgaa cacagcctac      240 atggagctga gcagcctgag atctgaggac acggccgtgt attattgtgc gaggagggac     300
tggggagact actggggcca gggaaccctg gtcaccgtct cctcagcctc caccaagggc     360
ccatcggtct tccccctggc a                                                381

<210> SEQ ID NO 2
<211> LENGTH: 127
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Arg Tyr
            20                  25                  30

Pro Ile Asn Trp Val Arg Gln Ala Pro Gly Gln Gly Leu Glu Trp Met
        35                  40                  45

Gly Arg Ile Ile Pro Ile Leu Gly Ile Ala Asp Tyr Ala Gln Arg Phe
    50                  55                  60

Gln Gly Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Trp Gly Asp Tyr Trp Gly Gln Gly Thr Leu Val Thr
            100                 105                 110

Val Ser Ser Ala Ser Thr Lys Gly Pro Ser Val Phe Pro Leu Ala
        115                 120                 125

<210> SEQ ID NO 3
<211> LENGTH: 420
<212> TYPE: DNA
<213> ORGANISM: Homo sapiens

<400> SEQUENCE: 3
atggaagccc agcacagct tctcttcctc ctgctactct ggctcccaga taccaccgga      60
gaaattgtgt tgacgcagtc tccaggcacc ctgtctttgt ctccagggga aagagccacc    120
ctctcctgca gggccagtca gagtgttagc agcagcttct tagcctggta ccagcagaaa    180
cctggccagg ctcccaggct cctcatctat ggtgcatcca gcagggccac tggcatccca    240
gacaggttca gtggcagtgg gtctgggaca gacttcactc tcaccatcag cagactggag    300
cctgaagatt ttgcagtgta ttactgtcag cagtatagta gctcaccgct cacttttcggc    360 ggagggacca aggtggagat caaacgaact gtggctgcac catctgtctt catcttcccg    420

<210> SEQ ID NO 4
<211> LENGTH: 120
<212> TYPE: PRT
<213> ORGANISM: Homo sapiens

<400> SEQUENCE: 4

Glu Ile Val Leu Thr Gln Ser Pro Gly Thr Leu Ser Leu Ser Pro Gly
 1               5                  10                  15
```

-continued

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro
        115                 120

<210> SEQ ID NO 5
<211> LENGTH: 381
<212> TYPE: DNA
<213> ORGANISM: Homo sapiens

<400> SEQUENCE: 5
caggttcagc tggtgcagtc tggggctgag gtgaagaagc ctgggtcctc ggtgaaggtc    60
tcctgcaagg cttctggagg caccttcagc agatatgcta tcaactgggt gcgacaggcc   120
cctggacaag gacttgagtg gatgggaagg atcatcccta tccttgatat agcagactac   180
gcacagaagt tccaggacag agtcacgatt accgcggaca gtccacgaa cacagcctac    240 atggagctga gcagcctgag atctgaggac acggccgtgt attactgtgc gagaaaggac   300
tggttcgacc cctggggcca gggaaccctg gtcaccgtct cctcagcctc caccaagggc   360
ccatcggtct tccccctggc a                                              381

<210> SEQ ID NO 6
<211> LENGTH: 127
<212> TYPE: PRT
<213> ORGANISM: Homo sapiens

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Asn Trp Val Arg Gln Ala Pro Gly Gln Gly Leu Glu Trp Met
        35                  40                  45

Gly Arg Ile Ile Pro Ile Leu Asp Ile Ala Asp Tyr Ala Gln Lys Phe
    50                  55                  60

Gln Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Asp Trp Phe Asp Pro Trp Gly Gln Gly Thr Leu Val Thr
            100                 105                 110

Val Ser Ser Ala Ser Thr Lys Gly Pro Ser Val Phe Pro Leu Ala
        115                 120                 125

<210> SEQ ID NO 7
<211> LENGTH: 421
<212> TYPE: DNA

<213> ORGANISM: Homo sapiens

<400> SEQUENCE: 7

| | | |
|---|---|---|
| atggaagccc cagcacagct tctcttcctc ctgctactct ggctcccaga tatcaccgga | 60 |
| gaaaatgtgt tgacgcagtc tccaggcacc ctgtctctgt ctccagggga agagccacc | 120 |
| ctctcctgca gggccagtca gagtggtagc agcagctact tagcctggta ccagcagaaa | 180 |
| cctggccagg ctcccaggct cctcatctat ggtgcatcca gtagggccac tggcatccca | 240 |
| gacaggttca gtggcagtgg gtctgggaca gacttcactc tcaccatcag cagactggag | 300 |
| cctgaagatt ttgcagtgta ttactgtcag cagtatggta gttcaccgat caccttcggc | 360 |
| caagggacac gactggagat aaacgaact gtggctgcac catctgtctt catcttcccc | 420 |
| g | 421 |

<210> SEQ ID NO 8
<211> LENGTH: 120
<212> TYPE: PRT
<213> ORGANISM: Homo sapiens

<400> SEQUENCE: 8

Glu Asn Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Gly Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Ile Thr Phe Gly Gln Gly Thr Arg Leu Glu Ile Lys Arg Thr Val Ala
            100                 105                 110
Ala Pro Ser Val Phe Ile Phe Pro
        115                 120

<210> SEQ ID NO 9
<211> LENGTH: 381
<212> TYPE: DNA
<213> ORGANISM: Homo sapiens

<400> SEQUENCE: 9

| | | |
|---|---|---|
| caggtgcagc tggtgcagtc tggggctgag gtgaagaagc ctgggtcctc ggtgaaagtc | 60 |
| tcctgcaagg cttctggagg caccttcagc cgttatccta tcaactgggt gcgacaggcc | 120 |
| cctggacaag gcttgagtg gatgggaagg atcatcccta tccttggtat agcagactac | 180 |
| gcacagaggt tccagggcag agtcacgatt accgcggaca aattcacgaa cacagcctac | 240 |
| atggagctga gcagcctgag atctgaggac acggccgtgt attattgtgc gaggagggac | 300 |
| tggggagact actggggcca gggaaccctg gtcaccgtct cctcagcctc caccaagggc | 360 |
| ccatcggtct tccccctggc a | 381 |

<210> SEQ ID NO 10
<211> LENGTH: 127
<212> TYPE: PRT
<213> ORGANISM: Homo sapiens

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Arg Tyr
            20                  25                  30

Pro Ile Asn Trp Val Arg Gln Ala Pro Gly Gln Gly Leu Glu Trp Met
            35                  40                  45

Gly Arg Ile Ile Pro Ile Leu Gly Ile Ala Asp Tyr Ala Gln Arg Phe
50                  55                  60

Gln Gly Arg Val Thr Ile Thr Ala Asp Lys Phe Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Trp Gly Asp Tyr Trp Gly Gln Gly Thr Leu Val Thr
            100                 105                 110

Val Ser Ser Ala Ser Thr Lys Gly Pro Ser Val Phe Pro Leu Ala
            115                 120                 125

<210> SEQ ID NO 11
<211> LENGTH: 421
<212> TYPE: DNA
<213> ORGANISM: Homo sapiens

<400> SEQUENCE: 11

```
atggaagccc cagcacagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttagc agcagcttct tagcctggta ccagcagaaa     180
cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgcagtgta ttactgtcag cagtatagta gctcaccgct cactttcggc     360
ggagggacca aggtggagat caaacgaact gtggctgcac catctgtctt catcttcccc     420
g                                                                     421
```

<210> SEQ ID NO 12
<211> LENGTH: 120
<212> TYPE: PRT
<213> ORGANISM: Homo sapiens

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Leu Thr Phe Gly Gly Gly Thr Lys Val Glu Ile Lys Arg Thr Val Ala
            100                 105                 110

```
Ala Pro Ser Val Phe Ile Phe Pro
        115                 120
```

<210> SEQ ID NO 13
<211> LENGTH: 381
<212> TYPE: DNA
<213> ORGANISM: Homo sapiens

<400> SEQUENCE: 13

```
caggtgcagc tggtgcagtc tggggctgag gtgaagaagc ctgggtcctc ggtgaaggtc    60
tcctgcaagg cttctggagg caccttcagc aggtatatta tcaactgggt gcgacaggcc   120
cctggacaag gcttgagtg gatgggaagg atcatccta tccttggtgt agaaaactac    180
gcacagaagt tccagggcag agtcacgatt accgcggaca atccacgag cacagcctac    240
atggagctga gcagcctgag atctgaggac acggccgtgt attactgtgc gagaaaggac   300
tggtttgatt actggggcca gggaaccctg gtcaccgtct cctcagcctc caccaagggc   360
ccatcggtct tccccctggc a                                             381
```

<210> SEQ ID NO 14
<211> LENGTH: 127
<212> TYPE: PRT
<213> ORGANISM: Homo sapiens

<400> SEQUENCE: 14

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Arg Tyr
             20                  25                  30

Ile Ile Asn Trp Val Arg Gln Ala Pro Gly Gln Gly Leu Glu Trp Met
         35                  40                  45

Gly Arg Ile Ile Pro Ile Leu Gly Val Glu Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Lys Asp Trp Phe Asp Tyr Trp Gly Gln Gly Thr Leu Val Thr
            100                 105                 110

Val Ser Ser Ala Ser Thr Lys Gly Pro Ser Val Phe Pro Leu Ala
        115                 120                 125
```

<210> SEQ ID NO 15
<211> LENGTH: 418
<212> TYPE: DNA
<213> ORGANISM: Homo sapiens

<400> SEQUENCE: 15

```
atggaagccc cagcacagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gagtgttagc agctacttag cctggtacca gcagaaacct   180
ggccaggctc ccaggctcct catctatggt gcatccagca gggccactgg catcccagac   240
aggttcagtg gcagtgggtc tgggacagac ttcactctca ccatcagcag actggagcct   300
gaagattttg cagtgtatta ctgtcagcag tatggtagct caccgctcac tttcggcgga   360
gggaccaagg tggagatcaa acgaactgtg gctgcaccat ctgtcttcat cttccccg     418
```

<210> SEQ ID NO 16
<211> LENGTH: 119
<212> TYPE: PRT
<213> ORGANISM: Homo sapiens

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro
        115

<210> SEQ ID NO 17
<211> LENGTH: 5
<212> TYPE: PRT
<213> ORGANISM: Homo sapiens

<400> SEQUENCE: 17

Arg Tyr Pro Ile Asn
1               5

<210> SEQ ID NO 18
<211> LENGTH: 17
<212> TYPE: PRT
<213> ORGANISM: Homo sapiens

<400> SEQUENCE: 18

Arg Ile Ile Pro Ile Leu Gly Ile Ala Asp Tyr Ala Gln Arg Phe Gln
1               5                   10                  15

Gly

<210> SEQ ID NO 19
<211> LENGTH: 6
<212> TYPE: PRT
<213> ORGANISM: Homo sapiens

<400> SEQUENCE: 19

Arg Asp Trp Gly Asp Tyr
1               5

<210> SEQ ID NO 20
<211> LENGTH: 12
<212> TYPE: PRT
<213> ORGANISM: Homo sapiens

<400> SEQUENCE: 20

Arg Ala Ser Gln Ser Val Ser Ser Ser Phe Leu Ala
1               5                   10

```
<210> SEQ ID NO 21
<211> LENGTH: 7
<212> TYPE: PRT
<213> ORGANISM: Homo sapiens

<400> SEQUENCE: 21

Gly Ala Ser Ser Arg Ala Thr
1               5

<210> SEQ ID NO 22
<211> LENGTH: 9
<212> TYPE: PRT
<213> ORGANISM: Homo sapiens

<400> SEQUENCE: 22

Gln Gln Tyr Ser Ser Ser Pro Leu Thr
1               5

<210> SEQ ID NO 23
<211> LENGTH: 5
<212> TYPE: PRT
<213> ORGANISM: Homo sapiens

<400> SEQUENCE: 23

Arg Tyr Ala Ile Asn
1               5

<210> SEQ ID NO 24
<211> LENGTH: 17
<212> TYPE: PRT
<213> ORGANISM: Homo sapiens

<400> SEQUENCE: 24

Arg Ile Ile Pro Ile Leu Asp Ile Ala Asp Tyr Ala Gln Lys Phe Gln
1               5                   10                  15

Asp

<210> SEQ ID NO 25
<211> LENGTH: 6
<212> TYPE: PRT
<213> ORGANISM: Homo sapiens

<400> SEQUENCE: 25

Lys Asp Trp Phe Asp Pro
1               5

<210> SEQ ID NO 26
<211> LENGTH: 12
<212> TYPE: PRT
<213> ORGANISM: Homo sapiens

<400> SEQUENCE: 26

Arg Ala Ser Gln Ser Gly Ser Ser Ser Tyr Leu Ala
1               5                   10

<210> SEQ ID NO 27
<211> LENGTH: 7
<212> TYPE: PRT
<213> ORGANISM: Homo sapiens

<400> SEQUENCE: 27

Gly Ala Ser Ser Arg Ala Thr
1               5
```

```
<210> SEQ ID NO 28
<211> LENGTH: 9
<212> TYPE: PRT
<213> ORGANISM: Homo sapiens

<400> SEQUENCE: 28

Gln Gln Tyr Gly Ser Ser Pro Ile Thr
1               5

<210> SEQ ID NO 29
<211> LENGTH: 5
<212> TYPE: PRT
<213> ORGANISM: Homo sapiens

<400> SEQUENCE: 29

Arg Tyr Pro Ile Asn
1               5

<210> SEQ ID NO 30
<211> LENGTH: 17
<212> TYPE: PRT
<213> ORGANISM: Homo sapiens

<400> SEQUENCE: 30

Arg Ile Ile Pro Ile Leu Gly Ile Ala Asp Tyr Ala Gln Arg Phe Gln
1               5                   10                  15

Gly

<210> SEQ ID NO 31
<211> LENGTH: 6
<212> TYPE: PRT
<213> ORGANISM: Homo sapiens

<400> SEQUENCE: 31

Arg Asp Trp Gly Asp Tyr
1               5

<210> SEQ ID NO 32
<211> LENGTH: 12
<212> TYPE: PRT
<213> ORGANISM: Homo sapiens

<400> SEQUENCE: 32

Arg Ala Ser Gln Ser Val Ser Ser Ser Phe Leu Ala
1               5                   10

<210> SEQ ID NO 33
<211> LENGTH: 7
<212> TYPE: PRT
<213> ORGANISM: Homo sapiens

<400> SEQUENCE: 33

Gly Ala Ser Ser Arg Ala Thr
1               5

<210> SEQ ID NO 34
<211> LENGTH: 9
<212> TYPE: PRT
<213> ORGANISM: Homo sapiens

<400> SEQUENCE: 34

Gln Gln Tyr Ser Ser Ser Pro Leu Thr
1               5
```

```
<210> SEQ ID NO 35
<211> LENGTH: 5
<212> TYPE: PRT
<213> ORGANISM: Homo sapiens

<400> SEQUENCE: 35

Arg Tyr Ile Ile Asn
1               5

<210> SEQ ID NO 36
<211> LENGTH: 17
<212> TYPE: PRT
<213> ORGANISM: Homo sapiens

<400> SEQUENCE: 36

Arg Ile Ile Pro Ile Leu Gly Val Glu Asn Tyr Ala Gln Lys Phe Gln
1               5                   10                  15

Gly

<210> SEQ ID NO 37
<211> LENGTH: 6
<212> TYPE: PRT
<213> ORGANISM: Homo sapiens

<400> SEQUENCE: 37

Lys Asp Trp Phe Asp Tyr
1               5

<210> SEQ ID NO 38
<211> LENGTH: 12
<212> TYPE: PRT
<213> ORGANISM: Homo sapiens

<400> SEQUENCE: 38

Arg Ala Ser Gln Ser Val Ser Ser Ser Tyr Leu Ala
1               5                   10

<210> SEQ ID NO 39
<211> LENGTH: 7
<212> TYPE: PRT
<213> ORGANISM: Homo sapiens

<400> SEQUENCE: 39

Gly Ala Ser Ser Arg Ala Thr
1               5

<210> SEQ ID NO 40
<211> LENGTH: 9
<212> TYPE: PRT
<213> ORGANISM: Homo sapiens

<400> SEQUENCE: 40

Gln Gln Tyr Ser Ser Ser Pro Leu Thr
1               5

<210> SEQ ID NO 41
<211> LENGTH: 20
<212> TYPE: PRT
<213> ORGANISM: Homo sapiens

<400> SEQUENCE: 41

Cys Ala Gly Gly Thr Lys Cys Ala Gly Cys Thr Gly Gly Thr Gly Cys
1               5                   10                  15
```

Ala Gly Thr Cys
            20

<210> SEQ ID NO 42
<211> LENGTH: 20
<212> TYPE: PRT
<213> ORGANISM: Homo sapiens

<400> SEQUENCE: 42

Ser Ala Gly Gly Thr Gly Cys Ala Gly Cys Thr Gly Lys Thr Gly Gly
1               5                   10                  15

Ala Gly Thr Cys
            20

<210> SEQ ID NO 43
<211> LENGTH: 20
<212> TYPE: PRT
<213> ORGANISM: Homo sapiens

<400> SEQUENCE: 43

Gly Ala Gly Gly Thr Gly Cys Ala Gly Cys Thr Gly Gly Thr Gly Cys
1               5                   10                  15

Ala Gly Thr Cys
            20

<210> SEQ ID NO 44
<211> LENGTH: 21
<212> TYPE: PRT
<213> ORGANISM: Homo sapiens

<400> SEQUENCE: 44

Ala Thr Gly Gly Ala Cys Thr Gly Gly Ala Cys Cys Thr Gly Gly Ala
1               5                   10                  15

Gly Cys Ala Thr Cys
            20

<210> SEQ ID NO 45
<211> LENGTH: 20
<212> TYPE: PRT
<213> ORGANISM: Homo sapiens

<400> SEQUENCE: 45

Ala Thr Gly Gly Ala Ala Thr Thr Gly Gly Gly Cys Thr Gly Gly Ala
1               5                   10                  15

Gly Cys Thr Gly
            20

<210> SEQ ID NO 46
<211> LENGTH: 20
<212> TYPE: PRT
<213> ORGANISM: Homo sapiens

<400> SEQUENCE: 46

Ala Thr Gly Gly Ala Gly Thr Thr Thr Gly Gly Arg Cys Thr Gly Ala
1               5                   10                  15

Gly Cys Thr Gly
            20

<210> SEQ ID NO 47
<211> LENGTH: 21
<212> TYPE: PRT
<213> ORGANISM: Homo sapiens

```
<400> SEQUENCE: 47

Ala Thr Gly Ala Ala Ala Cys Ala Cys Cys Thr Gly Thr Gly Gly Thr
1               5                   10                  15

Thr Cys Thr Thr Cys
            20

<210> SEQ ID NO 48
<211> LENGTH: 20
<212> TYPE: PRT
<213> ORGANISM: Homo sapiens

<400> SEQUENCE: 48

Ala Thr Gly Gly Gly Gly Thr Cys Ala Ala Cys Cys Gly Cys Cys Ala
1               5                   10                  15

Thr Cys Cys Thr
            20

<210> SEQ ID NO 49
<211> LENGTH: 21
<212> TYPE: PRT
<213> ORGANISM: Homo sapiens

<400> SEQUENCE: 49

Thr Gly Cys Cys Ala Gly Gly Gly Gly Ala Ala Gly Ala Cys Cys
1               5                   10                  15

Gly Ala Thr Gly Gly
            20

<210> SEQ ID NO 50
<211> LENGTH: 20
<212> TYPE: PRT
<213> ORGANISM: Homo sapiens

<400> SEQUENCE: 50

Arg Ala Cys Ala Thr Cys Cys Ala Gly Ala Thr Gly Ala Tyr Cys Cys
1               5                   10                  15

Ala Gly Thr Cys
            20

<210> SEQ ID NO 51
<211> LENGTH: 20
<212> TYPE: PRT
<213> ORGANISM: Homo sapiens

<400> SEQUENCE: 51

Gly Tyr Cys Ala Thr Cys Tyr Arg Gly Ala Thr Gly Ala Cys Cys Cys
1               5                   10                  15

Ala Gly Thr Cys
            20

<210> SEQ ID NO 52
<211> LENGTH: 20
<212> TYPE: PRT
<213> ORGANISM: Homo sapiens

<400> SEQUENCE: 52

Gly Ala Thr Ala Thr Thr Gly Thr Gly Ala Thr Gly Ala Cys Cys Cys
1               5                   10                  15

Ala Gly Ala Cys
            20
```

```
<210> SEQ ID NO 53
<211> LENGTH: 20
<212> TYPE: PRT
<213> ORGANISM: Homo sapiens

<400> SEQUENCE: 53

Gly Ala Ala Ala Thr Thr Gly Thr Gly Thr Thr Gly Ala Cys Arg Cys
1               5                   10                  15

Ala Gly Thr Cys
            20

<210> SEQ ID NO 54
<211> LENGTH: 20
<212> TYPE: PRT
<213> ORGANISM: Homo sapiens

<400> SEQUENCE: 54

Gly Ala Ala Ala Thr Trp Gly Thr Arg Ala Thr Gly Ala Cys Ala Cys
1               5                   10                  15

Ala Gly Thr Cys
            20

<210> SEQ ID NO 55
<211> LENGTH: 20
<212> TYPE: PRT
<213> ORGANISM: Homo sapiens

<400> SEQUENCE: 55

Gly Ala Thr Gly Thr Thr Gly Thr Gly Ala Thr Gly Ala Cys Ala Cys
1               5                   10                  15

Ala Gly Thr Cys
            20

<210> SEQ ID NO 56
<211> LENGTH: 20
<212> TYPE: PRT
<213> ORGANISM: Homo sapiens

<400> SEQUENCE: 56

Gly Ala Ala Ala Thr Thr Gly Thr Gly Cys Thr Gly Ala Cys Thr Cys
1               5                   10                  15

Ala Gly Thr Cys
            20

<210> SEQ ID NO 57
<211> LENGTH: 24
<212> TYPE: PRT
<213> ORGANISM: Homo sapiens

<400> SEQUENCE: 57

Cys Cys Cys Gly Cys Thr Cys Ala Gly Cys Thr Cys Thr Gly Gly
1               5                   10                  15

Gly Gly Cys Thr Cys Cys Thr Gly
            20

<210> SEQ ID NO 58
<211> LENGTH: 23
<212> TYPE: PRT
<213> ORGANISM: Homo sapiens

<400> SEQUENCE: 58

Cys Cys Cys Thr Gly Cys Thr Cys Ala Gly Cys Thr Cys Thr Gly
1               5                   10                  15
```

```
Gly Gly Gly Cys Thr Gly Cys
            20

<210> SEQ ID NO 59
<211> LENGTH: 26
<212> TYPE: PRT
<213> ORGANISM: Homo sapiens

<400> SEQUENCE: 59

Cys Cys Cys Ala Gly Cys Gly Cys Ala Gly Cys Thr Thr Cys Thr Cys
1               5                   10                  15

Thr Thr Cys Cys Thr Cys Cys Thr Gly Cys
            20                  25

<210> SEQ ID NO 60
<211> LENGTH: 27
<212> TYPE: PRT
<213> ORGANISM: Homo sapiens

<400> SEQUENCE: 60

Ala Thr Gly Gly Ala Ala Cys Cys Ala Thr Gly Gly Ala Ala Gly Cys
1               5                   10                  15

Cys Cys Cys Ala Gly Cys Ala Cys Ala Gly Cys
            20                  25

<210> SEQ ID NO 61
<211> LENGTH: 20
<212> TYPE: PRT
<213> ORGANISM: Homo sapiens

<400> SEQUENCE: 61

Cys Gly Gly Gly Ala Ala Gly Ala Thr Gly Ala Ala Gly Ala Cys Ala
1               5                   10                  15

Gly Ala Thr Gly
            20
```

We claim:

1. An isolated human monoclonal antibody which binds to human CD25 and inhibits IL-2 binding to CD25, wherein the antibody comprises a human heavy chain variable region comprising CDR1, CDR2, and CDR3 sequences comprising the amino acid sequences set forth in SEQ ID NOs:35, 36, and 37, respectively, and a human light chain variable region comprising CDR1, CDR2, and CDR3 sequences comprising the amino acid sequences set forth in SEQ ID NOs:38, 39, and 40, respectively.

2. An isolated human monoclonal antibody which binds to human CD25 and inhibits IL-2 binding to CD25, wherein the antibody comprises a human heavy chain variable region comprising CDR1, CDR2, and CDR3 sequences comprising the amino acid sequences set forth in SEQ ID NOs:17, 18 and 19, respectively, and a human light chain variable region comprising CDR1, CDR2, and CDR3 sequences comprising the amino acid sequences set forth in SEQ ID NOs:20, 21, and 22, respectively.

3. An isolated human monoclonal antibody which binds to human CD25 and inhibits IL-2 binding to CD25, wherein the antibody comprises a human heavy chain variable region comprising CDR1, CDR2, and CDR3 sequences comprising the amino acid sequences set forth in SEQ ID NOs:23, 24, and 25, respectively, and a human light chain variable region comprising CDR1, CDR2, and CDR3 sequences comprising the amino acid sequences set forth in SEQ ID NOs:26, 27, and 28, respectively.

4. An isolated human monoclonal antibody which binds to human CD25 and inhibits IL-2 binding to CD25, wherein the antibody comprises a human heavy chain variable region comprising CDR1, CDR2, and CDR3 sequences comprising the amino acid sequences set forth in SEQ ID NOs:29, 30, and 31, respectively, and a human light chain variable region comprising CDR1, CDR2, and CDR3 sequences comprising the amino acid sequences set forth in SEQ ID NOs:32, 33, and 34, respectively.

5. The antibody of any one of claims 1-4, selected from the group consisting of an IgG1, an IgG2, an IgG3, an IgG4, an IgM, an IgA1, an IgA2, a secretory IgA, an IgD, and an IgE antibody.

6. The antibody of any one of claims 1-4, wherein the antibody is an IgG1 antibody.

7. The antibody of any one of claims 1-4 wherein the antibody is an IgG4 antibody.

8. The antibody of any one of claims 1-4, wherein the antibody dissociates from human CD25 with a dissociation equilibrium constant ($K_D$) of $10^{-8}$ M or less, when determined by surface plasmon resonance (SPR) technology in a BIAcore 3000 instrument using human recombinant CD25 as the ligand and the antibody as the analyte.

9. The antibody of any one of claim 1-4 wherein the antibody has one or more of the following characteristics:
   (a) specificity for human CD25;
   (b) inhibits binding of IL-2 to CD25;
   (c) eliminates T cells expressing CD25;
   (d) tolerizes T cells;
   (e) inhibits proliferation of T cells expressing CD25;
   (f) inhibits anti-CD3 antibody-induced T cell proliferation of peripheral blood mononuclear cells (PBMCs);
   (g) inhibits mixed lymphocyte reaction (MLR);
   (h) internalization of CD25 expressed on T cells.

10. An isolated monoclonal antibody which binds to human CD25, encoded by human heavy chain and human kappa light chain nucleic acids comprising nucleotide sequences in their variable regions as set forth in SEQ ID NO:5 and SEQ ID NO:7, respectively.

11. An isolated monoclonal antibody which binds to human CD25, encoded by human heavy chain and human kappa light chain nucleic acids comprising nucleotide sequences in their variable regions as set forth in SEQ ID NO:13 and SEQ ID NO:15, respectively.

12. An isolated monoclonal antibody which binds to human CD25, encoded by human heavy chain and human kappa light chain nucleic acids comprising nucleotide sequences in their variable regions as set forth in SEQ ID NO:1 and SEQ ID NO:3, respectively.

13. An isolated monoclonal antibody which binds to human CD25, encoded by human heavy chain and human kappa light chain nucleic acids comprising nucleotide sequences in their variable regions as set forth in SEQ ID NO:9 and SEQ ID NO:11, respectively.

14. An isolated monoclonal antibody which binds to human CD25, having a human heavy chain and human kappa light chain variable regions comprising the amino acid sequences as set forth in SEQ ID NO:6 and SEQ ID NO:8, respectively.

15. An isolated monoclonal antibody which binds to human CD25, having a human heavy chain and human kappa light chain variable regions comprising the amino acid sequences as set forth in SEQ ID NO:14 and SEQ ID NO:16, respectively.

16. An isolated monoclonal antibody which binds to human CD25, having a human heavy chain and human kappa light chain variable regions comprising the amino acid sequences as set forth in SEQ ID NO:2 and SEQ ID NO:4, respectively.

17. An isolated monoclonal antibody which binds to human CD25, having a human heavy chain and human kappa light chain variable regions comprising the amino acid sequences as set forth in SEQ ID NO:10 and SEQ ID NO:12, respectively.

18. An isolated monoclonal antibody that binds human CD25, comprising a full heavy chain and a full light chain variable region, wherein at least one human variable region is selected from the group consisting of: SEQ ID NOs: 2, 4, 6, 8, 10, 12, 14, and 16.

19. An isolated human monoclonal antibody which binds to an epitope on human CD25 defined by the antibody of any one of claims 1-4.

20. An isolated human monoclonal antibody which has the binding characteristics of the antibody of any one of claims 1-4.

21. The antibody of any one of claims 1-4, which is an intact antibody selected from the group consisting of an intact IgG1 antibody, an intact IgG2 antibody, an intact IgG3 antibody, an intact IgG4 antibody, an intact IgM antibody, an intact IgA1 antibody, an intact IgA2 antibody, an intact secretory IgA antibody, an intact IgD antibody, and an intact IgE antibody, wherein the antibody is glycosylated in a eukaryotic cell.

22. The antibody of any one of claims 1-4, which is an intact antibody selected from the group consisting of an intact IgG1, κ antibody; an intact IgG1, λ antibody; an intact IgG4, κ antibody; and an intact IgG4, λ antibody, wherein the antibody is glycosylated in a eukaryotic cell.

23. The antibody of any one of claims 1-4 which is an antibody fragment or a single chain antibody.

24. The antibody of any one of claims 1-4 further comprising a chelator linker for attaching a radioisotope.

25. An isolated monoclonal antibody which binds to human CD25, wherein the antibody comprises a heavy chain variable region comprising CDR1, CDR2, and CDR3 sequences comprising the amino acid sequences set forth in SEQ ID NOs:35, 36, and 37, respectively, and a light chain variable region comprising CDR1, CDR2, and CDR3 sequences comprising the amino acid sequences set forth in SEQ ID NOs:38, 39, and 40, respectively.

26. An isolated monoclonal antibody which binds to human CD25, wherein the antibody comprises a heavy chain variable region comprising CDR1, CDR2, and CDR3 sequences comprising the amino acid sequences set forth in SEQ ID NOs:17, 18 and 19, respectively, and a light chain variable region comprising CDR1, CDR2, and CDR3 sequences comprising the amino acid sequences set forth in SEQ ID NOs:20, 21, and 22, respectively.

27. An isolated monoclonal antibody which binds to human CD25, wherein the antibody comprises a heavy chain variable region comprising CDR1, CDR2, and CDR3 sequences comprising the amino acid sequences set forth in SEQ ID NOs:23, 24, and 25, respectively, and a light chain variable region comprising CDR1, CDR2, and CDR3 sequences comprising the amino acid sequences set forth in SEQ ID NOs:26, 27, and 28, respectively.

28. An isolated monoclonal antibody which binds to human CD25, wherein the antibody comprises a heavy chain variable region comprising CDR1, CDR2, and CDR3 sequences comprising the amino acid sequences set forth in SEQ ID NOs:29, 30, and 31, respectively, and a light chain variable region comprising CDR1, CDR2, and CDR3 sequences comprising the amino acid sequences set forth in SEQ ID NOs:32, 33, and 34, respectively.

29. An isolated monoclonal antibody which binds to an epitope on human CD25 defined by the antibody of any one of claims 25-28.

30. An isolated monoclonal antibody which has the binding characteristics of the antibody of any one of claims 25-28.

31. An isolated monoclonal antibody that binds human CD25, comprising a full heavy chain and a full light chain variable region, wherein at least one variable region is selected from the group consisting of: SEQ ID NOs: 2, 4, 6, 8, 10, 12, 14, and 16.

* * * * *

UNITED STATES PATENT AND TRADEMARK OFFICE
CERTIFICATE OF CORRECTION

| | | |
|---|---|---|
| PATENT NO. | : 7,438,907 B2 | Page 1 of 18 |
| APPLICATION NO. | : 10/714353 | |
| DATED | : October 21, 2008 | |
| INVENTOR(S) | : Schuurman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 854 days.

Signed and Sealed this

Thirty-first Day of May, 2011

David J. Kappos
*Director of the United States Patent and Trademark Office*

CERTIFICATE OF CORRECTION (continued)
U.S. Pat. No. 7,438,907 B2

Col. 53, delete the Sequence Listing and insert the following:
--

```
<110> Schuurman, Janine
      Havenith, Karin
      Parren, Paul
      van de Winkel, Jan
      Williams, Denise Leah
      PETERSEN, JORGEN
      BAADSGAARD, OLE

<120> HUMAN MONOCLONAL ANTIBODIES AGAINST CD25

<130> GMI-059

<140> 10/714,353
<141> 2003-11-14

<150> 60/426690
<151> 2002-11-15

<160> 61

<170> FastSEQ for Windows Version 4.0

<210> 1
<211> 381
<212> DNA
<213> Homo sapiens

<400> 1
caggttcagc tggtgcagtc tggggctgag gtgaagaagc ctgggtcctc ggtgaaagtc  60
tcctgcaagg cttctggagg caccttcagc cgttatccta tcaactgggt gcgacaggcc 120
cctggacaag ggcttgagtg gatgggaagg atcatcccta tccttggtat agcagactac 180
gcacagaggt tccagggcag agtcacgatt accgcggaca aatccacgaa cacagcctac 240
atggagctga gcagcctgag atctgaggac acggccgtgt attattgtgc gaggagggac 300
tggggagact actggggcca gggaaccctg gtcaccgtct cctcagcctc caccaagggc 360
```

```
ccatcggtct tccccctggc a                                             381

<210> 2
<211> 127
<212> PRT
<213> Homo sapiens

<400> 2
Gln Val Gln Leu Val Gln Ser Gly Ala Glu Val Lys Lys Pro Gly Ser
 1               5                  10                  15
Ser Val Lys Val Ser Cys Lys Ala Ser Gly Gly Thr Phe Ser Arg Tyr
                20                  25                  30
Pro Ile Asn Trp Val Arg Gln Ala Pro Gly Gln Gly Leu Glu Trp Met
            35                  40                  45
Gly Arg Ile Ile Pro Ile Leu Gly Ile Ala Asp Tyr Ala Gln Arg Phe
        50                  55                  60
Gln Gly Arg Val Thr Ile Thr Ala Asp Lys Ser Thr Asn Thr Ala Tyr
65                  70                  75                  80
Met Glu Leu Ser Ser Leu Arg Ser Glu Asp Thr Ala Val Tyr Tyr Cys
                85                  90                  95
Ala Arg Arg Asp Trp Gly Asp Tyr Trp Gly Gln Gly Thr Leu Val Thr
                100                 105                 110
Val Ser Ser Ala Ser Thr Lys Gly Pro Ser Val Phe Pro Leu Ala
            115                 120                 125

<210> 3
<211> 420
<212> DNA
<213> Homo sapiens

<400> 3
atggaagccc cagcacagct tctcttcctc ctgctactct ggctcccaga taccaccgga  60
gaaattgtgt tgacgcagtc tccaggcacc ctgtctttgt ctccagggga aagagccacc 120
ctctcctgca gggccagtca gagtgttagc agcagcttct agcctggta ccagcagaaa 180
cctggccagg ctcccaggct cctcatctat ggtgcatcca gcagggccac tggcatccca 240
gacaggttca gtggcagtgg gtctgggaca gacttcactc tcaccatcag cagactggag 300
cctgaagatt ttgcagtgta ttactgtcag cagtatagta gctcaccgct cactttcggc 360
ggagggacca aggtggagat caaacgaact gtggctgcac catctgtctt catcttcccg 420

<210> 4
<211> 120
<212> PRT
<213> Homo sapiens

<400> 4
Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Val Ser Ser Ser
                20                  25                  30
Phe Leu Ala Trp Tyr Gln Gln Lys Pro Gly Gln Ala Pro Arg Leu Leu
```

```
                    35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                      70                  75                  80
Pro Glu Asp Phe Ala Val Tyr Tyr Cys Gln Gln Tyr Ser Ser Ser Pro
                    85                  90                  95
Leu Thr Phe Gly Gly Gly Thr Lys Val Glu Ile Lys Arg Thr Val Ala
                100                 105                 110
Ala Pro Ser Val Phe Ile Phe Pro
                115             120

<210> 5
<211> 381
<212> DNA
<213> Homo sapiens

<400> 5
caggttcagc tggtgcagtc tggggctgag gtgaagaagc ctggtcctc  ggtgaaggtc   60
tcctgcaagg cttctggagg cacccttcagc agatatgcta tcaactgggt gcgacaggcc  120
cctggacaag gacttgagtg gatgggaagg atcatcccta tccttgatat agcagactac  180
gcacagaagt tccaggacag agtcacgatt accgcggaca gtccacgaa  cacagcctac  240
atggagctga gcagcctgag atctgaggac acggccgtgt attactgtgc gagaaaggac  300
tggttcgacc cctggggcca gggaaccctg gtcaccgtct cctcagcctc caccaagggc  360
ccatcggtct tccccctggc a                                            381

<210> 6
<211> 127
<212> PRT
<213> Homo sapiens

<400> 6
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Arg Tyr
                20                  25                  30
Ala Ile Asn Trp Val Arg Gln Ala Pro Gly Gln Gly Leu Glu Trp Met
                35                  40                  45
Gly Arg Ile Ile Pro Ile Leu Asp Ile Ala Asp Tyr Ala Gln Lys Phe
        50                  55                  60
Gln Asp Arg Val Thr Ile Thr Ala Asp Lys Ser Thr Asn Thr Ala Tyr
65                  70                  75                  80
Met Glu Leu Ser Ser Leu Arg Ser Glu Asp Thr Ala Val Tyr Tyr Cys
                85                  90                  95
Ala Arg Lys Asp Trp Phe Asp Pro Trp Gly Gln Gly Thr Leu Val Thr
                100                 105                 110
Val Ser Ser Ala Ser Thr Lys Gly Pro Ser Val Phe Pro Leu Ala
                115                 120                 125

<210> 7
```

```
<211> 421
<212> DNA
<213> Homo sapiens

<400> 7
atggaagccc cagcacagct tctcttcctc ctgctactct ggctcccaga tatcaccgga   60
gaaaatgtgt tgacgcagtc tccaggcacc ctgtctctgt ctccagggga aagagccacc  120
ctctcctgca gggccagtca gagtggtagc agcagctact tagcctggta ccagcagaaa  180
cctggccagg ctcccaggct cctcatctat ggtgcatcca gtagggccac tgcatccca   240
gacaggttca gtggcagtgg gtctgggaca gacttcactc tcaccatcag cagactggag  300
cctgaagatt ttgcagtgta ttactgtcag cagtatggta gttcaccgat caccttcggc  360
caagggacac gactggagat taaacgaact gtggctgcac catctgtctt catcttcccc  420
g                                                                 421

<210> 8
<211> 120
<212> PRT
<213> Homo sapiens

<400> 8
Glu Asn Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Gly Ser Ser Ser
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Ile Thr Phe Gly Gln Gly Thr Arg Leu Glu Ile Lys Arg Thr Val Ala
            100                 105                 110
Ala Pro Ser Val Phe Ile Phe Pro
            115                 120

<210> 9
<211> 381
<212> DNA
<213> Homo sapiens

<400> 9
caggtgcagc tggtgcagtc tggggctgag gtgaagaagc ctgggtcctc ggtgaaagtc   60
tcctgcaagg cttctggagg caccttcagc cgttatccta tcaactgggt gcgacaggcc  120
cctggacaag ggcttgagtg gatgggaagg atcatcccta tccttggtat agcagactac  180
gcacagaggt tccagggcag agtcacgatt accgcggaca aattcacgaa cacagcctac  240
atggagctga gcagcctgag atctgaggac acggccgtgt attattgtgc gaggagggac  300
tggggagact actgggccca gggaaccctg gtcaccgtct cctcagcctc caccaagggc  360
ccatcggtct tccccctggc a                                           381
```

```
<210> 10
<211> 127
<212> PRT
<213> Homo sapiens

<400> 10
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Arg Tyr
            20                  25                  30
Pro Ile Asn Trp Val Arg Gln Ala Pro Gly Gln Gly Leu Glu Trp Met
        35                  40                  45
Gly Arg Ile Ile Pro Ile Leu Gly Ile Ala Asp Tyr Ala Gln Arg Phe
    50                  55                  60
Gln Gly Arg Val Thr Ile Thr Ala Asp Lys Phe Thr Asn Thr Ala Tyr
65                  70                  75                  80
Met Glu Leu Ser Ser Leu Arg Ser Glu Asp Thr Ala Val Tyr Tyr Cys
                85                  90                  95
Ala Arg Arg Asp Trp Gly Asp Tyr Trp Gly Gln Gly Thr Leu Val Thr
            100                 105                 110
Val Ser Ser Ala Ser Thr Lys Gly Pro Ser Val Phe Pro Leu Ala
        115                 120                 125

<210> 11
<211> 421
<212> DNA
<213> Homo sapiens

<400> 11
atggaagccc cagcacagct tctcttcctc ctgctactct ggctcccaga taccaccgga  60
gaaattgtgt tgacgcagtc tccaggcacc ctgtctttgt ctccagggga aagagccacc 120
ctctcctgca gggccagtca gagtgttagc agcagcttct tagcctggta ccagcagaaa 180
cctggccagg ctcccaggct cctcatctat ggtgcatcca gcagggccac tggcatccca 240
gacaggttca gtggcagtgg gtctgggaca gacttcactc tcaccatcag cagactggag 300
cctgaagatt ttgcagtgta ttactgtcag cagtatagta gctcaccgct cactttcggc 360
ggagggacca aggtggagat caaacgaact gtggctgcac catctgtctt catcttcccc 420
g                                                                421

<210> 12
<211> 120
<212> PRT
<213> Homo sapiens

<400> 12
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Phe Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
```

```
              50                      55                      60
Gly Ser Gly Ser Gly Thr Asp Phe Thr Leu Thr Ile Ser Arg Leu Glu
65                      70                      75                      80
Pro Glu Asp Phe Ala Val Tyr Tyr Cys Gln Gln Tyr Ser Ser Ser Pro
                        85                      90                      95
Leu Thr Phe Gly Gly Gly Thr Lys Val Glu Ile Lys Arg Thr Val Ala
                100                     105                     110
Ala Pro Ser Val Phe Ile Phe Pro
                115                     120

<210> 13
<211> 381
<212> DNA
<213> Homo sapiens

<400> 13
caggtgcagc tggtgcagtc tggggctgag gtgaagaagc ctgggtcctc ggtgaaggtc  60
tcctgcaagg cttctggagg cacccttcagc aggtatatta tcaactgggt gcgacaggcc  120
cctggacaag ggcttgagtg gatgggaagg atcatcccta tccttggtgt agaaaactac  180
gcacagaagt tccagggcag agtcacgatt accgcggaca aatccacgag cacagcctac  240
atggagctga gcagcctgag atctgaggac acggccgtgt attactgtgc gagaaaggac  300
tggtttgatt actggggcca gggaaccctg gtcaccgtct cctcagcctc caccaagggc  360
ccatcggtct tccccctggc a                                             381

<210> 14
<211> 127
<212> PRT
<213> Homo sapiens

<400> 14
Gln Val Gln Leu Val Gln Ser Gly Ala Glu Val Lys Lys Pro Gly Ser
1                   5                       10                      15
Ser Val Lys Val Ser Cys Lys Ala Ser Gly Gly Thr Phe Ser Arg Tyr
                20                      25                      30
Ile Ile Asn Trp Val Arg Gln Ala Pro Gly Gln Gly Leu Glu Trp Met
                35                      40                      45
Gly Arg Ile Ile Pro Ile Leu Gly Val Glu Asn Tyr Ala Gln Lys Phe
    50                      55                      60
Gln Gly Arg Val Thr Ile Thr Ala Asp Lys Ser Thr Ser Thr Ala Tyr
65                      70                      75                      80
Met Glu Leu Ser Ser Leu Arg Ser Glu Asp Thr Ala Val Tyr Tyr Cys
                85                      90                      95
Ala Arg Lys Asp Trp Phe Asp Tyr Trp Gly Gln Gly Thr Leu Val Thr
                100                     105                     110
Val Ser Ser Ala Ser Thr Lys Gly Pro Ser Val Phe Pro Leu Ala
                115                     120                     125

<210> 15
<211> 418
<212> DNA
```

```
<213> Homo sapiens

<400> 15
atggaagccc cagcacagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gagtgttagc agctacttag cctggtacca gcagaaacct   180
ggccaggctc ccaggctcct catctatggt gcatccagca gggccactgg catcccagac   240
aggttcagtg gcagtgggtc tgggacagac ttcactctca ccatcagcag actggagcct   300
gaagattttg cagtgtatta ctgtcagcag tatggtagct caccgctcac tttcggcgga   360
gggaccaagg tggagatcaa acgaactgtg gctgcaccat ctgtcttcat cttccccg    418

<210> 16
<211> 119
<212> PRT
<213> Homo sapiens

<400> 16
Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Val Ser Ser Tyr
                20                  25                  30
Leu Ala Trp Tyr Gln Gln Lys Pro Gly Gln Ala Pro Arg Leu Leu Ile
            35                  40                  45
Tyr Gly Ala Ser Ser Arg Ala Thr Gly Ile Pro Asp Arg Phe Ser Gly
        50                  55                  60
Ser Gly Ser Gly Thr Asp Phe Thr Leu Thr Ile Ser Arg Leu Glu Pro
65                  70                  75                  80
Glu Asp Phe Ala Val Tyr Tyr Cys Gln Gln Tyr Gly Ser Ser Pro Leu
                85                  90                  95
Thr Phe Gly Gly Gly Thr Lys Val Glu Ile Lys Arg Thr Val Ala Ala
                100                 105                 110
Pro Ser Val Phe Ile Phe Pro
            115

<210> 17
<211> 5
<212> PRT
<213> Homo sapiens

<400> 17
Arg Tyr Pro Ile Asn
 1               5

<210> 18
<211> 17
<212> PRT
<213> Homo sapiens

<400> 18
Arg Ile Ile Pro Ile Leu Gly Ile Ala Asp Tyr Ala Gln Arg Phe Gln
```

```
          1               5              10              15
Gly

<210> 19
<211> 6
<212> PRT
<213> Homo sapiens

<400> 19
Arg Asp Trp Gly Asp Tyr
 1               5

<210> 20
<211> 12
<212> PRT
<213> Homo sapiens

<400> 20
Arg Ala Ser Gln Ser Val Ser Ser Ser Phe Leu Ala
 1               5              10

<210> 21
<211> 7
<212> PRT
<213> Homo sapiens

<400> 21
Gly Ala Ser Ser Arg Ala Thr
 1               5

<210> 22
<211> 9
<212> PRT
<213> Homo sapiens

<400> 22
Gln Gln Tyr Ser Ser Ser Pro Leu Thr
 1               5

<210> 23
<211> 5
<212> PRT
<213> Homo sapiens

<400> 23
Arg Tyr Ala Ile Asn
```

```
                    1               5

<210> 24
<211> 17
<212> PRT
<213> Homo sapiens

<400> 24
Arg Ile Ile Pro Ile Leu Asp Ile Ala Asp Tyr Ala Gln Lys Phe Gln
 1               5                  10                  15
Asp

<210> 25
<211> 6
<212> PRT
<213> Homo sapiens

<400> 25
Lys Asp Trp Phe Asp Pro
 1               5

<210> 26
<211> 12
<212> PRT
<213> Homo sapiens

<400> 26
Arg Ala Ser Gln Ser Gly Ser Ser Ser Tyr Leu Ala
 1               5                  10

<210> 27
<211> 7
<212> PRT
<213> Homo sapiens

<400> 27
Gly Ala Ser Ser Arg Ala Thr
 1               5

<210> 28
<211> 9
<212> PRT
<213> Homo sapiens

<400> 28
Gln Gln Tyr Gly Ser Ser Pro Ile Thr
```

```
                   1              5

<210> 29
<211> 5
<212> PRT
<213> Homo sapiens

<400> 29
Arg Tyr Pro Ile Asn
 1               5

<210> 30
<211> 17
<212> PRT
<213> Homo sapiens

<400> 30
Arg Ile Ile Pro Ile Leu Gly Ile Ala Asp Tyr Ala Gln Arg Phe Gln
 1               5                  10                  15
Gly

<210> 31
<211> 6
<212> PRT
<213> Homo sapiens

<400> 31
Arg Asp Trp Gly Asp Tyr
 1               5

<210> 32
<211> 12
<212> PRT
<213> Homo sapiens

<400> 32
Arg Ala Ser Gln Ser Val Ser Ser Ser Phe Leu Ala
 1               5                  10

<210> 33
<211> 7
<212> PRT
<213> Homo sapiens

<400> 33
Gly Ala Ser Ser Arg Ala Thr
```

```
1          5

<210> 34
<211> 9
<212> PRT
<213> Homo sapiens

<400> 34
Gln Gln Tyr Ser Ser Ser Pro Leu Thr
 1               5

<210> 35
<211> 5
<212> PRT
<213> Homo sapiens

<400> 35
Arg Tyr Ile Ile Asn
 1               5

<210> 36
<211> 17
<212> PRT
<213> Homo sapiens

<400> 36
Arg Ile Ile Pro Ile Leu Gly Val Glu Asn Tyr Ala Gln Lys Phe Gln
 1               5                  10                  15
Gly

<210> 37
<211> 6
<212> PRT
<213> Homo sapiens

<400> 37
Lys Asp Trp Phe Asp Tyr
 1               5

<210> 38
<211> 12
<212> PRT
<213> Homo sapiens

<400> 38
Arg Ala Ser Gln Ser Val Ser Ser Tyr Leu Ala
```

```
              1               5                    10

<210> 39
<211> 7
<212> PRT
<213> Homo sapiens

<400> 39
Gly Ala Ser Ser Arg Ala Thr
 1               5

<210> 40
<211> 9
<212> PRT
<213> Homo sapiens

<400> 40
Gln Gln Tyr Gly Ser Ser Pro Leu Thr
 1               5

<210> 41
<211> 20
<212> PRT
<213> Homo sapiens

<400> 41
Cys Ala Gly Gly Thr Lys Cys Ala Gly Cys Thr Gly Gly Thr Gly Cys
 1               5                    10                   15
Ala Gly Thr Cys
            20

<210> 42
<211> 20
<212> PRT
<213> Homo sapiens

<400> 42
Ser Ala Gly Gly Thr Gly Cys Ala Gly Cys Thr Gly Lys Thr Gly Gly
 1               5                    10                   15
Ala Gly Thr Cys
            20

<210> 43
<211> 20
<212> PRT
<213> Homo sapiens
```

```
<400> 43
Gly Ala Gly Gly Thr Gly Cys Ala Gly Cys Thr Gly Gly Thr Gly Cys
 1               5                  10                  15
Ala Gly Thr Cys
            20

<210> 44
<211> 21
<212> PRT
<213> Homo sapiens

<400> 44
Ala Thr Gly Gly Ala Cys Thr Gly Gly Ala Cys Cys Thr Gly Gly Ala
 1               5                  10                  15
Gly Cys Ala Thr Cys
            20

<210> 45
<211> 20
<212> PRT
<213> Homo sapiens

<400> 45
Ala Thr Gly Gly Ala Ala Thr Thr Gly Gly Gly Gly Cys Thr Gly Ala
 1               5                  10                  15
Gly Cys Thr Gly
            20

<210> 46
<211> 20
<212> PRT
<213> Homo sapiens

<400> 46
Ala Thr Gly Gly Ala Gly Thr Thr Thr Gly Gly Arg Cys Thr Gly Ala
 1               5                  10                  15
Gly Cys Thr Gly
            20

<210> 47
<211> 21
<212> PRT
<213> Homo sapiens

<400> 47
Ala Thr Gly Ala Ala Ala Cys Ala Cys Cys Thr Gly Thr Gly Gly Thr
 1               5                  10                  15
```

```
Thr Cys Thr Thr Cys
            20

<210> 48
<211> 20
<212> PRT
<213> Homo sapiens

<400> 48
Ala Thr Gly Gly Gly Gly Thr Cys Ala Ala Cys Cys Gly Cys Cys Ala
 1               5                  10                  15
Thr Cys Cys Thr
            20

<210> 49
<211> 21
<212> PRT
<213> Homo sapiens

<400> 49
Thr Gly Cys Cys Ala Gly Gly Gly Gly Gly Ala Ala Gly Ala Cys Cys
 1               5                  10                  15
Gly Ala Thr Gly Gly
            20

<210> 50
<211> 20
<212> PRT
<213> Homo sapiens

<400> 50
Arg Ala Cys Ala Thr Cys Cys Ala Gly Ala Thr Gly Ala Tyr Cys Cys
 1               5                  10                  15
Ala Gly Thr Cys
            20

<210> 51
<211> 20
<212> PRT
<213> Homo sapiens

<400> 51
Gly Tyr Cys Ala Thr Cys Tyr Arg Gly Ala Thr Gly Ala Cys Cys Cys
 1               5                  10                  15
Ala Gly Thr Cys
            20
```

```
<210> 52
<211> 20
<212> PRT
<213> Homo sapiens

<400> 52
Gly Ala Thr Ala Thr Thr Gly Thr Gly Ala Thr Gly Ala Cys Cys Cys
 1               5                  10                  15
Ala Gly Ala Cys
            20

<210> 53
<211> 20
<212> PRT
<213> Homo sapiens

<400> 53
Gly Ala Ala Ala Thr Thr Gly Thr Gly Thr Thr Gly Ala Cys Arg Cys
 1               5                  10                  15
Ala Gly Thr Cys
            20

<210> 54
<211> 20
<212> PRT
<213> Homo sapiens

<400> 54
Gly Ala Ala Ala Thr Trp Gly Thr Arg Ala Thr Gly Ala Cys Ala Cys
 1               5                  10                  15
Ala Gly Thr Cys
            20

<210> 55
<211> 20
<212> PRT
<213> Homo sapiens

<400> 55
Gly Ala Thr Gly Thr Thr Gly Thr Gly Ala Thr Gly Ala Cys Ala Cys
 1               5                  10                  15
Ala Gly Thr Cys
            20

<210> 56
<211> 20
<212> PRT
<213> Homo sapiens
```

```
<400> 56
Gly Ala Ala Ala Thr Thr Gly Thr Gly Cys Thr Gly Ala Cys Thr Cys
1               5                   10                  15
Ala Gly Thr Cys
            20

<210> 57
<211> 24
<212> PRT
<213> Homo sapiens

<400> 57

Cys Cys Cys Gly Cys Thr Cys Ala Gly Cys Thr Cys Cys Thr Gly Gly
1               5                   10                  15
Gly Gly Cys Thr Cys Cys Thr Gly
            20

<210> 58
<211> 23
<212> PRT
<213> Homo sapiens

<400> 58
Cys Cys Cys Thr Gly Cys Thr Cys Ala Gly Cys Thr Cys Cys Thr Gly
1               5                   10                  15
Gly Gly Gly Cys Thr Gly Cys
            20

<210> 59
<211> 26
<212> PRT
<213> Homo sapiens

<400> 59
Cys Cys Cys Ala Gly Cys Gly Cys Ala Gly Cys Thr Thr Cys Thr Cys
1               5                   10                  15
Thr Thr Cys Cys Thr Cys Cys Thr Gly Cys
            20                  25

<210> 60
<211> 27
<212> PRT
<213> Homo sapiens

<400> 60
```

```
Ala Thr Gly Gly Ala Ala Cys Cys Ala Thr Gly Gly Ala Ala Gly Cys
 1               5                   10                  15
Cys Cys Cys Ala Gly Cys Ala Cys Ala Gly Cys
            20              25
```

```
<210> 61
<211> 20
<212> PRT
<213> Homo sapiens

<400> 61
Cys Gly Gly Gly Ala Ala Gly Ala Thr Gly Ala Ala Gly Ala Cys Ala
 1               5                   10                  15
Gly Ala Thr Gly
            20
```